United States Patent
Astafieva et al.

(10) Patent No.: US 9,968,603 B2
(45) Date of Patent: May 15, 2018

(54) SYSTEMS FOR SUSTAINED INTRAOCULAR DELIVERY OF LOW SOLUBILITY COMPOUNDS FROM A PORT DELIVERY SYSTEM IMPLANT

(71) Applicant: ForSight Vision4, Inc., Menlo Park, CA (US)

(72) Inventors: Irina Astafieva, Palo Alto, CA (US); Judit Horvath, Cupertino, CA (US); Kathleen Cogan Farinas, Los Altos, CA (US); Blaine Bueche, San Jose, CA (US); Signe Erickson, Redwood City, CA (US)

(73) Assignee: FORSIGHT VISION4, INC., Menlo Park, CA (US)

( * ) Notice: Subject to any disclaimer, the term of this patent is extended or adjusted under 35 U.S.C. 154(b) by 387 days.

(21) Appl. No.: 14/212,817

(22) Filed: Mar. 14, 2014

(65) Prior Publication Data
US 2014/0276482 A1    Sep. 18, 2014

Related U.S. Application Data

(60) Provisional application No. 61/783,611, filed on Mar. 14, 2013.

(51) Int. Cl.
| | | |
|---|---|---|
| *A61K 47/00* | (2006.01) | |
| *A61K 31/506* | (2006.01) | |
| *A61K 31/404* | (2006.01) | |
| *A61K 31/4439* | (2006.01) | |
| *A61K 31/416* | (2006.01) | |

(Continued)

(52) U.S. Cl.
CPC .......... *A61K 31/506* (2013.01); *A61K 9/0051* (2013.01); *A61K 9/08* (2013.01); *A61K 31/404* (2013.01); *A61K 31/416* (2013.01); *A61K 31/444* (2013.01); *A61K 31/4439* (2013.01); *A61K 47/14* (2013.01); *A61K 47/32* (2013.01); *A61K 47/40* (2013.01)

(58) Field of Classification Search
CPC .................. A61F 9/0017; A61F 9/0008; A61F 2250/0068; A61F 2/14; A61K 9/0051
See application file for complete search history.

(56) References Cited

U.S. PATENT DOCUMENTS

| | | |
|---|---|---|
| 2,564,977 A | 8/1951 | Hu et al. |
| 2,585,815 A | 2/1952 | McLintock |

(Continued)

FOREIGN PATENT DOCUMENTS

| | | |
|---|---|---|
| CN | 101327356 A | 12/2008 |
| CN | 101600476 A | 12/2009 |

(Continued)

OTHER PUBLICATIONS

"Captisol—Cyclodextrins General", http://www.captisol.com/faq/cyclodextrins-general/, printed Jan. 24, 2016.*

(Continued)

*Primary Examiner* — Susan Su
(74) *Attorney, Agent, or Firm* — Mintz, Levin, Cohn, Ferris, Glovsky and Popeo, P.C.

(57) ABSTRACT

Therapeutic agent delivery formulations for the sustained release of therapeutic agents from a Port Delivery System (PDS) implant is described in this application.

22 Claims, 15 Drawing Sheets

(51) Int. Cl.
  *A61K 31/444*  (2006.01)
  *A61K 9/00*    (2006.01)
  *A61K 47/14*   (2017.01)
  *A61K 47/32*   (2006.01)
  *A61K 9/08*    (2006.01)
  *A61K 47/40*   (2006.01)

(56) References Cited

U.S. PATENT DOCUMENTS

| | | |
|---|---|---|
| 2,886,497 A | 5/1959 | Butler |
| 3,232,117 A | 2/1966 | Gilmont |
| 3,416,530 A | 12/1968 | Ness |
| 3,618,604 A | 11/1971 | Ness |
| 3,641,237 A | 2/1972 | Gould et al. |
| 3,828,777 A | 8/1974 | Ness |
| 3,831,583 A | 8/1974 | Edmunds, Jr. et al. |
| 3,845,201 A | 10/1974 | Haddad et al. |
| 3,902,495 A | 9/1975 | Weiss et al. |
| 3,914,402 A | 10/1975 | Shell |
| 3,916,899 A | 11/1975 | Theeuwes et al. |
| 3,926,188 A | 12/1975 | Baker et al. |
| 3,949,748 A | 4/1976 | Malmin |
| 3,949,750 A | 4/1976 | Freeman |
| 3,961,628 A | 6/1976 | Arnold |
| 3,977,404 A | 8/1976 | Theeuwes |
| 3,995,635 A | 12/1976 | Higuchi et al. |
| 4,008,719 A | 2/1977 | Theeuwes et al. |
| 4,014,333 A | 3/1977 | McIntyre |
| 4,014,334 A | 3/1977 | Theeuwes et al. |
| 4,014,335 A | 3/1977 | Arnold |
| 4,034,756 A | 7/1977 | Higuchi et al. |
| 4,034,758 A | 7/1977 | Theeuwes |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,519,030 A | 5/1996 | Shigemitsu et al. |
| 5,554,132 A | 9/1996 | Straits et al. |
| 5,562,915 A | 10/1996 | Lowe et al. |
| 5,578,042 A | 11/1996 | Cumming |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,534,524 B1 | 3/2003 | Kania et al. |
| 6,551,291 B1 | 4/2003 | de Juan, Jr. et al. |
| 6,573,293 B2 | 6/2003 | Tang et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,878,714 B2 | 4/2005 | Askew et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 6,995,162 B2 | 2/2006 | Chen et al. |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |

(56) References Cited

U.S. PATENT DOCUMENTS

| | | |
|---|---|---|
| 7,094,226 B2 | 8/2006 | Yaacobi |
| 7,105,530 B2 | 9/2006 | Boloor et al. |
| 7,117,870 B2 | 10/2006 | Prescott |
| 7,125,905 B2 | 10/2006 | Tang et al. |
| 7,141,023 B2 | 11/2006 | Diermann et al. |
| 7,141,152 B2 | 11/2006 | Le Febre |
| 7,141,581 B2 | 11/2006 | Bender et al. |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,211,600 B2 | 5/2007 | Lipson et al. |
| 7,235,576 B1 | 6/2007 | Riedl et al. |
| 7,262,203 B2 | 8/2007 | Boloor et al. |
| 7,276,050 B2 | 10/2007 | Franklin |
| 7,297,709 B2 | 11/2007 | Dai et al. |
| 7,351,834 B1 | 4/2008 | Riedl et al. |
| 7,452,913 B2 | 11/2008 | Sun et al. |
| 7,468,065 B2 | 12/2008 | Weber et al. |
| 7,476,510 B2 | 1/2009 | Kapur et al. |
| 7,528,255 B2 | 5/2009 | Riedl et al. |
| 7,572,924 B2 | 8/2009 | Tang et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,687,643 B2 | 3/2010 | Tasker et al. |
| 7,709,049 B2 | 5/2010 | Chappa |
| 7,772,404 B2 | 8/2010 | Borchardt et al. |
| 7,883,717 B2 | 2/2011 | Varner et al. |
| 7,893,040 B2 | 2/2011 | Loftsson et al. |
| 7,897,623 B2 | 3/2011 | Riedl et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,943,782 B2 | 5/2011 | Henry |
| 7,960,564 B2 | 6/2011 | Borchardt et al. |
| 7,973,068 B2 | 7/2011 | Demopulos et al. |
| 7,989,631 B2 | 8/2011 | Alva et al. |
| 8,058,445 B2 | 11/2011 | Tasker |
| 8,063,091 B2 | 11/2011 | Dai et al. |
| 8,114,885 B2 | 2/2012 | Boloor et al. |
| 8,128,954 B2 * | 3/2012 | Davis ................. A61K 9/0051 424/426 |
| 8,211,830 B2 | 7/2012 | Bailey et al. |
| 8,277,830 B2 | 10/2012 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1 | 6/2005 | Bene et al. |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 * | 11/2005 | Hughes ................. A61F 9/0008 424/427 |
| 2005/0250737 A1 * | 11/2005 | Hughes ................. A61K 9/0048 514/58 |
| 2005/0255144 A1 | 11/2005 | Schultz |
| 2005/0256499 A1 | 11/2005 | Pettis et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |

(56) References Cited

U.S. PATENT DOCUMENTS

| | | |
|---|---|---|
| 2008/0038317 A1* | 2/2008 | Chang .................. A61K 9/0051 424/428 |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0074786 A1 | 3/2009 | Dor et al. |
| 2009/0081271 A1 | 3/2009 | Clarke et al. |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0312724 A1* | 12/2009 | Pipkin .................. A61K 9/0043 604/294 |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0223979 A1 | 9/2010 | Ploehn et al. |
| 2010/0227904 A1 | 9/2010 | Kabra et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2010/0331548 A1 | 12/2010 | Liu et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2011/0281901 A1 | 11/2011 | Gupta |
| 2012/0028918 A1 | 2/2012 | Gupta |
| 2012/0029445 A1 | 2/2012 | de Juan, Jr. et al. |
| 2012/0029470 A1 | 2/2012 | Juan, Jr. et al. |
| 2012/0040986 A1 | 2/2012 | Riedl et al. |
| 2012/0157521 A1* | 6/2012 | Kremmidiotis ...... C07D 307/86 514/469 |
| 2013/0012531 A1 | 1/2013 | King et al. |
| 2013/0245544 A1 | 9/2013 | de Juan, Jr. et al. |

(56) References Cited

U.S. PATENT DOCUMENTS

| | | | |
|---|---|---|---|
| 2013/0274691 A1* | 10/2013 | de Juan, Jr. | A61F 9/0017 604/294 |
| 2013/0324942 A1 | 12/2013 | de Juan, Jr. et al. | |
| 2015/0190279 A1* | 7/2015 | Acharya | A61K 9/0051 604/290 |

FOREIGN PATENT DOCUMENTS

| | | |
|---|---|---|
| CN | 102365109 A | 2/2012 |
| EP | 0033042 B1 | 8/1984 |
| EP | 0 228 185 A1 | 11/1986 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 | 6/2006 |
| EP | 1385452 B1 | 9/2006 |
| EP | 1409065 B1 | 1/2007 |
| EP | 1337284 B1 | 12/2007 |
| EP | 1911481 | 4/2008 |
| EP | 1521572 B1 | 3/2009 |
| JP | 01-149716 A | 6/1989 |
| JP | 01-197429 A | 8/1989 |
| JP | 2004-524866 A | 8/2004 |
| JP | 2009-514888 A | 4/2009 |
| JP | 2009-523821 A | 6/2009 |
| JP | 2009-529968 A | 8/2009 |
| JP | 2010-521470 A | 6/2010 |
| WO | WO-88/04573 | 6/1988 |
| WO | WO-90/07545 | 7/1990 |
| WO | WO-95/28984 | 11/1995 |
| WO | WO-97/29850 | 8/1997 |
| WO | WO-98/25982 | 6/1998 |
| WO | WO-00/48660 | 8/2000 |
| WO | WO-01/26714 | 4/2001 |
| WO | WO-01/50943 | 7/2001 |
| WO | WO-01/68016 | 9/2001 |
| WO | WO-02/053128 A2 | 7/2002 |
| WO | WO-02/100318 | 12/2002 |
| WO | WO-03/028765 | 4/2003 |
| WO | WO-03/077972 | 9/2003 |
| WO | WO-03/082188 | 10/2003 |
| WO | WO-2004/000267 | 12/2003 |
| WO | WO-2004/112653 | 12/2004 |
| WO | WO-2005/016401 | 2/2005 |
| WO | WO-2005/027906 | 3/2005 |
| WO | WO-2005/028006 | 3/2005 |
| WO | WO-2005/091922 | 10/2005 |
| WO | WO-2005/107705 | 11/2005 |
| WO | WO-2005/110362 | 11/2005 |
| WO | WO-2005/110436 | 11/2005 |
| WO | WO-2005/110473 | 11/2005 |
| WO | WO-2005/117780 | 12/2005 |
| WO | WO-2006/014484 | 2/2006 |
| WO | WO-2006/015385 | 2/2006 |
| WO | WO-2006/023530 | 3/2006 |
| WO | WO-2006/031358 | 3/2006 |
| WO | WO-2006/031388 | 3/2006 |
| WO | WO-2006/044614 | 4/2006 |
| WO | WO-2006/050221 | 5/2006 |
| WO | WO-2006/068838 | 6/2006 |
| WO | WO-2006/071554 | 7/2006 |
| WO | WO-2006/082588 | 8/2006 |
| WO | WO-2006/108054 | 10/2006 |
| WO | WO-2006/127962 | 11/2006 |
| WO | WO-2006/138609 | 12/2006 |
| WO | WO-2007/012974 | 2/2007 |
| WO | WO-2007/035473 | 3/2007 |
| WO | WO-2007/035621 | 3/2007 |
| WO | WO-2007/038453 | 4/2007 |
| WO | WO-2007/044534 | 4/2007 |
| WO | WO-2007/047744 | 4/2007 |
| WO | WO-2007/064752 A2 | 6/2007 |
| WO | WO-2007/066339 | 6/2007 |
| WO | WO-2007/084582 | 7/2007 |
| WO | WO-2007/084765 | 7/2007 |
| WO | WO-2007/101204 | 9/2007 |
| WO | WO-2007/115259 A2 | 10/2007 |
| WO | WO-2007/117394 | 10/2007 |
| WO | WO-2007/131050 | 11/2007 |
| WO | WO-2007/133761 | 11/2007 |
| WO | WO-2007/133762 | 11/2007 |
| WO | WO-2008/003043 | 1/2008 |
| WO | WO-2008/005240 | 1/2008 |
| WO | WO-2008/011125 | 1/2008 |
| WO | WO-2008/019265 | 2/2008 |
| WO | WO-2008/033924 | 3/2008 |
| WO | WO-2008/040062 | 4/2008 |
| WO | WO-2008/045272 | 4/2008 |
| WO | WO-2008/052145 | 5/2008 |
| WO | WO-2008/060359 | 5/2008 |
| WO | WO-2008/061043 A2 | 5/2008 |
| WO | WO-2008/076544 | 6/2008 |
| WO | WO-2008/094989 | 8/2008 |
| WO | WO-2008/115290 | 9/2008 |
| WO | WO-2008/116165 | 9/2008 |
| WO | WO-2008/144340 | 11/2008 |
| WO | WO-2008/144919 | 12/2008 |
| WO | WO-2009/012075 | 1/2009 |
| WO | WO-2009/023615 | 2/2009 |
| WO | WO-2009/046164 | 4/2009 |
| WO | WO-2009/055620 | 4/2009 |
| WO | WO-2009/055671 | 4/2009 |
| WO | WO-2009/055729 | 4/2009 |
| WO | WO-2009/055824 | 4/2009 |
| WO | WO-2009/061607 | 5/2009 |
| WO | WO-2009/073192 | 6/2009 |
| WO | WO-2009/086112 | 7/2009 |
| WO | WO-2009/089409 | 7/2009 |
| WO | WO-2009/094466 | 7/2009 |
| WO | WO-2009/112878 | 9/2009 |
| WO | WO-2009/117112 | 9/2009 |
| WO | WO-2009/124096 | 10/2009 |
| WO | WO-2009/128932 | 10/2009 |
| WO | WO-2009/134929 | 11/2009 |
| WO | WO-2009/137777 | 11/2009 |
| WO | WO-2009/143288 A1 | 11/2009 |
| WO | WO-2010/008424 | 1/2010 |
| WO | WO-2010/021993 | 2/2010 |
| WO | WO-2010/047753 | 4/2010 |
| WO | WO-2010/062628 | 6/2010 |
| WO | WO-2010/066714 | 6/2010 |
| WO | WO-2010/075565 | 7/2010 |
| WO | WO-2010/078063 | 7/2010 |
| WO | WO-2010/088548 | 8/2010 |
| WO | WO-2010/093945 | 8/2010 |
| WO | WO-2010/095940 | 8/2010 |
| WO | WO-10088548 A1 | 8/2010 |
| WO | WO-2010/125416 | 11/2010 |
| WO | WO-2010/126908 | 11/2010 |
| WO | WO-2010/135369 | 11/2010 |
| WO | WO-2010/141729 | 12/2010 |
| WO | WO-2010/147661 | 12/2010 |
| WO | WO-2011/008896 | 1/2011 |
| WO | WO-2011/008897 | 1/2011 |
| WO | WO-2011/028850 | 3/2011 |
| WO | WO-2011/034627 | 3/2011 |
| WO | WO-2011/069053 A1 | 6/2011 |
| WO | WO-2011/0075481 A1 | 6/2011 |
| WO | WO-2011/079232 | 6/2011 |
| WO | WO-2011/140343 A1 | 11/2011 |
| WO | WO-2012/019047 A2 | 2/2012 |
| WO | WO-2012/019136 | 2/2012 |
| WO | WO-2012/019176 A2 | 2/2012 |
| WO | WO-12042421 A1 | 4/2012 |
| WO | WO-2012/065006 A2 | 5/2012 |
| WO | WO-2012/103060 A1 | 8/2012 |
| WO | WO-2013/003620 | 1/2013 |
| WO | WO-2013/022801 | 2/2013 |
| WO | WO-2013/033176 A1 | 3/2013 |

(56) References Cited

FOREIGN PATENT DOCUMENTS

| WO | WO-2013/151568 A1 | 10/2013 |
| WO | WO-2014/064652 A2 | 5/2014 |

OTHER PUBLICATIONS

.Beta.-cyclodextrin, sulfobutyl ethers, sodium salts, http://www.chemicalbook.com/ChemicalProductProperty_EN_CB41208906.htm, printed Jan. 24, 2016.*
Black et al., Handbook of Biomaterial Properties, pp. 115 & 126, Chapman & Hall, 1998.*
AMD Preclinical Studies. Anti-Factor D Fab Specifically Inhibits the Alternative Pathway. The Association for Research in Vision and Ophthalmology, Inc. 2010.
Andrews, "Effect of nonsteroidal anti-inflammatory drugs on LFA-1 and ICAM-1 expression in gastric mucosa," Am J Physiol. Apr. 1994;266(4 Pt 1):G657-664.
Arvo, Agenda for the Summer Eye Research Conference, (Jul. 2009).
Avery et al., "Intravitreal bevacizumab (Avastin) in the treatment of proliferative diabetic retinopathy," Ophthalmology. Oct. 2006, 113(10):1695-1705.e6.
Bakri et al., "The effect of intravitreal triamcinolone acetonide on intraocular pressure," Ophthalmic Surgery, Lasers and Imaging, Sep./Oct. 2003; 34(5): 386-390.
Bird et al., Transport Phenomena, John Wiley & Sons, Inc., New York, 1960, pp. 196-201.
Block et al., "Solubility and dissolution of triamcinolone acetonide," Journal of Pharmaceutical Sciences,Apr. 1973; 62(4):617-621.
Breslin, C.W., et al., "Chapter 7. Slow Release Artificial Tears", Symposium on Ocular Therapy pp. 77-83, 1977.
Brewster, Marcus E. and Loftsson, Thorsteinn. "Cyclodextrins as pharmaceutical solubilizers". Advanced Drug Delivery Reviews. 59: 645-666 (2007).
Castro et al., "Effect of COX inhibitors on VEGF-induced retinal vascular leakage and experimental corneal and choroidal neovascularization," Exp Eye Res. Aug. 2004;79(2):275-285.
Chirila et al., "The Vitreous Humor" in Handbook of Biomaterial Properties, eds. Black & Hastings. Chapman & Hall, London, 1998; pp. 125-131.
Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010.
Deissler et al., "VEGF-induced effects on proliferation, migration and tight junctions are restored by ranibizumab (Lucentis) in microvascular retinal endothelial cells," Br J Ophthalmol 2008;92:839-843.
Del Amo, et al., Current & future ophthalmic drug delivery systems . . . , Drug Discovery Today, vol. 13, Nos. 3/4, Feb. 2008.
Donoso et al., "The role of inflammation in the pathogenesis of age-related macular degeneration," Surv Ophthalmol. Mar.-Apr. 2006;51(2):137-52.
Duvvuri et al., Drug Delivery to the Retina: Challenges and Opportunities, Expert Opinion on Biological Therapy, 2003, vol. 3(1): 45-56.
European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.
Funatsu et al. "Association of vitreous inflammatory factors with diabetic macular edema," Ophthalmology 2009;116:73-79.
Gaudana et al., Recent Perspectives in Ocular Drug Delivery, Pharmaceutical Research, 2008.
Gaudana R. et al. "Ocular Drug Delivery." AAPS J., 12(3): 348-360 (2010).
Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: <<http://www.iovs.org/cgi/reprint/46/2/726>>.
Gillies et al., "Intravitreal triamcinolone for refractory diabetic macular edema: two-year results of a double-masked, placebo-controlled, randomized clinical trial," Ophthalmology. Sep. 2006;113(9):1533-1538.
Haller, An Overview of Sustained-release Drug Implants, Retinal Physician, Jan. 2008.
Hastedt & Wright, "Diffusion in porous materials above the percolation threshold," Pharm. Res. Sep. 1990; 7(9):893-901 (1990).
Heier et al, "Ketorolac versus prednisolone versus combination therapy in the treatment of acute pseudophakic cystoid macular edema," Ophthalmology. Nov. 2000;107(11):2034-2038;discussion 2039.
Iwase et al. "Topical pazopanib blocks VEGF-induced vascular leakage and neovascularization in the mouse retina but is ineffective in the rabbit". Invest. Ophthalmol. Vis. Sci. (2013) 54(1):503-11.
Janoria et al., Novel Approaches to Retinal Drug Delivery, Expert Opinion Drug Delivery, 2007.
Jena et al., "A Novel Technique for Surface Area and Particle Size Determination of Components of Fuel Cells and Batteries," Porous Materials, Inc., Dec. 2006, 3 pages total. Downloaded from the Internet: <<http://www.pmiapp.com/publications/docs/A_Novel_technique_for_surface_area.pdf>>.
"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.
Kang et al., "Inhibitory effects of anti-inflammatory drugs on interleukin-6 bioactivity," Biol Pharm Bull. Jun. 2001;24(6):701-703.
Katz, I.M., et al., "A Soluble Sustained-Release Ophthalmic Delivery Unit", 8:5 (May 1977) pp. 728-734.
Lamberts, D.W., M.D., et al., "A Clinical Study of Slow-Releasing Artificial Tears", Ophthalmology 85 (1978) pp. 794-800.
Lee, D.A., et al., "Glaucoma Filtration Surgery in Rabbits Using Bioerodible Polymers and 5-Fluorouracil", Ophthalmology 94:12 (1987) pp. 1523-1530.
Lee, D.A., et al., "The Use of Bioerodible Polymers and 5-Fluorouracil in Glaucoma Filtration Surgery", Investigative Ophthalmology & Visual Science 29-11 (1988) pp. 1692-1697.
Li, et al., An electrochemical introculardrug delivery device, Science Direct, Sensors and Actuators, www.sciencedirect.com,Jul. 4, 2007.
Lopez-Armada et al., "Modulation of cell recruitment by anti-inflammatory agents in antigen-induced arthritis," Ann Rheum Dis Nov. 2002;61(11):1027-1030.
Luncentis, INN-Ranibizumab, "Scientific Discussion," European Medicines Agency ; retrieved from the Internet:<http://www.ema.europa.eu/docs/en_GB/document_library/EPAR_-_Assessment_Report_-_Variation/human/000715/WC500101009.pdf>. Oct. 21, 2010.
"MAbPac SCX-10 Folumn for Monoclonal Antibody Variant Analysis." Dionex.Aug. 2010. [http://www.dionex.com/en-us/webdocs/87008-DS-MAbPac-SCX-10-Column-20Aug2010-LPN2567-03.pdf]. Web. Retrieved May 2012.
Metal Powder Industries Federation, Porous Metal Design Guidebook, 2007, 24 pages total. Downloaded from the Internet: <<http://www.mpif.org/DesignCenter/porous.pdf>>.
Miller, DP, et al., Thermophysical Properties of Trehalose and Its Concentrated Aqueous Solutions,Pharmaceutical Research, vol. 14, No. 5, 1997, pp. 578-590.
Molokhia et al, "Transscleral iontophoretic and intravitreal delivery of a macromolecule: Study of ocular distribution in vivo and postmortem with MRI", Experimental Eye Research 88 (2009) 418-425.
Moritera, T., et al., "Microspheres of Biodegradable Polymers as a Drug-Delivery System in the Vitreous", Investigative Ophthalmology & Visual Science 32-6 (1991) pp. 1785-1790.

(56) References Cited

OTHER PUBLICATIONS

MOTT Corporation, "Sintered Metal Powder Media," American Filtration & Separation Society 2007, 2 pages total. Downloaded from the Internet:<<http://www.afssociety.org/education/0907oneminute.htm>>.

Navarro, "The Optical Design of the Human Eye: a Critical Review," J Optom, Jan.-Mar. 2009 2(1): 3-18.

Nutan, MTH, et al., *General Principles of Suspensions, in Pharmaceutical Suspensions Fron Formulation Development to Manufacturing*, editors AK Kulshreshtha, et al., Spinger, 2010.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: <<http://www.iovs.org/cgi/reprint/44/6/2702>>.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm.

Saline (medicine)—Wikipedia, the free encyclopedia. http://web.archive.org/web/20110205192937/http://en.wikipedia.org/wiki/Saline_(medicine). Apr. 27, 2012.

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).

Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.

Smith et al., "Spectrophotometric determination of pKa values for fluorescein using activity coefficient corrections," WaterSA 2002; 28(4):395-402.

Smith, T.J., et al., "Intravitreal Sustained-Release Ganciclovir", *Arch. Ophthamol* 110 (1992) pp. 255-258.

Soheilian et al., "Pilot Study of Intravitreal Injection of Diclofenac for Treatment of Macular Edema of Various Etiologies," Retina, Mar. 2010; 30(3): 509-515.

Stay et al. Computer Simulation of Convective and Diffusive Transport of Controlled-Release Drugs in the vitreous Humor, *Pharm Res* 2003,20(1), pp. 96-102.

Stella et al.. "Cylcodextrins." *Toxicologic Pathology*. 36: 3-16 (1999) Web. Retrieved Feb. 19, 2013.

Theodossiadis et al., "Intravitreal administration of the anti-tumor necrosis factor agent infliximab for neovascular age-related macular degeneration," Am J Ophthalmol. May 2009;147(5):825-830.

Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.

Yao et al. (Prevention of Laser Photocoagulation Induced Choroidal Neovascularization Lesions by Intravitreal Doses of Ranibizumab in Cynomolgus Monkeys, ARVO 2009 abstract D906).

International Search Report and Written Opinion issued in International Application No. PCT/US2014/028396, dated Aug. 19, 2014.

Arakawa, Tsutomu, et. al. "Factors affecting short-term and long-term stabilities of proteins." Advanced Drug Delivery Reviews, vol. 10, No. 1, 1993, pp. 1-28.

* cited by examiner

SYSTEMS FOR SUSTAINED INTRAOCULAR DELIVERY OF LOW SOLUBILITY COMPOUNDS FROM A PORT DELIVERY SYSTEM IMPLANT

RELATED APPLICATIONS

This application claims priority to, and the benefit of, U.S. provisional application No. 61/783,611, filed Mar. 14, 2013, the entire content of which is incorporated herein by reference in its entirety.

FIELD OF INVENTION

Embodiments disclosed herein are generally directed to systems comprising a therapeutic device and a formulation of a therapeutic agent having low solubility in water, where the systems are tuned to increase the solubility of the therapeutic agent at least 1000 fold in the formulation. The therapeutic device of the current invention is used for intravitreal delivery of high concentration of the therapeutic agent at the vitreous for up to six months, where, upon delivery, the high concentration of the therapeutic agent is maintained for an extended period, e.g., up to at least 60 days. The disclosed embodiments are also directed to extending the half-life of the therapeutic agent by delivering the formulation by diffusion from a therapeutic device.

BACKGROUND

Preparing formulations of therapeutic agents that have low solubility in water and delivering the agents to a target tissue have been a major challenge for pharmacologists and therapeutic agent delivery scientists. See Gaudana R. et al., *Ocular Therapeutic agent Delivery*, AAPS J., 12(3): 348-360 (2010). The combined effect of the unique anatomy and physiology of the eye and the low water solubility of the therapeutic agents for treating ocular diseases or disorders have frustrated the delivery of these agents to a desired target site of the eye. See Gaudana. There is, therefore, a need for formulations and delivery systems, which will allow high solubility of the therapeutic agents and improve stability and efficacy at the target tissues.

Protein kinases have been implicated in ocular diseases, not limited to, but including age related macular degeneration (hereinafter "AMD"), diabetic macular edema and proliferative diabetic retinopathy. Transmembrane receptor protein kinases exhibit an extracellular domain, capable of ligand binding. These ligand binding mechanisms trigger activation of the kinase catalytic domain which initiates a cascade of signals that controls intracellular functions.

Examples of receptor protein kinase are growth factors such as EGF, FGF, VEGF, PDGF and IGF. Elevated levels of soluble growth factors, such as vascular endothelial growth factor-A (VEGF), have been found in ocular tissues and fluids removed from patients with pathologic ocular angiogenesis. Various ocular tissues including the neurosensory retina and retinal pigmented epithelium (RPE) are known to respond to hypoxia, inflammation, and trauma by increasing VEGF expression that can lead to blood-retina barrier breakdown (i.e., enhanced vascular permeability and extracellular edema) and/or pathologic neovascularization (NV).

Delivery of therapeutic agents in the eye is challenging. Major drawbacks exist in the current delivery means because of the recurrent intravitreal injections required for chronic maintenance therapy. Repeated intravitreal injections present both a risk and a burden to patients. Endophthalmitis, retinal detachments, traumatic cataract, and increased intraocular pressure (IOP) are all potential vision-threatening sequela to the intravitreal route of administration. Moreover, monthly treatment or even monthly monitoring is a substantial burden to patients, their caregivers, and to the medical community, especially when considering that treatment may need to persist for a patient's lifetime. While roughly one-third of patients experience improved vision when treated with repeated intravitreal injections of certain biologic VEGF inhibitors, the majority of patients experience only stabilization of reduced vision.

Formulations may provide less than ideal stability in one or more ways when injected into a therapeutic device in at least some instances. For example, a buffer of the injected formulation may be released from the device into the vitreous in at least some instances. Also, diffusion of hydrogen ions and hydroxide ions between the reservoir and the vitreous may affect the pH of the formulation within the device.

In at least some instances, a buffer of a fluid of the eye such as the vitreous humor having a physiological pH may enter the device and affect the pH of the formulation within the device, such that the stability of the therapeutic agent may be less than ideal in at least some instances.

In at least some instances, formulation components added to increase the solubility of the therapeutic agents may bind the therapeutic agent so strongly that efficacy at the target tissue may be less than ideal in at least some instances.

In light of the above, it is desirable to provide improved formulations of therapeutic agents for therapeutic devices that overcome at least some of the above deficiencies of the known formulations, for example with improved therapeutic agent release that can be maintained over an extended time when implanted.

Systems described here comprise a therapeutic device for intravitreal delivery of a therapeutic agent, and a formulation comprising the therapeutic agent. The systems disclosed here extends the half-life of a therapeutic agent in the vitreous humor of the eye.

SUMMARY OF THE INVENTION

Systems comprising a therapeutic device for intravitreal delivery of a therapeutic agent and formulations comprising the therapeutic agent are disclosed herein. The components of a particular device, e.g., a refillable sustained release therapeutic device, and the formulation when adjusted or tuned to achieve a desired stability and concentration of a therapeutic agent in the formulation, can also achieve desired delivery release rate of the therapeutic agent from the particular device. The formulation can be tuned to achieve high solubility and concentration of a therapeutic agent having low water solubility, at the vitreous, where the desired concentration and stability of the therapeutic agent can be maintained for an extended period after delivery. Protein kinase inhibitors are examples of therapeutic agents with low solubility in water.

The current embodiments provide tuning of the rate of therapeutic agent delivery from the reservoir of a therapeutic device to achieve the desired sustained release profile and desired tissue levels. In the present disclosure tuning is achieved by the design of a Port Delivery System (PDS) implant, which includes a porous structure for controlling therapeutic agent release. The porous structure has porosity and tortuosity, further having geometrical dimensions. The tuning of the rate of delivery is achieved by varying the reservoir volume. Formulation composition is also adjusted or tuned to increase stability and concentration of a therapeutic agent in the formulation and to control the rate of delivery from the reservoir.

In some embodiments, the tuning of the rate of therapeutic agent delivery depends on the formulation components, e.g., formulation agents, pH adjusting agents, nature of the complexing agents, concentration of the complexing agent, formulation viscosity, solubilizing/stabilizing agents, amphiphilic agents, and/or concentration of the therapeutic agents in the reservoir.

The present invention relates to a system comprising a therapeutic device and a formulation comprising a therapeutic agent and one or more formulation agents, where the formulation is contained in the device. The device has a reservoir chamber coupled to a porous structure for controlled release of the therapeutic agent in the vitreous of the eye after the system is placed or inserted into the eye. The formulation is placed in the reservoir before delivery, and the controlled release of the therapeutic agent and formulation agents from the reservoir through the porous structure increases the half-life of the therapeutic agent in the vitreous.

According to some embodiments, the therapeutic agent is a poor or low water soluble compound. In some embodiments, the poor or low water soluble compound is a tyrosine kinase inhibitor. For example, the tyrosine kinase inhibitor is, without being a limiting example, Sunitinib, Pazopanib, or Axitinib. In some embodiments, the concentration of the tyrosine kinase inhibitor in the reservoir is about 1 mg/mL to about 100 mg/mL.

The formulation agents of the current embodiments include one or more complexing agents. Non-limiting examples of the complexing agents are 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, and any combination(s) thereof. The present disclosure provides the ratio of a complexing agent to therapeutic agent in the range of 1:1 and 15:1.

In some embodiments, the formulation agents comprise one or more solubilizing agents, and/or one or more stabilizing agents, and/or one or more pH adjusting agents, and/or one or more buffering agents.

For example, in some embodiments, the formulation agents comprise one or more amphiphilic agents such as polysorbates, block copolymers of ethylene oxide and propylene oxide, di-block polymers or tri-block copolymers of polyethylene oxide and polypropylene oxide, ethoxylated emulsifiers, polyethylene glycol esters, sucrose laurate, Tocopherol-PEG-succinate, phospholipids and their derivatives, other non-ionic self-emulsifying agents, or combinations thereof.

For example, the formulation agents comprise one or more solubilizing/stabilizing agents, for example, trehalose, methylcellulose, ethylcellulose, sodium carboxymethylcellulose, hydroxypropylmethylcellulose, sodium hyaluronate, sodium alginate, chitosan and its derivatives, polyethylene glycol, glycerin, propylene glycol, Triacetin, N,N-Dimethylacetamide, poly(vinyl pyrrolidone), pyrrolidone, dimethyl sulfoxide, ethanol, N-(-beta-Hydroxyethyl)-lactamide, 1-Methyl-2-pyrrolidinone, triglycerides, monothioglycerol, sorbitol, lecithin, methylparaben, propylparaben, or combinations thereof.

In some embodiments, the formulation agents comprise one or more pH adjusting agents. For example, the formulation agents comprise one or more agents for increasing buffering capacity of the formulation. The pH adjustment agent is, for example, sodium hydroxide, hydrochloric acid, citric acid, malic acid, tartaric acid, acetic acid, phosphoric acid, maleic acid, glycine, sodium lactate, lactic acid, sodium citrate, ascorbic acid, sodium acetate, acetic acid, sodium bicarbonate, sodium carbonate, carbonic acid, sodium succinate, succinic acid, sodium benzoate, benzoic acid, sodium phosphates, tris(hydroxymethyl)aminomethane, histidine, histidine hydrochloride, and combinations thereof. In some embodiments, the pH of the formulation in the reservoir is in the range from pH 2 to pH 8.

The present disclosure provides a formulation further comprising a tonicity adjusting agent selected from, for example, sodium chloride, sodium phosphate, and combinations thereof.

In some embodiments, the complexing agent in the formulation is β-cyclodextrin sulfobutyl ether; the solubilizing agent is poly(vinyl pyrrolidone) (PVP); and the pH adjusting agent is selected from hydrochloric acid, sodium hydroxide, citric acid, malic acid, and histidine.

In additional embodiments, the formulations comprise hydroxypropyl β-cyclodextrin as a complexing agent; poly (vinyl pyrrolidone) (PVP) as the solubilizing agent; and the pH adjusting agent is selected from hydrochloric acid, sodium hydroxide, citric acid, malic acid, and histidine. The complexing agent in the formulation comprises sodium salt of sulfobutyl ether-β-cyclodextrin.

The therapeutic agent is solubilized in the formulation comprising the complexing agent, pH adjusting agent, solubilizing agent, and/or amphiphilic agent, before or after placing into the reservoir. For example, the therapeutic agent is delivered for up to about 6 months after the system is inserted into the eye of a subject. In some embodiments, the therapeutic agent is delivered for at least 90 days after the system is inserted into the eye of a subject. In some embodiments the therapeutic agent is delivered from the reservoir into the vitreous for up to six months after the system is inserted into the eye of a subject. In some embodiments the therapeutic agent is delivered from the reservoir into the vitreous for at least 90 days after the system is inserted into the eye of a subject.

In some embodiments, the therapeutic agent is released at a release rate of about 0.1-50 μg/day from the porous structure after being inserted into the eye. The delivery of the therapeutic agent is achieved by increasing the stability of the agent in the reservoir and at the vitreous for at least 30 days. The stability of the therapeutic agent in the reservoir and at the vitreous is increased for at least 90 days. The stability of the therapeutic agent in the reservoir and at the vitreous is increased for up to 6 months. The pH of the formulation in the reservoir is between about pH 2-8.

The current embodiments provide a formulation for delivering about 1-100 mg/mL concentration of a therapeutic agent and formulation agents contained in a reservoir chamber coupled to a porous structure for controlled release of the about 1-100 mg/mL concentration of the therapeutic agent at the vitreous of the eye, where the about 1-100 mg/mL concentration of the therapeutic agent after the controlled release from the porous structure at the vitreous is sustained for 6 months. In an embodiment, the concentration of the therapeutic agent at the vitreous is sustained for up to 6 months.

An embodiment of the current invention provides a method of treating, preventing progression of, or ameliorating a symptom of a disease and/or disorder treatable, preventable or ameliorable by inhibiting a kinase characterized by vascular leakage and neovascularization (NV) in the retina of the eye of a subject, the method including providing a therapeutic device comprising a reservoir chamber and a porous structure, the reservoir chamber having a volume sized to receive an injection of an amount of a formulation of a therapeutic agent with low aqueous solubility (≥10,000-≥100 parts of solvent required for 1 part of solute), and the porous structure is configured to release an effective dose of the therapeutic agent into the vitreous humor of the eye. The formulation is injected into the reservoir chamber before the device is inserted into the eye. In some embodiments, the therapeutic agent treats, prevents progression of or ameliorates a symptom of retinopathy of the eye.

In an embodiment, the formulations of the current embodiments are used for treating, preventing progression of, or ameliorating a disease and/or disorder treatable, preventable or ameliorable by inhibiting a kinase characterized by vascular leakage and neovascularization (NV) in the retina of the eye of a subject. In yet another embodiment, a method is provided for the development of a medicament for treating, preventing progression of, or ameliorating a disorder characterized by vascular leakage and neovascularization (NV) in the retina of the eye of a subject. The formulations for use or the method for development of a medicament of the current invention may involve a formulation of a therapeutic agent in combination with one or more formulation agents, such as β-cyclodextrin sulfobutyl ether or hydroxypropyl-β-cyclodextrin; poly(vinyl pyrrolidone) (PVP); hydrochloric acid, sodium hydroxide, citric acid, malic acid, histidine, or combinations thereof.

The formulations for use or the method for development of a medicament of the current invention further include one or more pH adjustment agent, and one or more solubilizing agents.

The embodiments of the current invention further provide use of the formulation in treating, preventing progression of, or ameliorating a disease and/or disorder treatable, preventable or ameliorable by inhibiting a kinase disease characterized by vascular leakage and neovascularization (NV) in the retina of the eye of a subject. The vascular leakage and/or neovascularization for treating, preventing progression of, or ameliorating is associated with diabetic macular edema, neovascular age-related macular degeneration (AMD), pathologic choroidal neovascularization (CNV), pathologic neovascularization (NV), diabetic retinopathy (DR), ocular ischemia, retinal vein occlusion (central or branch), ocular trauma, surgery induced edema, surgery induced neovascularization, cystoidmacular edema, and uveitis; where the formulation is administered intravitreally to the eye.

In one embodiment the method of treating, preventing progression of, or ameliorating a symptom of a disorder of the eye may involve a formulation comprising one or more complexing agents, one or more pH adjustment agents, one or more solubilizing agents, or any combinations thereof. In one of the methods of treatment/prevention of progression/ameliorating a symptom of a disorder of the eye involve, a complexing agent, such as, β-cyclodextrin sulfobutyl ether or hydroxypropyl β-cyclodextrin; a solubilizing agent, such as, poly(vinyl pyrrolidone) (PVP); and an agent for pH adjustment, for example, hydrochloric acid, sodium hydroxide, citric acid, malic acid, or histidine.

In the treatment/prevention/amelioration methods of the current embodiment, the therapeutic agent is delivered for an extended period of time, for example, up to about three months after a therapeutic device implanted into the eye comprising a therapeutic formulation of the current invention is inserted into the eye of the subject. The treatment/prevention/amelioration is achieved with the therapeutic agent released at a release rate of about 0.1-50 µg/day from the therapeutic device after implantation. Upon release at the vitreous, the therapeutic agent is stable in the device for at least 30 days. In one embodiment the therapeutic agent is released from the device for at least 6 months. In some embodiments, the pH of the formulation in the device is between about pH 2-8.

The embodiments of the current invention further provide drug delivery formulations that may contain a therapeutic agent and one or more formulation agents. The formulation can be contained in a reservoir chamber coupled to a porous structure in a therapeutic agent delivery system for controlled release of the therapeutic agent in the vitreous of the eye such that the controlled release of the formulation from the porous structure produces a concentration of the therapeutic agent in the vitreous that is lower than the concentration of the therapeutic agent in the reservoir chamber by at least two orders of magnitude. In some embodiments, the therapeutic agent is poorly water soluble.

For example, the therapeutic agent has a solubility of less than 1 mg/mL in water, or less than 0.01 mg/mL in water. In some embodiments, the concentration of the therapeutic agent in the reservoir chamber is greater than 1 mg/mL. In one embodiment, the concentration of the therapeutic agent is about 10-15 mg/mL. The concentration is 11, 12, 13, 14 mg/mL.

In another embodiment, the one or more formulation agents increase the solubility of the therapeutic agent in the vitreous by at least two orders of magnitude over the solubility of therapeutic agent in an aqueous buffer. In some embodiments, the formulation agents increase the solubility of the therapeutic agent in an aqueous buffer over the solubility of the therapeutic agent, without being a limiting example, in a phosphate buffered saline. In some embodiments, more than 50% of the therapeutic agent in the reservoir chamber is bound to the complexing agent. In other embodiments, less than 50% of the therapeutic agent in the vitreous is bound to the complexing agent.

BRIEF DESCRIPTION OF THE DRAWINGS

In order to understand the invention and to demonstrate how it may be carried out in practice, embodiments now described, by way of non-limiting example only, with reference to the accompanying drawings in which:

FIG. 1A-1 shows a therapeutic device implanted at least partially within the sclera of the eye as in FIG. 1.

FIGS. 1A-1-1 shows a therapeutic device implanted under the conjunctiva and extending through the sclera to release a therapeutic agent into vitreous humor of the eye so as to treat the retina, in accordance with variations described herein.

FIG. 1A-2 shows structures of a therapeutic device configured for placement in an eye as in FIGS. 1A-1 and 1A-1-1, in accordance with variations described herein.

FIG. 1A-2-1 shows a therapeutic device loaded into an insertion cannula, in which the device comprises an elongate narrow shape for insertion into the sclera, and in which the device is configured to expand to a second elongate wide shape for retention at least partially in the sclera, in accordance with variations described herein. FIG. 1A-2-2 shows a therapeutic device comprising a reservoir suitable for loading in a cannula, in accordance with variations described herein.

FIG. 2 shows an access port suitable for incorporation with the therapeutic device, in accordance with variations described herein.

DETAILED DESCRIPTION OF THE INVENTION

Figure 1:
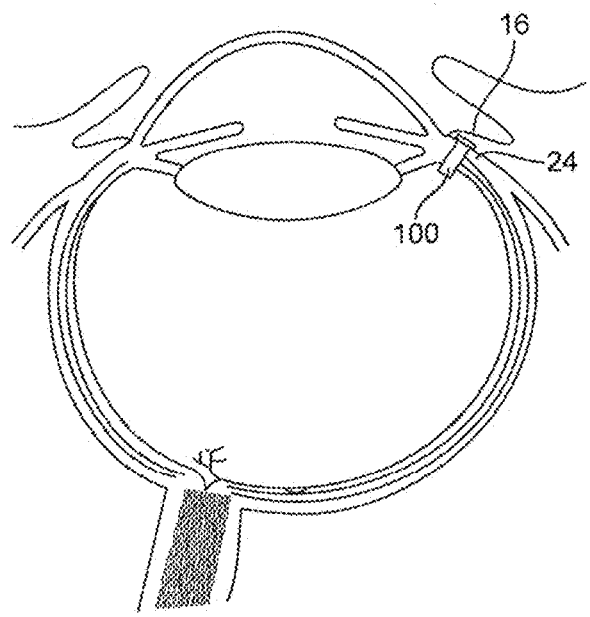
FIG. 1 shows an eye suitable for incorporation of variations of the therapeutic device.

The materials, compounds, compositions, articles, and methods described herein may be understood more readily by reference to the following detailed description of specific aspects of the disclosed subject matter and the Examples included therein. Before the present materials, compounds, compositions, articles, devices, and methods are disclosed and described, it is to be understood that the aspects described below are not limited to specific synthetic methods or specific reagents, as such may vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Therapeutic agent delivery from a diffusion controlled device requires a source of therapeutic agent with a dissolved therapeutic agent concentration higher in energy than the therapeutic agent concentration in the target tissue. Delivery of some therapeutic agents is limited by the dissolved therapeutic agent concentration and thermodynamic energy achievable in the source formulation loaded into the device.

It is desirable to deliver therapeutic levels of therapeutic agent for periods of, for example, three months. This is particularly challenging for therapeutic agents with aqueous solubility not much greater than levels needed to be therapeutic in the tissue. For example, target concentrations in the vitreous of about 0.1-10 µg/mL is not achievable from a diffusion controlled therapeutic device implant if the therapeutic agent solubility in aqueous solution is no more than 1-10 µg/mL as is the case for many therapeutic agents, including tyrosine kinase inhibitors.

Furthermore, some formulation approaches increase the amount of therapeutic agent in a formulation that is not in solid form but the formulated entities in solution are large in size and have diffusion rates that are slower than individually dissolved therapeutic agent molecules. For example, several therapeutic agent molecules may associate or self-assemble into a structure such as a micelle, with a size that is an order of magnitude larger than a single therapeutic agent molecule and a diffusion rate that is an order of magnitude slower. Furthermore, the size of the diffusing species increases with time in a reproducible or irreproducible manner, resulting in delivery rate profiles from a diffusion controlled device that drop with time and fail to meet sustained delivery target profiles for extended amounts of time.

The present invention relates a therapeutic agent delivery formulation comprising a therapeutic agent and a complexing agent contained in a reservoir chamber coupled to a porous structure for controlled release of the therapeutic agent at the vitreous of the eye. In some embodiments the therapeutic agent is a compound with poor solubility in water. The compound is in a formulation with a complexing agent. Alternatively, the compound is in a formulation comprising a pH adjusting agent, with or without complexing agents. In further embodiment, the compound is in a formulation comprising amphiphilic agents and/or non-aqueous solvents, with or without complexing agents. The formulations of the current invention are formulated to achieve high concentration (about 1-100 mg/mL) of a therapeutic agent, which is characterized as being not soluble in water or poorly soluble in water.

The present disclosure provides controlled release of a therapeutic agent in complex with a complexing agent from the porous structure which increases the half-life of the therapeutic agent at the vitreous of the eye. According to some embodiments, the therapeutic agent is a tyrosine kinase inhibitor. For example, the tyrosine kinase inhibitor is, without being a limiting example, Sunitinib, Pazopanib, or Axitinib. The concentration of the tyrosine kinase inhibitor in the reservoir is about 1 mg/mL to about 100 mg/mL.

General Definitions

In this specification and in the claims that follow, reference is made to a number of terms, which shall be defined to have the following meanings: All percentages, ratios and proportions herein are by weight, unless otherwise specified. All temperatures are in degrees Celsius (° C.) unless otherwise specified.

By "pharmaceutically acceptable" is meant a material that is not biologically or otherwise undesirable, i.e., the material can be administered to an individual along with the relevant active compound without causing clinically unacceptable biological effects or interacting in a deleterious manner with any of the other components of the pharmaceutical composition in which it is contained.

A weight percent of a component, unless specifically stated to the contrary, is based on the total weight of the formulation or composition in which the component is included.

By "effective amount" as used herein means "an amount of one or more of the disclosed compounds, effective at dosages and for periods of time necessary to achieve the desired or therapeutic result." An effective amount may vary according to factors known in the art, such as the disease state, age, sex, and weight of the human or animal being treated. Although particular dosage regimes may be described in examples herein, a person skilled in the art would appreciate that the dosage regime may be altered to provide optimum therapeutic response. For example, several divided doses may be administered daily or the dose may be proportionally reduced as indicated by the exigencies of the therapeutic situation. In addition, the compositions of this disclosure can be administered as frequently as necessary to achieve a therapeutic amount.

"Agent" is used herein to include any other compound that may be contained in or combined with one or more of the disclosed inhibitors that is not a therapeutically or biologically active compound. As such, an agent should be pharmaceutically or biologically acceptable or relevant (for example, an agent should generally be non-toxic to the subject). "Agent" includes a single such compound and is also intended to include a plurality of agents. For the purposes of the present disclosure the term "agent" and "carrier" are used interchangeably throughout the description of the present disclosure and said terms are defined herein as, "ingredients which are used in the practice of formulating a safe and effective pharmaceutical composition."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., vascular leakage). It is understood that this is typically in relation to some standard or expected value, in other words it is relative, but that it is not always necessary for the standard or relative value to be referred to.

The term "treat" or other forms of the word such as "treated" or "treatment" is used herein to mean that administration of a therapeutic agent of the present invention mitigates a disease or a disorder in a host and/or reduces, inhibits, or eliminates a particular characteristic or event associated with a disorder (e.g., vascular leakage).

Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

The term "ameliorating a symptom" or other forms of the word such as "ameliorate a symptom" is used herein to mean that administration of a therapeutic agent of the present invention mitigates one or more symptoms of a disease or a disorder in a host and/or reduces, inhibits, or eliminates a particular symptom associated with the disease or disorder prior to and/or post administration of the therapeutic agent.

The disclosed compounds affect vascular leakage by inhibiting a receptor tyrosine kinase.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if a range of 10 and 15 is disclosed, then 11, 12, 13, and 14 are also disclosed.

The phrase "pharmaceutically acceptable salt(s)," as used herein, unless otherwise indicated, includes salts of acidic or basic groups.

The term "kinase" refers to any enzyme that catalyzes the addition of phosphate groups to a protein residue; for example, serine and threonine kinases catalyze the addition of phosphate groups to serine and threonine residues.

The terms "VEGFR kinase," "VEGFR," refer to any of the vascular endothelial growth factor receptors.

The terms "VEGF signaling," and "VEGF cascade" refer to both the upstream and downstream components of the VEGF signaling cascade.

The term "pharmaceutically acceptable" refers to the fact that the carrier, diluent or agent must be compatible with the other ingredients of the formulation and not deleterious to the recipient thereof.

The terms "administration of a compound" or "administering a compound" refer to the act of providing a compound of the invention or pharmaceutical composition to the subject in need of treatment.

In the current disclosure "composition" and "formulation" are used interchangeably and refer to the conventional understanding, as known in the art, of a composition or formulation. "Formulation" as disclosed herein may comprise a solution, suspension, semi-solid, or semi-liquid mixtures of therapeutic agents and/or formulation excipients or formulation agents.

"Solution" according to the current invention is a clear, homogeneous liquid form that contains one or more chemical substances dissolved in a solvent or mixture of mutually miscible solvents. A solution is a liquid preparation that contains one or more dissolved chemical substances in a suitable solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" according to the current invention is a liquid form that contains solid particles dispersed in a liquid vehicle. "Suspension" as disclosed herein contemplates any variations based on the current state of the art or variations achieved by one skilled in the art.

"Therapeutic agent delivery device" and "Port Delivery System" ("PDS") are used interchangeably in this specification. As disclosed herein, the "Therapeutic agent delivery device" or "Port Delivery System" ("PDS") contemplates any variation of the disclosed device designed to achieve similar objective of target specific delivering a therapeutic agent into a subject. For example, "Therapeutic agent delivery device" or "Port Delivery System" ("PDS") may have a design to include a membrane, an opening, a diffusion barrier, a diffusion mechanism so as to release therapeutic amounts of therapeutic agent for extended periods of time, e.g., 30 days, 60 days, 90 days, 120 days or more. Several variations of the device have been disclosed in WO 2012/065006, WO2012/019047, WO2013/003620, WO 2012/019136, WO 2012/019176, and U.S. Pat. No. 8,277,830, each of which is incorporated by reference herein in its entirety.

Therapeutic Agents

Therapeutic agents of the present invention may be compounds with poor solubility in water. Solubility of the therapeutic agents in water or an aqueous solvent may vary from being sparingly soluble (parts of solvent required for 1 part of solute being 30 to 100), slightly soluble (parts of solvent required for 1 part of solute being 100 to 1000), very slightly soluble (parts of solvent required for 1 part of solute being 1000 to 10,000), and practically insoluble or insoluble ($\geq$10,000). Therapeutic agents of the present invention may be a poor or low water soluble compound. As referred to herein, a poor or low water soluble compound may have a solubility of, for example, less than 1 mg/mL or less than 0.01 mg/mL.

In some embodiments, the therapeutic agents are receptor tyrosine kinase inhibitors. Suitable inhibitors are various inhibitors that inhibit one or more of the following receptors: VEGFR1, VEGFR2, VEGFR3, PDGFRα, PDGFRβ, c-kit, and/or FGFR. In some embodiments the therapeutic agents have the characteristics as shown in Table 1.

TABLE 1

| Therapeutic agent Compound | Structure and Property |
|---|---|
| Sunitinib | Butanedioic acid, hydroxy-, (2S)-, compound with N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide (1:1)<br>Molecular structure:<br>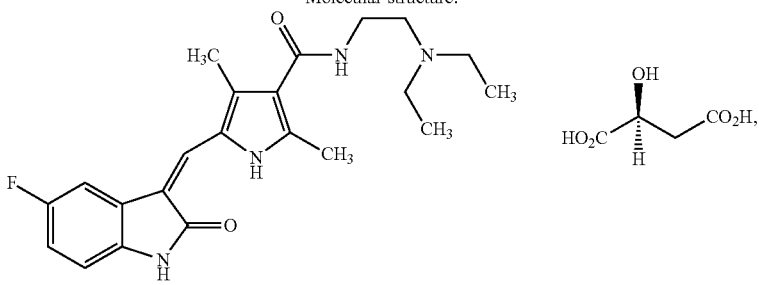<br>(Formula I)<br>or a pharmaceutically acceptable salt thereof.<br>Molecular formula: $C_{22}H_{27}FN_4O_2 \cdot C_4H_6O_5$<br>Molecular weight: 532.6 Daltons. |
| Pazopanib | 5-[[4-[(2,3-dimethyl-2H-indazol-6-yl)methylamino]-2-pyrimidinyl]amino]-2-methylbenzenesulfonamide monohydrochloride.<br>Molecular structure:<br>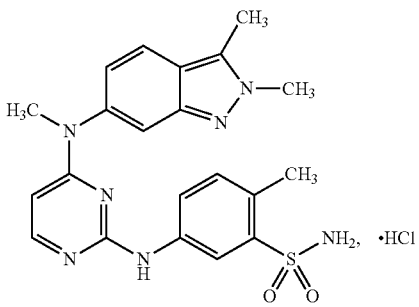<br>(Formula II)<br>or a pharmaceutically acceptable salt thereof.<br>Molecular formula $C_{21}H_{23}N_7O_2S \cdot HCl$<br>Molecular weight of 473.99 Dalton. |
| Linifanib | N-[4-(3-Amino-1H-indazol-4-yl)phenyl]-N'-(2-fluoro-5-methylphenyl)urea<br>Molecular structure<br>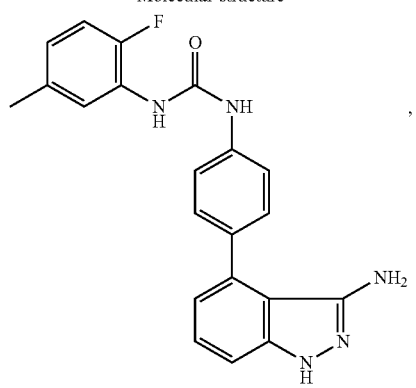<br>(Formula III)<br>or a pharmaceutically acceptable salt thereof.<br>Molecular formula: $C_{21}H_{18}FN_5O$<br>Molecular weight: 375.40 |

TABLE 1-continued

| Therapeutic agent Compound | Structure and Property |
|---|---|
| Motesanib | AMG 706; N-(2,3-Dihydro-3,3-dimethyl-1H-indol-6-yl)-2-[(4-pyridinylmethyl)amino]-3-pyridinecarboxamide<br>Molecular Structure<br>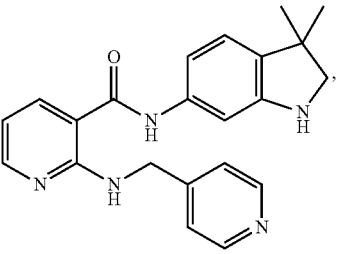<br>(Formula IV)<br>or a pharmaceutically acceptable salt thereof<br>Molecular formula: $C_{22}H_{23}N_5O$<br>Molecular weight: 373.45 |
| Axitinib | N-Methyl-2-((3-((1E)-2-(pyridin-2-yl)ethenyl)-1H-indazol-6-yl)sulfanyl)benzamide<br>Molecular structure<br>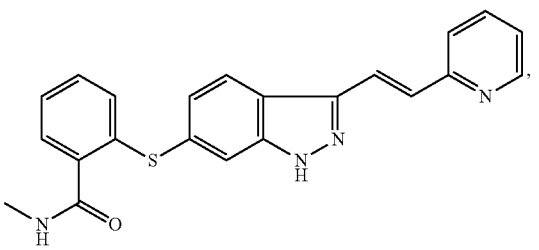<br>(Formula V)<br>or a pharmaceutically acceptable salt thereof.<br>Molecular formula: $C_{22}H_{18}N_4OS$<br>Molecular weight: 386.47 |
| Sorafenib | 4-[4-[[4-Chloro-3-(trifluoromethyl)phenyl]carbamoylamino]phenoxy]-N-methyl-pyridine-2-carboxamide<br>Molecular structure<br>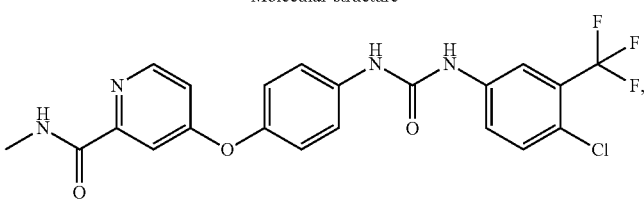<br>(Formula VI)<br>or a pharmaceutically acceptable salt thereof.<br>Molecular formula: $C_{21}H_{16}ClF_3N_4O_3$<br>Molecular weight 464.83 |

The current embodiments provide the therapeutic agent in a formulation with formulating agents. The formulating agents of the current embodiments are complexing agents, stabilizing agents, solubilizing agents, pH adjusting agents, buffering agents, amphiphilic agents, tonicity agents, or any combinations thereof.

Therapeutic Device

Device Performance

The therapeutic device comprises many configurations and physical attributes, for example the physical characteristics of the therapeutic device comprise at least one of a therapeutic agent delivery device (Port Delivery System (PDS)) with a suture, positioning and sizing such that vision is not impaired, and biocompatible material. For example, the device comprises a reservoir capacity from about 0.005 cc to about 0.2 cc, for example from about 0.01 cc to about 0.1 cc, and a device volume of no more than about 2 cc. A vitrectomy is performed for device volumes larger than 0.1 cc. The length of the therapeutic device does not interfere with the patient's vision and is dependent on the shape of the device, as well as the location of the implanted device with respect to the eye. The length of the device also depends on the angle in which the device is inserted. For example, a length of the device comprises from about 4 to 6 mm. Since the diameter of the eye is about 24 mm, a device extending no more than about 6 mm from the sclera into the vitreous has a minimal effect on patient vision.

Variations comprise many combinations of implanted therapeutic agent delivery devices (Port Delivery System (PDS)). The therapeutic device comprises a therapeutic agent and binding agent. The device also comprises at least one of a membrane, an opening, a diffusion barrier, a diffusion mechanism so as to release therapeutic amounts of therapeutic agent for the extended time. Several variations of the device have been disclosed in WO 2012/065006, WO2012/019047, WO2013/003620, WO 2012/019136, WO 2012/019176, and U.S. Pat. No. 8,277,830, each of which is incorporated by reference herein in its entirety.

Figures 1, 1A:
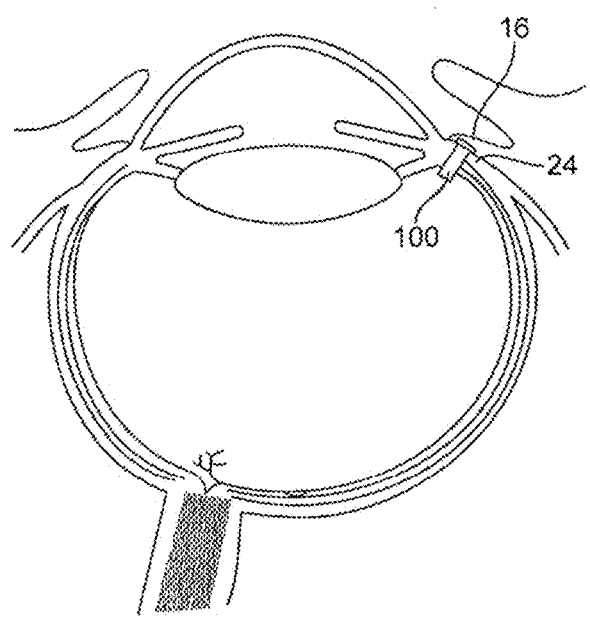
Figures 1, 1A:
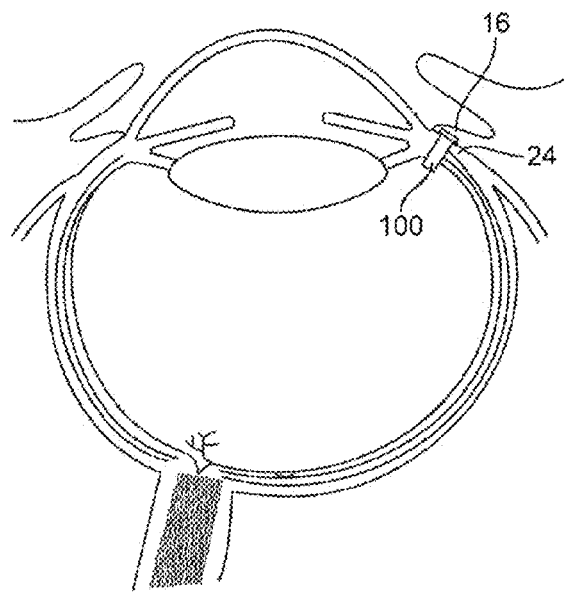

FIG. 1A-1 shows a therapeutic device 100 implanted at least partially within the sclera 24 of the eye 10 as in FIG. 1. In some embodiments, the therapeutic device comprises a retention structure, for example a protrusion, to couple the device to the sclera. The therapeutic device extends through the sclera into vitreous humor 30, such that the therapeutic device releases the therapeutic agent into the vitreous humor.

Figures 1, 1A, 2:
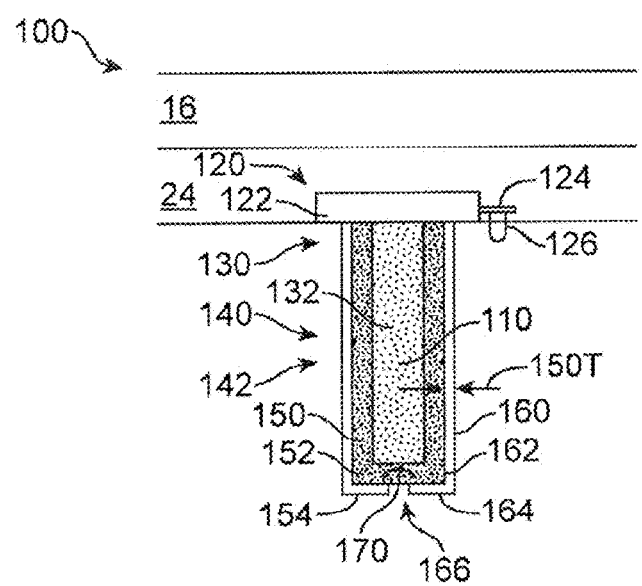
Figures 1, 1A, 2:
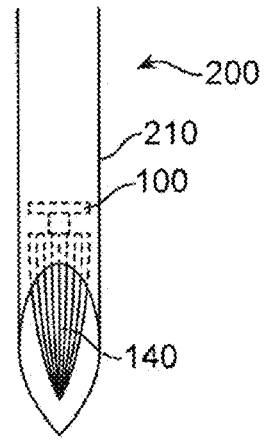
Figures 1, 1A, 2:
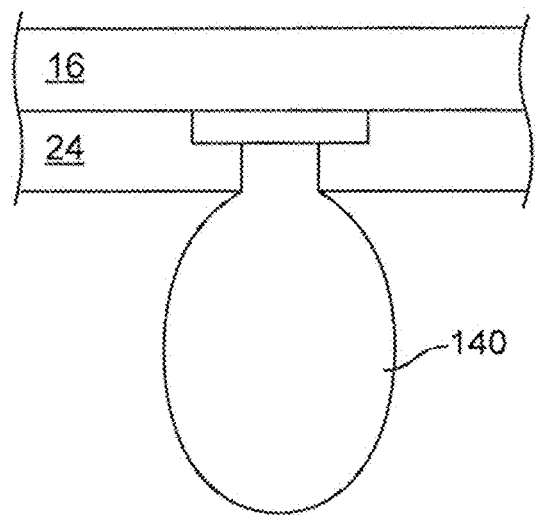

FIGS. 1A-1-1 and 1A-1-2 show a therapeutic device 100 implanted under the conjunctiva 16 and extending through the sclera 24 to release a therapeutic agent 110 into vitreous humor 30 of the eye 10 so as to treat the retina of the eye. The therapeutic device 100 comprises a retention structure 120 such as a smooth protrusion configured for placement along the sclera and under the conjunctiva, such that the conjunctiva covers the therapeutic device and protects the therapeutic device 100. When the therapeutic agent 110 is inserted into the device 100, the conjunctiva is lifted away, incised, or punctured with a needle to access the therapeutic device. The eye comprises an insertion of the tendon 27 of the superior rectus muscle to couple the sclera of the eye to the superior rectus muscle. In some embodiments, the device 100 is positioned in many locations of the pars plana region, for example away from tendon 27 and one or more of posterior to the tendon, under the tendon, or with nasal or temporal placement of the therapeutic device.

While the implant can be positioned in the eye in many ways, work in relation to variations suggests that placement in the pars plana region releases therapeutic agent into the vitreous to treat the retina, for example therapeutic agent comprising an active ingredient composed of large molecules.

Therapeutic agents 110 suitable for use with device 100 include many therapeutic agents, for example as listed in Table 1. The therapeutic agent 110 of device 100 comprises one or more of an active ingredient of the therapeutic agent, a formulation of the therapeutic agent, components of a formulation of the therapeutic agent, a physician prepared formulation of therapeutic agent, or a pharmacist prepared formulation of the therapeutic agent. The therapeutic agent is referred to with generic name or a trademark, for example as shown in Table 1.

The therapeutic device 100 can be implanted in the eye to treat the eye for as long as is helpful and beneficial to the patient. For example, the device is implanted for at least about 5 years, such as permanently for the life of the patient. Alternatively or in combination, the device is removed when no longer helpful or beneficial for treatment of the patient.

FIG. 1A-2 shows structures of therapeutic device 100 configured for placement in an eye as in FIGS. 1A-1, 1A-1-1 and 1A-1-2. The device comprises retention structure 120 to couple the device 100 to the sclera, for example a protrusion disposed on a proximal end of the device. The device 100 comprises a container 130 affixed to the retention structure 120. An active ingredient, for example therapeutic agent 110, is contained within a reservoir 140, for example a chamber 132 defined by a container 130 of the device. The container 130 comprises a porous structure 150 comprising a porous material 152, for example a porous glass frit 154, and a barrier 160 to inhibit release of the therapeutic agent, for example non-permeable membrane 162. The non-permeable membrane 162 comprises a substantially non-permeable material 164. The non-permeable membrane 162 comprises an opening 166 sized to release therapeutic amounts of the therapeutic agent 110 for the extended time. The porous structure 150 comprises a thickness 150T and pore sizes configured in conjunction with the opening 166 so as to release therapeutic amounts of the therapeutic agent for the extended time. The container 130 comprises reservoir 140 having a chamber with a volume 142 sized to contain a therapeutic quantity of the therapeutic agent 110 for release over the extended time. The device comprises a needle stop 170. Proteins in the vitreous humor enter the device and compete for adsorption sites on the porous structure and thereby contribute to the release of therapeutic agent. The therapeutic agent 110 contained in the reservoir 140 equilibrate with proteins in the vitreous humor, such that the system is driven towards equilibrium and the therapeutic agent 110 is released in therapeutic amounts.

The non-permeable material such as the non-permeable membrane 162, the porous material 152, the reservoir 140, and the retention structure 120, comprise many configurations to deliver the therapeutic agent 110. The non-permeable membrane 162 comprises an annular tube joined by a disc having at least one opening formed thereon to release the therapeutic agent. The porous material 152 comprises an annular porous glass frit 154 and a circular end disposed thereon. The reservoir 140 is shape-changing for ease of insertion; i.e., it assumes a thin elongated shape during insertion through the sclera and then assumes an extended, ballooned shape, once it is filled with therapeutic agent.

The porous structure 150 can be configured in many ways to release the therapeutic agent in accordance with an intended release profile. The porous structure comprises a single hole or a plurality of holes extending through a barrier material such as a rigid plastic or a metal. Alternatively or in combination, the porous structure comprises a porous structure having a plurality of openings on a first side facing the reservoir and a plurality of openings on a second side facing the vitreous humor, with a plurality of interconnecting channels disposed there between so as to couple the openings of the first side with the openings of the second side, for example a sintered rigid material. The porous structure 150 comprises one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

FIG. 1A-2-1 shows therapeutic device 100 loaded into an insertion cannula 210 of an insertion apparatus 200, in which the device 100 comprises an elongate narrow shape for insertion into the sclera, and in which the device is configured to expand to a second elongate wide shape for retention at least partially in the sclera.

FIG. 1A-2-2 shows a therapeutic device 100 comprising reservoir 140 suitable for loading in a cannula, in which the reservoir 140 comprises an expanded configuration when placed in the eye.

Figure 1B:
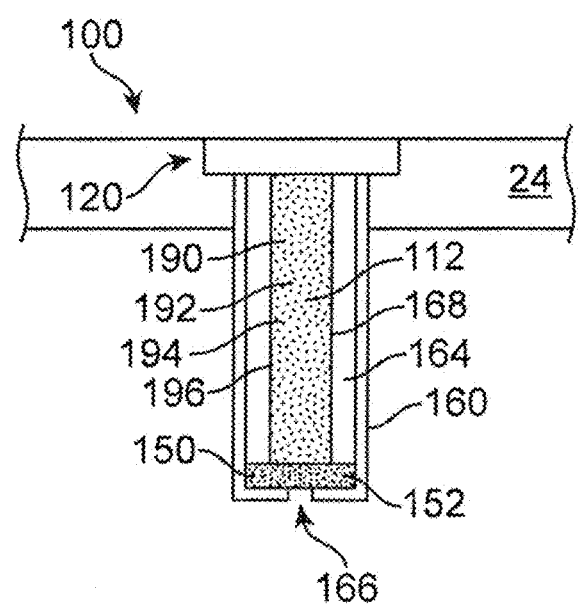
FIG. 1B shows a therapeutic device configured for placement in an eye as in FIGS. 1A-1 and 1A-1-1, in accordance with variations described herein.
Figure 2:
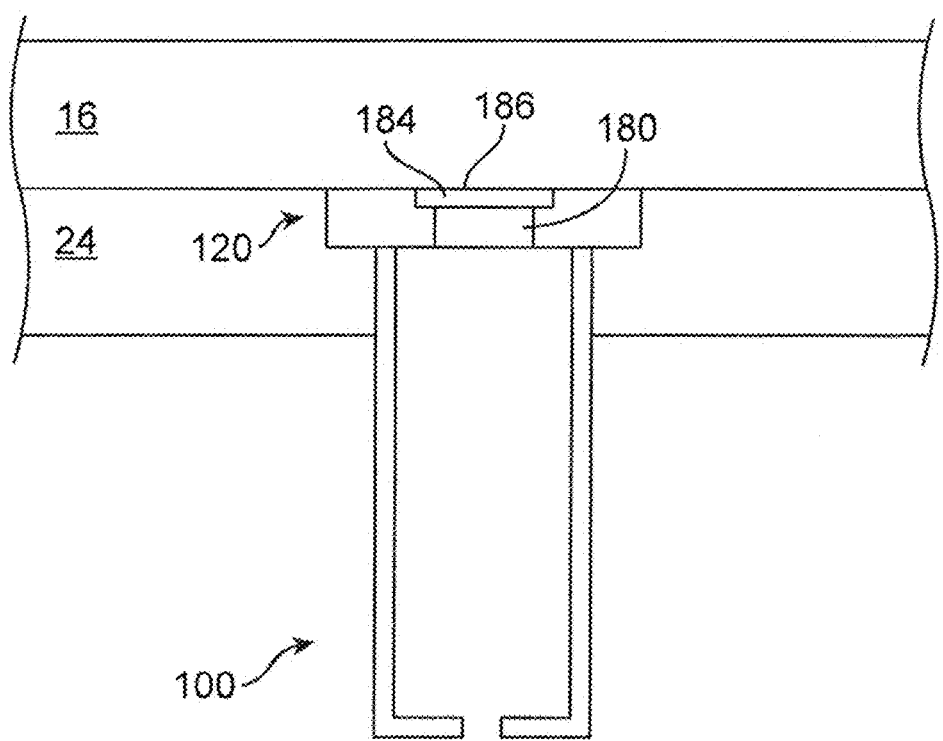

FIG. 1B shows therapeutic device 100 placed in an eye as in FIGS. 1A-1 and 1A-1-1. The device comprises retention structure 120 to couple to the sclera, for example flush with the sclera, and the barrier 160 comprises a tube 168. An active ingredient 112 comprising the therapeutic agent 110 is contained within tube 168 comprising non-permeable material 164. A porous structure 150 comprising a porous material 152 is disposed at the distal end of the tube 168 to provide a sustained release of the therapeutic agent at therapeutic concentrations for the extended period. The non-permeable material 164 extends distally around the porous material 152 so as to define an opening to couple the porous material 152 to the vitreous humor when the device is inserted into the eye.

FIG. 2 shows an access port 180 suitable for incorporation with the therapeutic device 100. The access port 180 is combined with the therapeutic devices described herein. The access port is disposed on a proximal end of the device. The access port 180 comprises an opening formed in the retention structure 120 with a penetrable barrier 184 comprising a septum 186 disposed thereon. The penetrable barrier receives the needle 189 sized to pass the formulation 190 as described herein. The access port 180 is configured for placement under the conjunctiva 16 of the patient and above the sclera 24.

Formulation

The embodiments of the current invention provide formulations of therapeutic agents comprising, for example tyrosine kinase inhibitors, for efficient and sustained intravitreal delivery of the therapeutic agents in the vitreous humor of the eye. A formulation of the current invention comprises a therapeutic agent with low solubility in water, including but without being a limiting example, a tyrosine kinase inhibitor and one or more of: one or more complexing agents, one or more solubilizing/stabilizing/anti-crystalline agents, one or more pH adjusting agents, one or more buffering agents, one or more amphiphilic agent/surfactants, non-aqueous solvents, one or more tonicity adjustment agents. In some embodiments, the tyrosine kinase inhibitor is a receptor tyrosine kinase inhibitor.

The embodiments of the current invention provide a formulation of receptor tyrosine kinase inhibitors, for example, without being limiting, selected from the compounds/agents listed in Table 1 herein. In one embodiment, the therapeutic agent may be Sunitinib or Sunitinib malate (Formula I). In another embodiment of the current invention the therapeutic agent may be Pazopanib or Pazopanib hydrochloride (Formula II). In yet another embodiment of the current invention the therapeutic agent may be Axitinib (Formula V).

The formulations of the current invention comprise Sunitinib or Sunitinib malate, Pazopanib or Pazopanib hydrochloride, or Axitinib associated with a complexing agent, selected from, without being limiting to the list herein, 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, and combinations thereof.

In some embodiments, complexing agents, such as cyclodextrins, which do not cross biological membranes easily and do not affect the PK properties of the therapeutic agents, are used to increase the aqueous concentration of the agent in the reservoir of the therapeutic device of the current invention. Complexing agents, e.g., cyclodextrin formulations, of the present disclosure, increase the concentration of dissolved therapeutic agent up to 800,000 fold, as high as 10 to 100 mg/mL for therapeutic agents with aqueous solubility of 10 mg/mL or less, e.g., therapeutic agents with aqueous solubility of 0.1 μg/mL or less.

The increase in the concentration of the therapeutic agent in the device is about 100× higher than the concentration required at the vitreous for effective treatment, prevention of progression, or amelioration of vascular leakage and neovascularization (NV) in the retina. Because the required concentration at the vitreous for effective treatment, prevention of progression, or amelioration of vascular leakage and neovascularization (NV) is higher than the solubility limit of the therapeutic agent, the embodiments of the current invention provide increased therapeutic agent solubility of about or more than 1000× the inherent aqueous solubility of the agent.

In some embodiments the complexing agent is sulfobutyl ether-β-cyclodextrin ("SBEβCD") or CAPTISOL®. The formulations intravitreal delivery of the current invention comprises therapeutic agent Sunitinib or Sunitinib malate, Pazopanib or Pazopanib hydrochloride, or Axitinib in a complex with CAPTISOL®. Association of therapeutic agent Sunitinib or Sunitinib malate, Pazopanib or Pazopanib hydrochloride, or Axitinib with CAPTISOL® increases aqueous solubility of the agent by a factor of 10 to 25,000, depending on the therapeutic agent. Interaction of therapeutic agent Sunitinib or Sunitinib malate, Pazopanib or Pazopanib hydrochloride, or Axitinib with CAPTISOL® provides a beneficial and protected environment for the therapeutic agent in the lipophilic cavity of CAPTISOL®, while the hydrophobic surface of CAPTISOL® provides effective water solubility, thereby boosting both solubility and stability of the therapeutic agent. Furthermore, interaction of the therapeutic agents with CAPTISOL® reduces decomposition of the agent by protecting labile regions from the potential reactants in the aqueous environment.

In an embodiment of the invention, the ratio of the complexing agent, for example, cyclodextrin ("CD"; 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, and combinations thereof) to a therapeutic agent is about 9:1, 8:1, 7:1, 6:1, 5:1, 4:1, 3:1, or 2:1. In an embodiment, the ratio of CD:therapeutic agent is about 2.5:1. In yet other embodiments the CD:therapeutic agent ratio is 2.2:1; 2.5:1; 3.7:1; 5:1; 8:1; or 9:1.

In one embodiment, the ratio of hydroxypropyl β-cyclodextrin or CAPTISOL®: Sunitinib (CD:therapeutic agent) in the formulation is about 2.5:1 or 4:1. In another embodiment, the ratio of hydroxypropyl β-cyclodextrin or CAPTISOL®: Pazopanib (CD: therapeutic agent) in the formulation is about 2:1 or 4:1. In yet another embodiment, the ratio for hydroxypropyl β-cyclodextrin or CAPTISOL®: Axitinib (CD:therapeutic agent) in the formulation is about 2.5:1 or 4:1.

In yet another embodiment, the formulation has a therapeutic agent and either CAPTISOL® or HPβCD, further in combination any one or more of: Histidine, PVP, and citric acid. Additional components of the formulation: trehalose, methylcellulose, ethylcellulose, sodium carboxymethylcellulose, hydroxypropylmethylcellulose, sodium hyaluronate, sodium alginate, chitosan and its derivatives, polyethylene glycol, glycerin, propylene glycol, Triacetin, N,N-Dimethylacetamide, poly(vinyl pyrrolidone), pyrrolidone, dimethyl sulfoxide, ethanol, N-(-beta-Hydroxyethyl)-lactamide, 1-Methyl-2-pyrrolidinone, triglycerides, monothioglycerol, sorbitol, lecithin, methylparaben, propylparaben, polysorbates, block copolymers of ethylene oxide and propylene oxide, di-block polymers or tri-block copolymers of polyethylene oxide and polypropylene oxide, ethoxylated emulsifiers, polyethylene glycol esters, sucrose laurate, Tocopherol-PEG-succinate, phospholipids and their derivatives, or other non-ionic self-emulsifying agents.

In some embodiments, the formulation comprises CAPTISOL® as the complexing agent. The concentration of the therapeutic agent in the presence of CAPTISOL® is between 0.5 mg/mL to about 90 mg/mL. For example, the concentration of Pazopanib in the presence of CAPTISOL® is about 20 mg/mL, 50 mg/mL, or 90 mg/mL; concentration of Sunitinib in the presence of CAPTISOL® is about 20-30 mg/mL; concentration of Axitinib in the presence of CAPTISOL® is about 5 mg/mL; concentration of Linifanib in the presence of CAPTISOL® is about 6 mg/mL; and concentration of Motesanib in the presence of CAPTISOL® is about 30 mg/mL.

In additional embodiments, therapeutic agent is in a formulation lacking any complexing agent. The solubility of the therapeutic agent in such a formulation is increased with a pH adjusting agent. In yet another embodiment the solubility of the therapeutic agent is increased with amphiphilic agents and non-aqueous solvents.

In another embodiment, the formulation of the current invention comprises hydroxypropyl β-cyclodextrin ("HP-β-CD") as a complexing agent. For example, the concentration of the therapeutic agent in the presence of HP-β-CD is between 10 mg/mL to about 40 mg/mL. For example, the concentration of Pazopanib in the presence of HP-β-CD is about 20 mg/mL. For example, the concentration of Sunitinib in the presence of HP-β-CD is about 30 mg/mL.

Hydrophilic stabilizing/solubilizing/anti-crystalline agents in the formulation of the current invention include, without being a limiting example, trehalose, methylcellulose, ethylcellulose, sodium carboxymethylcellulose, sodium hyaluronate, sodium alginate, polyethylene glycol, glycerin, propylene glycol, Triacetin, N,N-Dimethylacetamide, poly(vinyl pyrrolidone), pyrrolidone, or combinations thereof.

In one embodiment, the stabilizing/solubilizing agent is poly(vinyl pyrrolidone) (PVP). For example, the formulation of the current invention comprises between 0.2% to 1% PVP. In some embodiments, the formulation comprises between 5 mg/mL PVP to about 30 mg/mL PVP. For example, the Sunitinib formulation comprises, about 30-40 mg/mL Sunitinib malate, about 300-400 mg/mL of complexing agent (e.g., SBEβCD), and about 5 mg/mL or about 30 mg/mL of PVP. For example, the Axitinib formulation of the current invention comprises about 6 mg/mL of Axitinib, about 200-300 mg/mL of complexing agent (e.g., SBEβCD), and optionally about 10 mg/mL of PVP. In another embodiment, the Pazopanib formulation of the current invention comprises about 20 mg/mL Pazopanib or about 45-55 mg/mL Pazopanib, about 320 mg/mL (e.g., HPβCD) or about 1000 mg/mL (e.g., SBEβCD) of complexing agent, and optionally about 2 mg/mL of PVP.

In one embodiment, the formulation comprises the stabilizing/solubilizing agents, but no complexing agents. The formulation comprises agents which are characterized as being either stabilizing or solubilizing or both. In some embodiments, the solubilizing and/or stabilizing agents prevent precipitation of the therapeutic agent, and are characterized as an anti-crystalizing agent.

The formulation of the current invention includes one or two agents for pH adjustment for increasing buffering capacity of the formulation in the therapeutic device. One or two pH adjustment agents is/are selected from, without being a limiting example, sodium hydroxide, hydrochloric acid, citric acid, malic acid, acetate, tartaric acid, histidine, phosphate, or combinations thereof. In one embodiment, the formulation comprises agents for pH adjustment, but no complexing agents.

In one embodiment, the one or two pH adjusting agents are citric acid and/or histidine.

The formulation of the current invention includes a tonicity adjusting agent. For example, the tonicity adjusting agent is, without being a limiting example, sodium chloride, sodium phosphate, or combinations thereof.

In some embodiments, formulations of high concentrations are produced for therapeutic agents with poor aqueous solubility. The current embodiments provide that the high concentration formulations of therapeutic agents, which have low solubility in aqueous solutions, are compatible with the physiological conditions of the vitreous upon therapeutic agent delivery. For example, in one embodiment a high concentration formulation of Pazopanib is produced. Pazopanib is insoluble in phosphate buffered saline at neutral pH, and has solubility of 0.1 μg/mL in aqueous solutions with 0.1% polysorbate-20. The current embodiments provide a formulation of 80 mg/mL (800,000-fold increase) of Pazopanib, which is formulated at pH 7, where the formulation includes one or more complexing agents and additional agents.

In another embodiment, a high concentration formulation of Axitinib is produced. Axitinib at 0.3 μg/mL concentration has poor solubility in PBS. In one embodiment, a formulation of 6 mg/mL (20,000-fold increase) Axitinib may be produced at pH 7 with use of complexing agents and other agents.

The formulations of the current invention have high stability during the use time of the PDS implant. For example, formulations are stable in the PDS reservoir chamber at 37° C. at physiological conditions for at least 6 months. For example, the formulations are stable in the PDS in the presence of vitreous components diffusing from the vitreous.

Target Specificity and Concentration at Delivery Site

Target specificity is measured based on the biochemical kinase inhibition assays as the first approximation. To estimate the in-vivo targets, biological barriers (protein binding, melanin binding), in-vivo efficacy, PK/PD and toxicity for the intended route of administration are evaluated. Ki×100 is used as an estimate for the vitreous levels of the therapeutic agent. In one embodiment, inhibition assays performed for several of the therapeutic agents showed specific inhibition of VEGFR2. See Table 2.

TABLE 2

| Biochemical Ki | Sunitinib | Pazopanib | Axitinib | Linifanib | Motesanib | Sorafenib |
|---|---|---|---|---|---|---|
| TARGET Ki, nM | | | | | | |
| VEGFR2 (KDR) | 1.5 | 14 | 0.1 | 8.1 | 26 | 59 |
| Off-target Ki, nM | | | | | | |
| FGF1 | 520 | 990 | 48 | 12500 | 6200 | |
| RET | 12 | 310 | 1900 | 100 | 14 | 13 |
| Ratio estimate (Ki, off-target)/(Ki, target) | 8 | 22 | 476 | 12 | 0.5 | 0.2 |

Formulation Development

The embodiments of the current invention provide design of a therapeutic agent formulation, for example, tyrosine kinase inhibitor formulation useful for intravitreal delivery of the therapeutic agent from a therapeutic device. The formulation of the current invention provides high aqueous solubility for therapeutic agents, which are characterized as having low solubility at physiological pH. The solubility is increased up to approximately between 1000-800,000 fold.

In some embodiments, the solubility of the therapeutic agent in a formulation is increased by lowering pH of the formulation. The solubility of the therapeutic agent in a formulation is increased by complexing the therapeutic agent with one or more complexing agents, which also increases stability of the therapeutic agent. For example, the therapeutic agent formulation also includes non-ionic agent to increase solubility of the agent.

Present disclosure provides formulations prepared by a standard method in the art. For example, the formulations are prepared following the method described in US 20130023550, or a modified method thereof.

Figure 3:
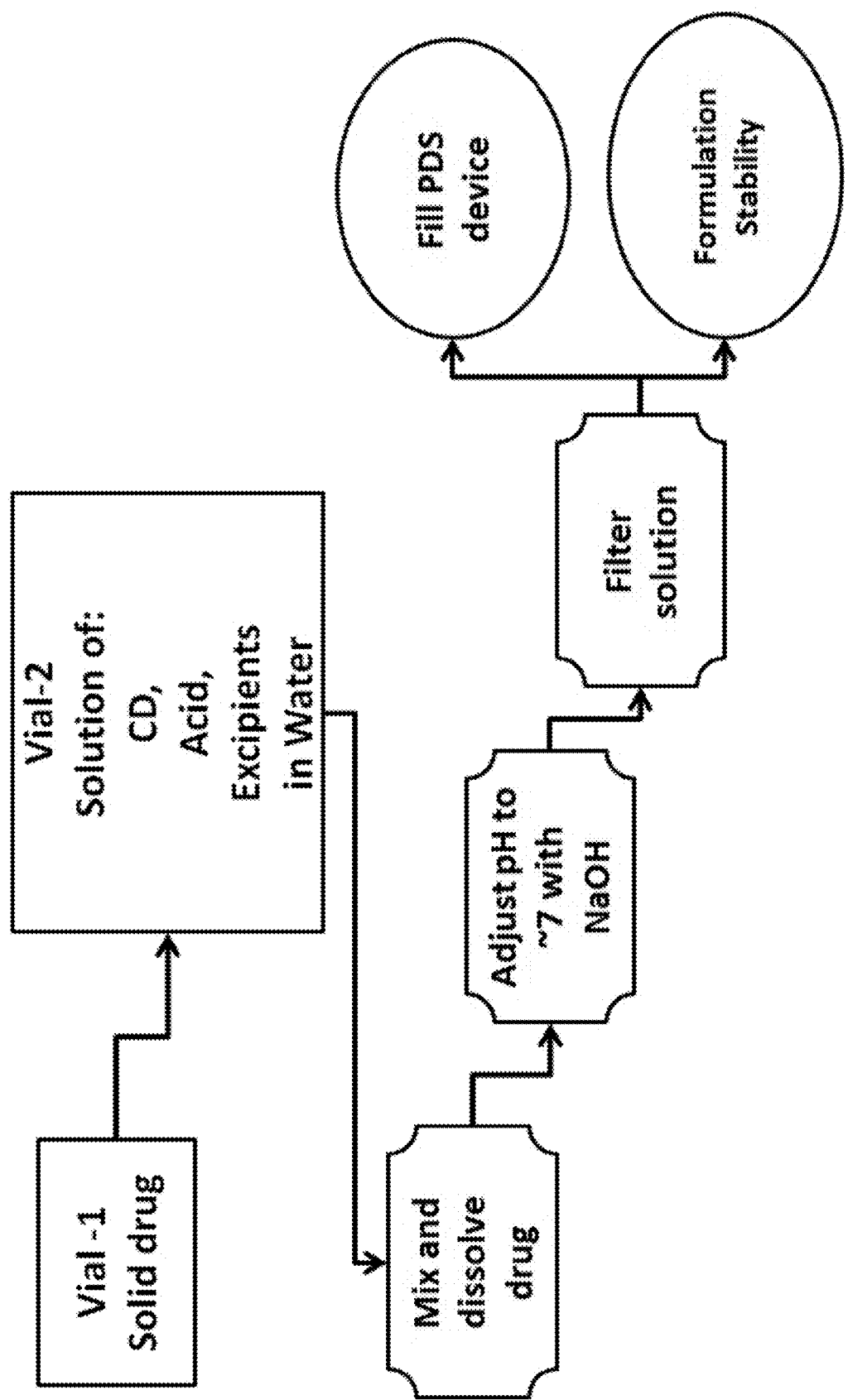
FIG. 3 shows a schematic of the formulation preparation for delivering the therapeutic agent (therapeutic agent) to the vitreous of the eye and for determining stability of the agent in the formulation.
Figure 4:
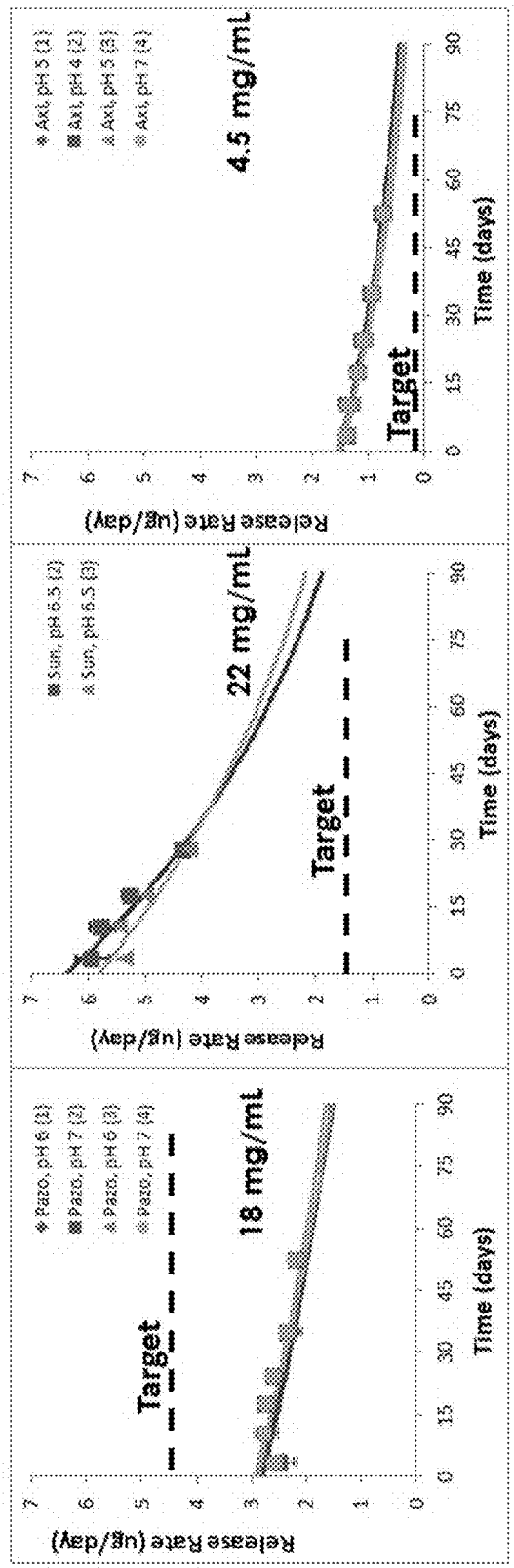
FIG. 4A-C shows comparative line graphs of the release rate as a function of time (days) for Pazopanib (5A), Sunitinib (5B), and Axitinib (5C), in the presence of HPβCD or CAPTISOL® and under different pH values of the formulation.

The formulations of the current invention are provided by transferring therapeutic agents from Vial-1 in solid form to a solution of a complexing agent, a buffering agent, and one or more agents in Vial-2. See FIG. 3. The therapeutic agent is then mixed and dissolved in the solution in Vial-2. The pH of the solution is adjusted with an agent for pH adjustment. The solution containing the therapeutic agent in Vial-2 is then filtered and transferred to a therapeutic device or further tested for stability of the formulation.

The complexing agent in Vial-2 of the present disclosure is, without being a limiting example, cyclodextrin ("CD"; 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, and combinations thereof). The CD in the formulation is present at a ratio to a therapeutic agent of about 9:1, 8:1, 7:1, 6:1, 5:1, 4:1, 3:1, or 2:1. In an embodiment, the ratio of CD:therapeutic agent is about 2.5:1. In yet other embodiments the CD:therapeutic agent ratio is 2.2:1; 2.5:1; 3.7:1; 5:1; 8:1; or 9:1.

In some embodiments, the complexing agent in Vial-2 is β-cyclodextrin sulfobutyl ether. The β-cyclodextrin sulfobutyl ether in Vial-2 is a sulfobutyl ether derivative of β-cyclodextrin with a range of six to seven sulfobutyl ether groups per cyclodextrin molecule. Vial-2 includes CAPTISOL®, which is a sulfobutyl ether derivative of β-cyclodextrin with a range of six to seven sulfobutyl ether groups per cyclodextrin molecule. Solid form of a therapeutic agent, for example, Sunitinib or Sunitinib malate, Pazopanib or Pazopanib hydrochloride, or Axitinib in Vial-1 is transferred to the Vial-2 for complexing with CAPTISOL® to develop the formulation of the current invention.

The concentration of the therapeutic agent in Vial-2 solution is between about 5 mg/mL to 80 mg/mL. For example, in some embodiments, the concentration of the therapeutic agent in the presence of CAPTISOL® is between 5 mg/mL to about 80 mg/mL. The concentration of Pazopanib in the presence of CAPTISOL® is about 20 mg/mL, 50 mg/mL, or 80 mg/mL; concentration of Sunitinib in the presence of CAPTISOL® is about 20-30 mg/mL; concentration of Axitinib in the presence of CAPTISOL® is about 5 mg/mL; concentration of Linifanib in the presence of CAPTISOL® is about 6 mg/mL; and concentration of Motesanib in the presence of CAPTISOL® is about 30 mg/mL.

In further embodiments, the solution in Vial-2 of the current invention comprises hydroxypropyl β-cyclodextrin ("HP-β-CD") as a complexing agent. The concentration of Pazopanib in the presence of HP-β-CD is, as a non-limiting example, about 20 mg/mL. The concentration of Sunitinib in the presence of HP-β-CD is, as a non-limiting example, about 30 mg/mL. The concentration of a Pazopanib in the formulation is increased to up to 82 mg/mL. This concentration is achieved, for example, in the presence of histidine and pH 7.0.

The solution in Vial-2 for formulation development of the current invention includes one or more hydrophilic stabilizing/solubilizing agents. Hydrophilic stabilizing/solubilizing agents of the current invention includes, without being a limiting example, trehalose, methylcellulose, ethylcellulose, sodium carboxymethylcellulose, sodium hyaluronate, sodium alginate, polyethylene glycol, glycerin, propylene glycol, Triacetin, N,N-Dimethylacetamide, poly(vinyl pyrrolidone), pyrrolidone, or combinations thereof.

In one embodiment, the stabilizing/solubilizing agent is poly(vinyl pyrrolidone) (PVP).

The solution in Vial-2 for formulation development of the current invention includes one or more agents for pH adjustment ("pH adjusting agent"). The pH adjusting agent in Vial-2 includes, without being a limiting example, one or two agents selected from sodium hydroxide, hydrochloric acid, citric acid, malic acid, acetate, tartaric acid, histidine, phosphate, or combinations thereof. One or two pH adjusting agent in the solution in Vial-2 increases solubility of the therapeutic agent transferred from Vial-1.

In one embodiment, the one or two pH adjusting agents are citric acid and/or histidine.

The pH of the solution in Vial-2 is adjusted between about 4-7 to achieve optimal concentration of the therapeutic agent in solution. An embodiment of the current invention provides adjusting pH of the solution to about 7, to achieve high concentration of a therapeutic agent in the solution. The concentrations is, for example, about 80 mg/mL for Pazopanib at pH 7.0; about 30 mg/mL for Sunitinib at pH 7.0; about 5 mg/mL for Axitinib at pH 7.0; about 6 mg/mL for Linifanib at pH 7.0; and about 30 mg/mL for Motesanib at pH 7.0.

The solution in Vial-2 includes a tonicity adjusting agent. The tonicity adjusting agent is, without being a limiting example, sodium chloride, sodium phosphate, or combinations thereof.

In some embodiments, lower concentration of the therapeutic agent is complexed to 10 μM of cyclodextrin. In one embodiment lower concentrations of therapeutic agent is used in Cell Based Assay Cocktail (10 μM in 0.1% DMSO, 0.1% ethanol, 0.1% polysorbate 20, 5% PEG 400, 100 mM potassium phosphate buffer). In another embodiment, the formulation may further comprise a protein, for example, albumin.

Predicted release rates and vitreous concentrations of tyrosine kinase inhibitors ("TKI"), at 1 month and 3 month after filling a PDS, as a function of the PDS fill concentrations, is listed in Table 3. The values are based on assumptions that fit all six TKIs (Sunitinib, Pazopanib, Axitinib, Linifanib, Motesanib, and Sorafenib) formulated with a complexing agent, e.g., without being a limiting example, CAPTISOL®. The various rates/concentrations in the table represent selections for various TKIs. For example, in some embodiments, 0.5 mg/mL is sufficient to achieve the predicted release rate and vitreous concentration for Axitinib, which has high potency. In contrast, about 128 mg/ml is needed for a TKI with low potency.

Formulation Approaches

Formulations Prepared Under Acidic pH:

The formulations of the current embodiments are generated under acidic pH. In some embodiments increased solubility of therapeutic agents is achieved by lowering pH. For example, Sunitinib 40 mg/mL is solubilized at pH 2-3 without a complexing agent. The solubilized Sunitinib at pH 2-3 is delivered from a PDS reservoir for at least 1 month, or at least 2 months. In some embodiments, the solubilized Sunitinib at pH 2-3 is delivered from a PDS reservoir for over 2 months or for at least over 3 months.

High dissolved concentrations of Sunitinib Malate is obtained by adjusting the pH of the formulation; i.e., without any other agents. The high concentration of therapeutic agent provides buffering capacity that delays pH changes of the formulation in the reservoir.

In one embodiment a solution of Sunitinib Malate is prepared by addition of the compound to solvent, for example to water, followed by addition of hydrochloric acid to yield a clear solution at pH 2 with a final concentration of 41 mg/mL Sunitinib Malate. In another embodiment, Sunitinib Malate is prepared as in a formulation with pH between 3 and 7. For example, the pH of a portion of the solution is adjusted to pH 4 by addition of sodium hydroxide, which yields a solution with final therapeutic agent concentration of about 38 mg/mL Sunitinib Malate. In some embodiments, the pH is adjusted to yield a solution with final therapeutic agent concentration of about 39 mg/mL to about 100 mg/mL.

TABLE 3

| | PDS Fill Conc. | | | | | | | | | |
|---|---|---|---|---|---|---|---|---|---|---|
| | 0.5 mg/mL | | 8 mg/mL | | 40 mg/mL | | 70 mg/mL | | 128 mg/mL | |
| PDS Diffusion Model, | Rate μg/day | Vitreous Conc. μg/mL | Rate μg/day | Vitreous Conc. μg/mL | Rate μg/day | Vitreous Conc. μg/mL | Rate μg/day | Vitreous Conc. μg/mL | Rate μg/day | Vitreous Conc. μg/mL |
| at 1 month | 0.1 | 0.02 | 1.55 | 0.34 | 7.74 | 1.68 | 13.6 | 2.9 | 25 | 5.4 |
| at 3 month | 0.05 | 0.01 | 0.75 | 0.16 | 3.75 | 0.81 | 6.6 | 1.4 | 12 | 2.6 |

According to some embodiments of the current invention, the release rate of the therapeutic agent formulation is between about 25 μg/day to about 0.1 μg/day. The release rate of the therapeutic agent decreases over time from about 10 μg/day on day 1 to about 0.1 μg/day on day 90 or more. For example, the release rate of Pazopanib from the therapeutic device, when associated with HPβCD in a 5:1 ratio in a formulation varies between day 1 and 90, from about 3 μg/day to 1.5 μg/day.

Table 4 lists formulation vitreous concentrations and release rate estimates of six tyrosine kinase inhibitors evaluated in the current invention.

In one embodiment, release rates of up to 5 μg/day are achieved for 1 month for a formulation at pH 2. Release rate of about 2 μg/day is achieved for a formulation at pH 2.

Formulations Prepared in the Presence of Co-Solvents and Solubilizing Agents:

The embodiments of the invention provide increased solubility of the therapeutic agents in the presence of solubilizing agents and co-solvents. In order to increase solubility of the therapeutic agents, formulations of the current embodiments include solubilizing agents, for example, PEG 300, PEG 400, Povidone, Glycerin, Propylene Glycol, Pyrrolidone, Triacetin, N,N-Dimethylacetamide.

TABLE 4

| | Sunitinib | Pazopanib | Axitinib | Linifanib | Motesanib | Sorafenib |
|---|---|---|---|---|---|---|
| Expected Vitreous Conc. at 3 month (Ki × 100), μM | 0.15 | 1.4 | 0.01 | 0.8 | 2.6 | 5.9 |
| Expected Release Rate μg/day | 0.75 | 6.6 | 0.05 | 3.75 | 12 | Not Considered |
| Expected Formulation Concentration | 8 | 70 | 0.5 | 40 | 128 | Not Considered |

Formulations Including Co-Solvents and Solubilizing Agents Combined with Amphiphilic Agents:

The formulations of the current embodiments include amphiphilic agents, for example, Solutol HS 15, CREMOPHOR® (e.g., EL, ELP, RH 40), Poloxamers (e.g., 124, 188, 237, 338, 407), Polysorbates (e.g., Tween 20, Tween 80).

In some embodiments, formulations contain high concentrations (between 1-100 mg/mL) of therapeutic agents in the presence of amphiphilic agents and non-aqueous solvents. These high concentration formulations are loaded into therapeutic devices to release therapeutic agent at high delivery rates. For example, in one embodiment, about 5 mg/mL Pazopanib HCl is dissolvable in 20% Povidone (10K PVP) in water. In another embodiment, 5-100 mg/mL of a suitable a therapeutic agent is dissolved in an appropriate amount of amphiphilic agent.

In an embodiment, a 40-100 mg/mL Pazopanib HCl solution is achieved in neat Glycerin, neat Propylene Glycol, and/or neat Pyrrolidone. In addition, solutions of between 5-39 mg/mL, 40-59 mg/mL, and 60-100 mg/mL Axitinib are prepared in neat DMSO, Pyrrolidone, and/or in any polar organic solvent, e.g., (not being limiting) N,N-Dimethyl acetamide, respectively. Axitinib and Linifanib are formulated in neat PEG 300 at 1-100 mg/mL concentrations. For example, in one embodiment, Axitinib is formulated in neat PEG at 9 mg/mL and Linifanib is formulated in neat PEG at 20 mg/mL concentrations. While formulations in neat solvents are not common, they are useful in a refillable sustained release therapeutic device implant by creating high therapeutic agent concentration solutions in a therapeutic device that slowly releases both therapeutic agent and solvent to the target tissue.

In some embodiments, formulations with high therapeutic agent concentrations are achieved with an ethoxylated emulsifier, e.g., (not being limiting) KOLLIPHOR® HS 15, also known as SOLUTOL® HS 15. A suspension of therapeutic agent is prepared by adding to SOLUTOL® heated in a water bath at 65° C. Phosphate Buffered Saline (PBS) (or any suitable buffer) is added with stirring. Clear solutions with as much as 5 mg/mL Sunitinib Malate, 6 mg/mL Axitinib, and 5 mg/mL Pazopanib HCl, are obtained with final formulation of 30% SOLUTOL® and 70% PBS. In some embodiments, clear solutions of up to 100 mg/mL of therapeutic agent, as a non-limiting example, Sunitinib Malate, Axitinib, and Pazopanib HCl, are prepared in an appropriate percent of SOLUTOL® and appropriate amount of a buffer.

In some embodiments, solutions with as high as 20-100 mg/mL Axitinib is successfully prepared by dissolving about 60 mg/mL or any required amount in a non-aqueous solvent such as, without being a limiting example, Pyrrolidone and then adding agents such as, without being a limiting example, PEG 300 and Polysorbate 80. The final formulation contains additional agents and/or solvents such as, without being a limiting example, 32% Pyrrolidone, 31% PEG 300, 5% Polysorbate 80, and 31% water.

Formulations Prepared in the Presence of Complexing Agents (Cyclodextrins):

In some embodiments, the formulations include beta-cyclodextrin sulfobutylether, sodium salt (CAPTISOL®), hydroxypropyl β-cyclodextrin (HPβCD), hydroxypropyl gamma-cyclodextrin (HPGCD), and/or other chemical derivatives of beta and gamma cyclodextrins.

The current embodiments provide a therapeutic agent in a formulation with a complexing agent, such as, without being a limiting example, a cyclodextrin. In some embodiments, the complexing agent is CAPTISOL®. In yet other embodiments, the complexing agent is HPβCD. For example, in an embodiment, a formulation of the current invention is Pazopanib HCl in CAPTISOL®, with 20.0-100 mg/mL Pazopanib HCl, 5:1 CAPTISOL®. The formulation further comprises appropriate amount of PVP, and has a pH between 4-7.

In yet additional embodiments, a formulation of Pazopanib HCl, in HPβCD is prepared, such as, without being limiting examples:

18.6 mg/mL Pazopanib HCl, 5:1 HPβCD, 0.2% PVP, pH 6

17.7 mg/mL Pazopanib HCl, 5:1 HPβCD, 0.2% PVP, pH 7

17.9 mg/mL Pazopanib HCl, 4:1 HPβCD, 0.2% PVP, pH6

20.2 mg/mL Pazopanib HCl, 4:1 HPβCD, 0.2% PVP, pH 7.

The current embodiments also provide formulations of Sunitinib free base and Sunitinib Malate with CAPTISOL®. In an embodiment, a formulation of Sunitinib Free Base may be prepared, such as, without being a limiting example:

Formulation was 27.3 mg/mL Sunitinib Free Base, 2.5:1 CAPTISOL®, Citric Acid 1:1, pH 6.5

In another embodiment, a formulation of Sunitinib Malate is prepared, such as, without being a limiting example:

Formulation was 24.5 mg/mL Sunitinib Malate, 2.5:1 CAPTISOL®, Citric Acid 1:1, pH 6.5

The current embodiments further provide formulations of Axitinib or Linifanib in CAPTISOL®. The Linifanib formulation is 4.8-20 mg/mL Linifanib, CAPTISOL® at a ratio with Linifanib between 2:1 and 9:1, and pH between pH 4-7. In one embodiment the Linifanib formulation is 4.8 mg/mL Linifanib, 9:1 CAPTISOL®, pH 5.

In another embodiment, the Axitinib formulation is 4.7-100 mg/mL Axitinib, CAPTISOL® at a ratio with Axitinib between 2:1 and 9:1, a pH adjusting agent (such as, without being limiting examples, citric acid, malic acid, histidine), an appropriate solubilizing (anti-precipitating/anti-crystallizing) agent, pH between pH 4-7. In one embodiment, the Axitinib formulation is 4.7 mg/mL, 9:1 CAPTISOL®, citric acid, 1% PVP, at pH 6.

Formulations Comprising Combinations of Complexing Agents and Solubilizing Agents:

The embodiments of the current invention also provide improved formulation solubility, stability, and therapeutic agent release performance by combining one or more complexing agents with other formulation agents listed herein. The reagents for use in the formulations of the current embodiments include acids, as non-limiting examples, citric acid, malic acid, hydrochloric acid, or other acids of the art; buffering agents, as non-limiting examples, phosphates, histidine, or other buffering agents of the art; hydrophilic polymers, as non-limiting examples, povidone (PVP) MW: 4,000 and 10,000, PEG-300 and 400, hydroxypropyl)methyl cellulose, hydroxyethyl-cellulose, poly vinyl alcohol, or other hydrophilic polymers of the art, each polymers at various MWs; surfactants, for example, Tween-20, Tween-80, or other surfactants of the art; and organic solvents, for example, DMSO, ethanol, or other organic solvents of the art. Combinations of the above agents are used to increase solubility, stability, and/or release rate of the therapeutic agents in formulations of the current embodiments. For example, formulation agents for use in the formulations of the current embodiments increase solubility of the therapeutic agent. For example, formulation agents increase solubility of the therapeutic agent in the vitreous by at least one of magnitude, two orders of magnitudes, or three orders of magnitudes over the solubility of the therapeutic agent in phosphate buffered saline.

The embodiments of the current invention further provide drug delivery formulations that contain a therapeutic agent and one or more formulation agents, for example a complexing agent. The formulation is contained in a reservoir chamber coupled to a porous structure of a therapeutic device. Controlled release of the therapeutic agent in the vitreous of the eye is achieved such that the controlled release of the formulation from the porous structure produces a concentration of the therapeutic agent in the vitreous that is lower than the concentration of the therapeutic agent in the reservoir chamber by at least one order of magnitude, two orders of magnitude, or three orders of magnitude. In some embodiments, more than 40%, 50%, 60%, 70%, 80% or 90% of the therapeutic agent in the reservoir chamber is bound to the complexing agent. In other embodiments, less than 60%, 50%, 40%, 30%, 20%, or 10% of the therapeutic agent in the vitreous is bound to the complexing agent.

The embodiments provide extended release or delivery, from a reservoir of a therapeutic device, of therapeutic agents, formulated in the presence of formulation agents, including: one or more complexing agents, one or more pH adjusting agents, one or more buffering agents, one or more solubilizing/stabilizing agents, one or more amphiphilic agents, one or more tonicity agents, or any combination thereof. The delivery or release of the therapeutic agent is extended from few days to few weeks or months. By increasing the concentration of the therapeutic agent with the formulation agents, between 1000-800,000 fold higher than the inherent solubility of the therapeutic agent in an aqueous solution, the stability of the agent is increased in the reservoir and in the vitreous. The formulation also affects release rate of the therapeutic agent, such that the slower release of more stable therapeutic agent extends the time of delivery from few days to weeks or months. In some embodiments, the therapeutic agent is delivered for up to 6 months. In yet other embodiments, the therapeutic agent is delivered for up to 120 days.

The extended delivery of a more stable (with high half-life, as noted in Table 7) and concentrated therapeutic agent (between 1-100 mg/mL) is more efficacious in treating, preventing progression of, and/or ameliorating a symptom of a disease or disorder of the eye.

In some embodiments, the formulation of the therapeutic agent of the current invention is diluted so as to comprise a formulation having an osmolarity and tonicity substantially similar to the osmolarity and tonicity of the vitreous humor, for example within a range from about 280 to about 340, for example about 300 mOsm. While the formulation comprising therapeutic agent, complexing agent, and solubilizing/stabilizing agent, and amphiphilic agent comprises an osmolarity and tonicity substantially similar to the vitreous humor, the formulation comprises a hyper osmotic solution relative to the vitreous humor or a hypo osmotic solution relative to the vitreous humor.

The vitreous humor of the eye comprises an osmolarity of about 290 mOsm to about 320 mOsm. Formulations of therapeutic agent having an osmolarity from about 280 mOsm to about 340 mOsm are substantially isotonic and substantially iso-osmotic with respect to the vitreous humor of the eye. In some embodiments, the formulation of the therapeutic agent injected into the therapeutic device is hypertonic (hyper-osmotic) or hypotonic (hypo-osmotic) with respect to the tonicity and osmolarity of the vitreous. The appropriate reservoir chamber volume and porous structure for a formulation of therapeutic agent disposed in the reservoir chamber are determined so as to release therapeutic amounts of the therapeutic agent for an extended time and to provide therapeutic concentrations of therapeutic agent in the vitreous within a range of therapeutic concentrations that is above the minimum inhibitory concentration for the extended time.

The current embodiments provide formulations comprising various combinations of formulating agents. Non-limiting examples of the formulations of the current invention are listed in Table 5.

TABLE 5

| Formulation | | 1 | 2 | 3 | 4 | 5 | 6 | 7 | 8 | 9 | 10 |
|---|---|---|---|---|---|---|---|---|---|---|---|
| | | | | | | Drug Form Free Base | | | | | |
| | | Pazopanib | | | | Sunitinib | | | | Axitinib | |
| | | | | | | Drug Form | | | | | |
| | | Pazopanib Hydrochloride | | | | Sunitinib Malate | | | | Axitinib Free Base | |
| | | | | | | Drug Concentration | | | | | |
| | | 5-80 mg/mL | 5-100 mg/mL | 5-40 mg/mL | 5-40 mg/mL | 5-50 mg/ml | 5-50 mg/ml | 1-10 mg/ml | 10-50 mg/ml | 2-6 mg/mL | 2-6 mg/mL |
| | | | | | | pH | | | | | |
| | | from 4 to 7 | from 5 to 7.5 | from 2 to 6 | from 2 to 6 | from 4 to 7 | from 4 to 7 | from 4 to 7 | from 2 to 4 | from 2 to 7 | from 5 to 7 |
| Complexing agent [one or more] | HP-β-CD | 2x-15x | 2x-15x | | | 2x-5x | 2x-5x | | | | |
| | SBE-β-CD | 2x-5x | 2x-5x | | | 2x-5x | 2x-5x | | | 3x-9x | 3x-9x |
| | γ-CD | 3x | 3x | | | | | | | | |
| Anti-Precipitation Agent [one or more] | PVP (4 kD-10 kD) | | in some | | | | in some | | | | in some |
| | HPMC, CMC | | | | | | in some | | | | in some |
| | PEGs | | | | in some | | | in some | | | |
| pH Adjusters [one or more] | 1M HCl | in some | in some | | | in some | in some | | in some | in some | in some |
| | 1M NaOH | | | | | in some | in some | | | in some | in some |
| | Histidine HCl | in some | in some | | | in some | in some | | in some | in some | in some |
| | Citric Acid | | | | | in some | in some | | in some | | |
| | Malic Acid | | | | | in some | in some | | | | |

TABLE 5-continued

| | | 1 | 2 | 3 | 4 | 5 | 6 | 7 | 8 | 9 | 10 |
|---|---|---|---|---|---|---|---|---|---|---|---|
| | | | | | | Drug Form Free Base | | | | | |
| | | | Pazopanib | | | | Sunitinib | | | Axitinib | |
| | | | | | | Drug Form | | | | | |
| | | | Pazopanib Hydrochloride | | | | Sunitinib Malate | | | Axitinib Free Base | |
| | | | | | | Drug Concentration | | | | | |
| | | 5-80 mg/mL | 5-100 mg/mL | 5-40 mg/mL | 5-40 mg/mL | 5-50 mg/ml | 5-50 mg/ml | 1-10 mg/ml | 10-50 mg/ml | 2-6 mg/mL | 2-6 mg/mL |
| | | | | | | pH | | | | | |
| Formulation | | from 4 to 7 | from 5 to 7.5 | from 2 to 6 | from 2 to 6 | from 4 to 7 | from 4 to 7 | from 4 to 7 | from 2 to 4 | from 2 to 7 | from 5 to 7 |
| Buffering Agents [one or more] | Histidine | in some | in some | | | in some | in some | | | in some | in some |
| | Citric Acid | | | | | in some | in some | | Yes | | |
| | Malic Acid | | | | | in some | in some | | | | |
| | Phosphate | | | | | | | | | | |
| Amphiphilic Agents [one or more] | Polysorbates | | | | in some | | | | | | |
| | Poloxamers | | | | in some | | | | | | |
| | Ethoxylated Emulsifiers | | | | in some | | | | | | |
| Non Aqueous Co-solvents [one or more] | DMSO | | | in some | | | | in some | | | |
| | Ethanol | | | in some | | | | | | | |
| | Glycerine | | | in some | | | | in some | | | |
| | Propylene Glycol | | | in some | | | | | | | |
| | Triacetin | | | in some | | | | | | | |
| | N,N-Dimethylacetomide | | | in some | | | | | | | |
| | Pyrrolidone | | | in some | | | | | | | |

Concentration of Therapeutic Agents in Formulation

Solubility of the therapeutic agents is increased in the formulation with acids, cyclodextrins (e.g., SBEβCD (CAPTISOL®), HPβCD, HPγCD), hydrophilic stabilizing agents (e.g., PVP), and/or buffering agents (e.g., citric acid, histidine). For example, solid therapeutic agents are mixed in an aqueous solution with cyclodextrin, buffering agent, and/or other formulation agents of the current invention. The pH of the resulting mixture is adjusted with a base, for example, NaOH, or an acid, for example, citric acid. The mixture is then filtered, and the resulting filtered solution is used to fill the PDS. In some embodiments, the therapeutic agent solubilized in such manner increases solubility of the agent, and further increases stability of the agent in the PDS reservoir.

Non-limiting examples of concentrations (20-80 mg/mL) achieved for Pazopanib, Sunitinib, and Axitinib formulations of the current invention are listed in Table 6 below.

TABLE 6

Formulation Concentrations of Therapeutic Agents

| | Pazopanib | Sunitinib | Axitinib | Linifanib | Motesanib |
|---|---|---|---|---|---|
| Concentrations achieved at pH 7 | 80 mg/mL | 30 mg/mL (50 mg/mL for FB) | 5 mg/mL | 6 mg/mL | 30 mg/mL |
| SBE-β-CD [CAPTISOL ®] Formulations (CD Excess) | 20 mg/mL (5x) 50 mg/mL (2.5x) 80 mg/mL (2.5x) | 20-30 mg/mL (2.5x, 4x) | 5 mg/mL (6x) | 6 mg/mL (8x) | 30 mg/mL (2x) |
| HP-β-CD Formulations (CD Excess) | 20 mg/mL (4x, 5x) | 30 mg/mL (2.5x) | N/A | N/A | N/A |
| Expected Concentration Achieved | Yes (70 mg/mL) | Yes (8 mg/mL) | Yes (0.5 mg/mL) | No (40 mg/mL) | No (128 mg/mL) |

Release Rate of Therapeutic Agents

The release rates for various therapeutic agent formulations are determined using methods known in the art. For example, release rate is determined by methods described in WO 2012/065006 (published May 18, 2012), contents of which are incorporated herein in their entireties.

According to some embodiments of the current invention, the release rate of the therapeutic agent formulation is between about 25 μg/day to about 0.1 μg/day. The release rate of the therapeutic agent decreases over time from about 10 μg/day on day 1 to about 0.1 μg/day on day 90 or more.

For example, the release rate of Pazopanib from the therapeutic device, when associated with HPβCD in a 5:1 ratio in a formulation varies between day 1 and 90, from about 3 μg/day to 1.5 μg/day.

In one embodiment, the release rate of Sunitinib from the therapeutic device, when associated with CAPTISOL® in a 2.5:1 ratio varies between day 1 and 90, from about 6.5 μg/day to about 2 μg/day.

Figure 5:
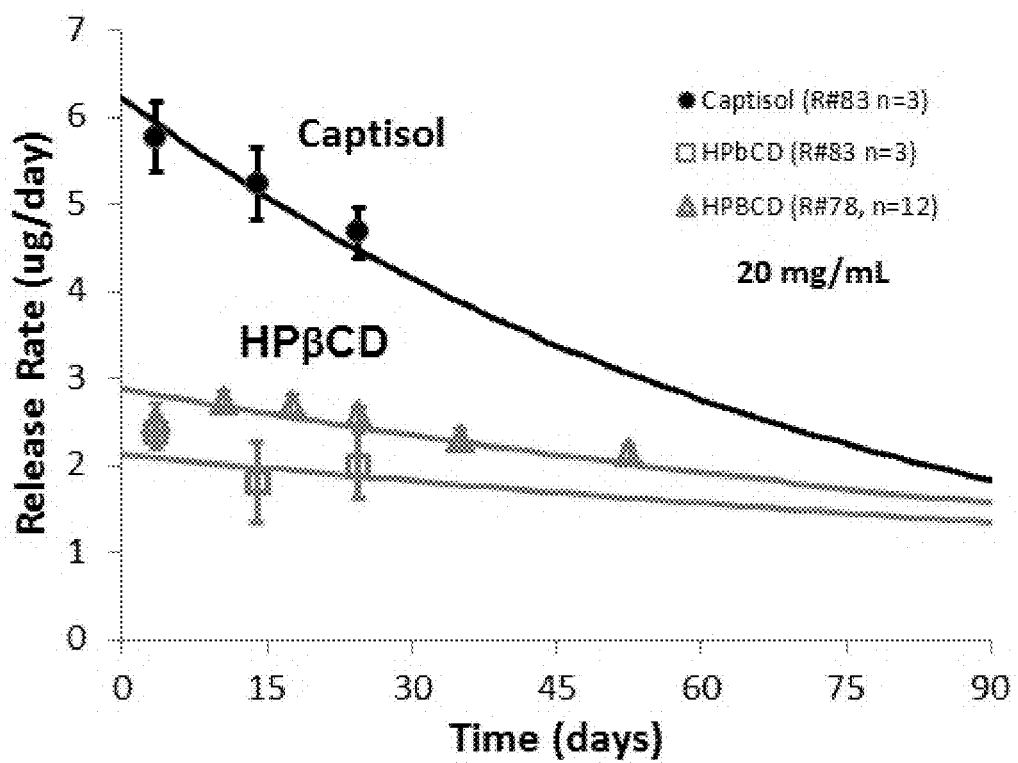
FIG. 5 shows comparative line graphs of the release rate as a function of time (days) for Pazopanib in a formulation comprising CAPTISOL® or HPβCD.

In another embodiment, the release rate of Axitinib from the therapeutic device, when associated with CAPTISOL® in 8:1 ratio varies between day 1 and 90, from about 1.5 μg/day to about 0.1 μg/day. The release rates of Pazopanib in HPβCD in a ratio of 5:1, Sunitinib in CAPTISOL® in a ratio of 2.5:1, and Axitinib in CAPTISOL® in a ratio of 8:1 are shown in FIG. 5.

The ratio of the complexing agent to the therapeutic agent is varied to achieve desired release rate. For example, in one embodiment of the current invention, the release rates of Pazopanib and Sunitinib are higher in CAPTISOL® than the release rate in HPβCD. In one embodiment, the release rate of Pazopanib when in a 5:1 CAPTISOL®: Pazopanib formulation is higher than when in a 5:1 HPβCD:Pazopanib formulation. In another embodiment, the release rate of Sunitinib when in a 2.5:1 CAPTISOL®: Sunitinib formulation is higher than when in a 2.5:1 HPβCD:Sunitinib formulation. The release rate decays faster in smaller volume devices.

The release rate of the therapeutic agent of the current invention in a formulation of 1 mg/mL to about 100 mg/mL under various fill concentrations varies between about 100 μg/mL on day 1 to about 0.01 μg/mL on day 90. For example, in one embodiment the release rate of Pazopanib (about 80 mg/mL)-CAPTISOL® varies between about 60 μg/day at day 1 to about <5 μg/day at around day 90. The release rate of Pazopanib-CAPTISOL® under various fill concentrations alternatively varies between about 25 μg/day at day 1 to about <5 μg/day at around day 90.

In another embodiment of the current invention, release rate of 23 mg/mL Sunitinib-CAPTISOL®, from a 23 μL volume device varies between about 12 μg/day at day 1 to about <1 μg/day at around day 120.

Figure 8:
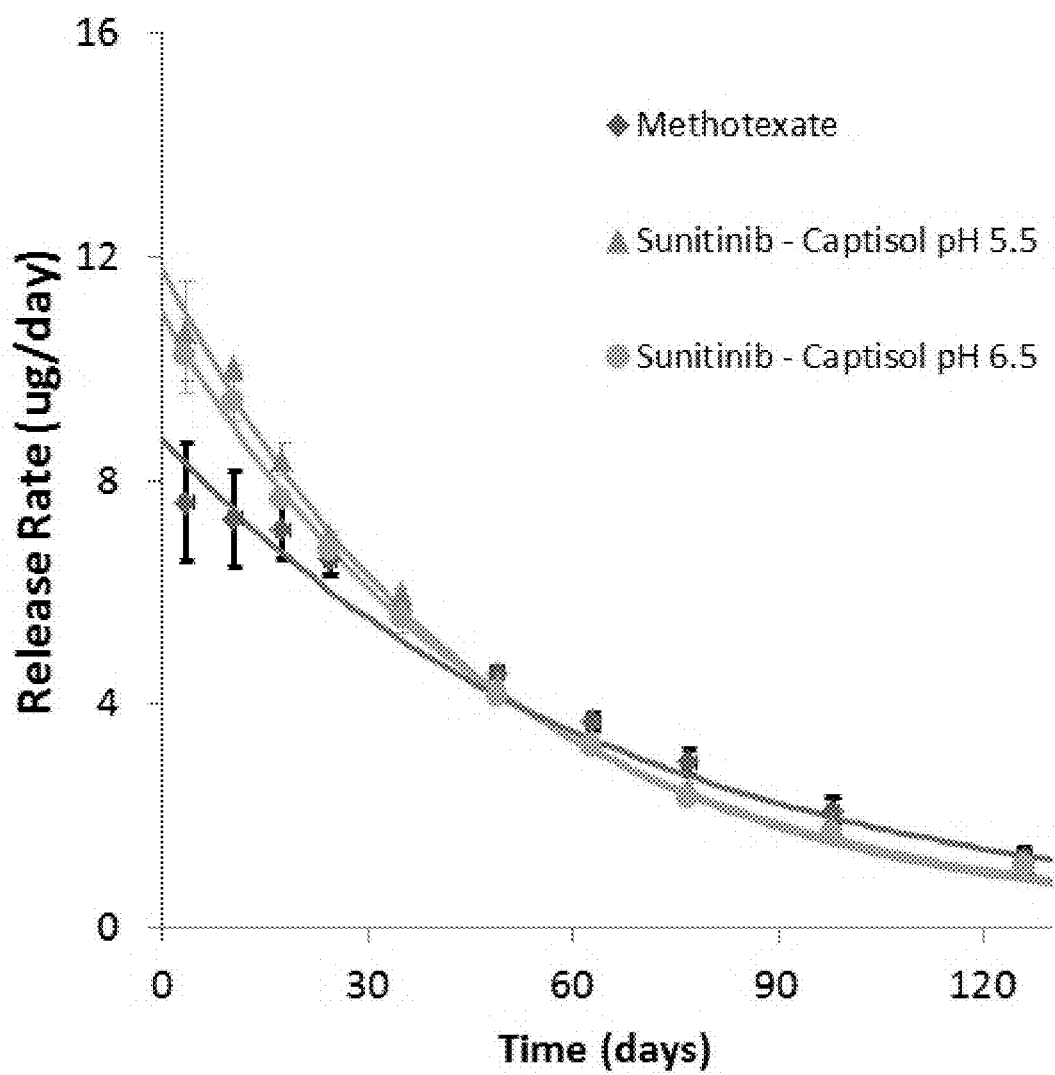
FIG. 8 shows comparative line graphs of the release rate as a function of time for methotrexate, Sunitinib in complex with CAPTISOL® and under varying pH (pH 5.5 and 6.5).
Figure 9:
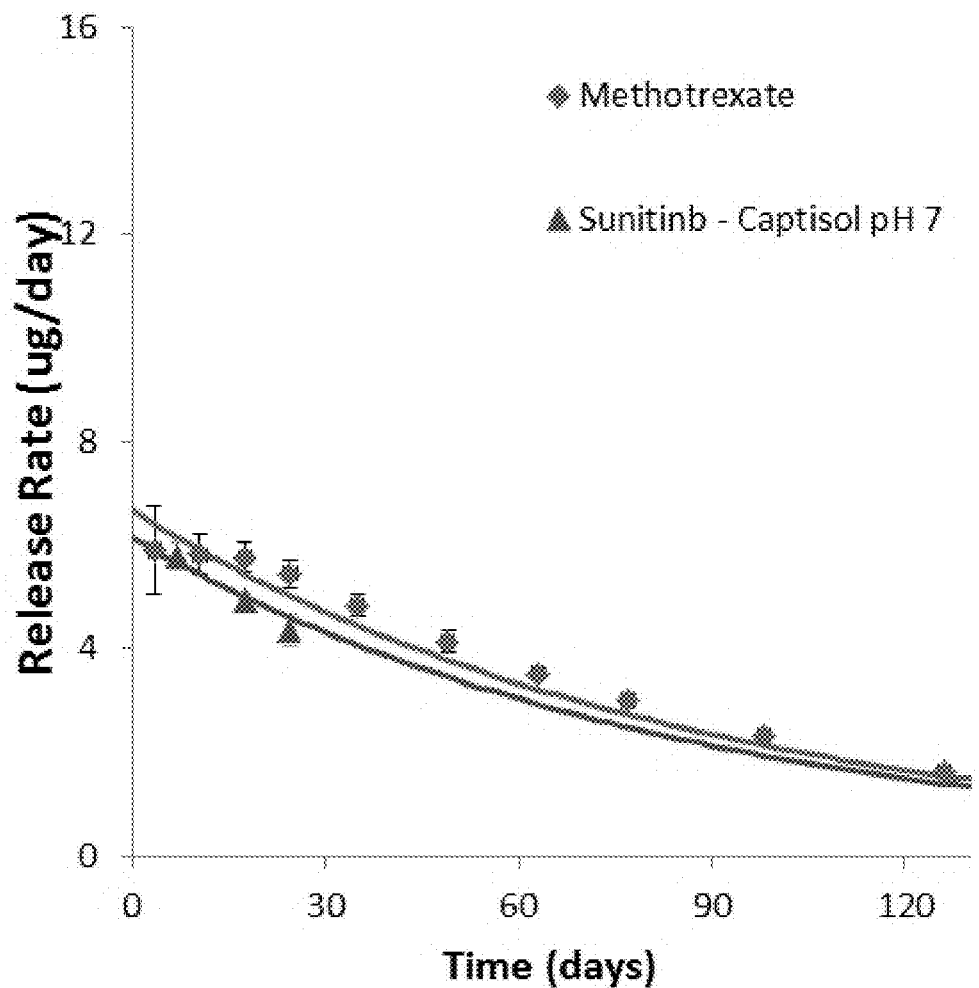
FIG. 9 shows comparative line graphs of the release rate as a function of time for methotrexate, Sunitinib in complex with CAPTISOL® at pH 7.
Figure 10:
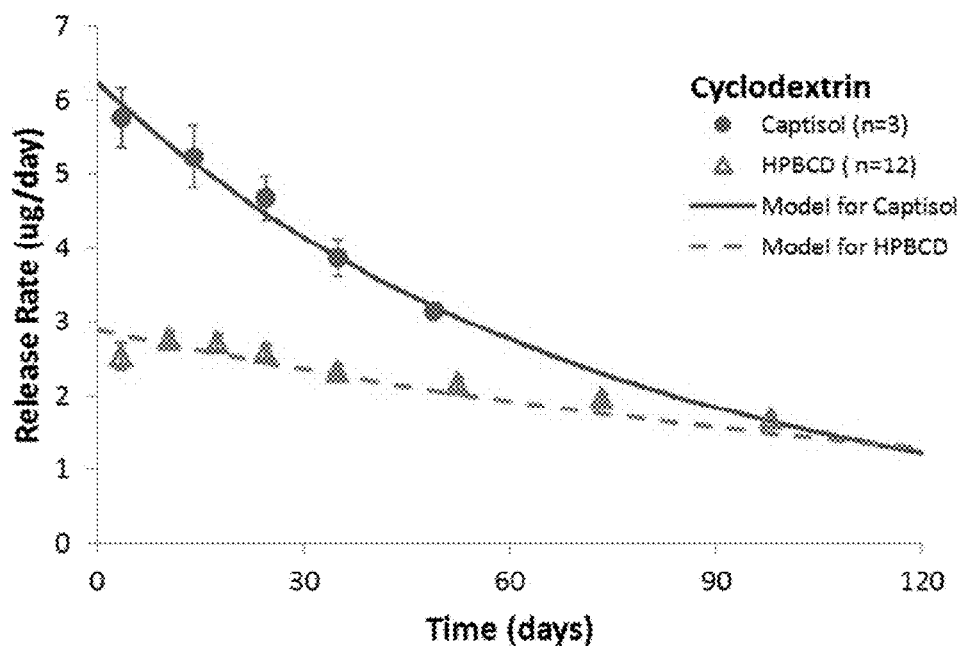
FIG. 10 shows line graphs of in vitro therapeutic agent release from therapeutic device implants filled with 20 mg/mL Pazopanib HCl formulated with CAPTISOL® or HPβCD. Data shows average+/−standard deviation. Lines indicate single exponential model prediction.
Figure 11:
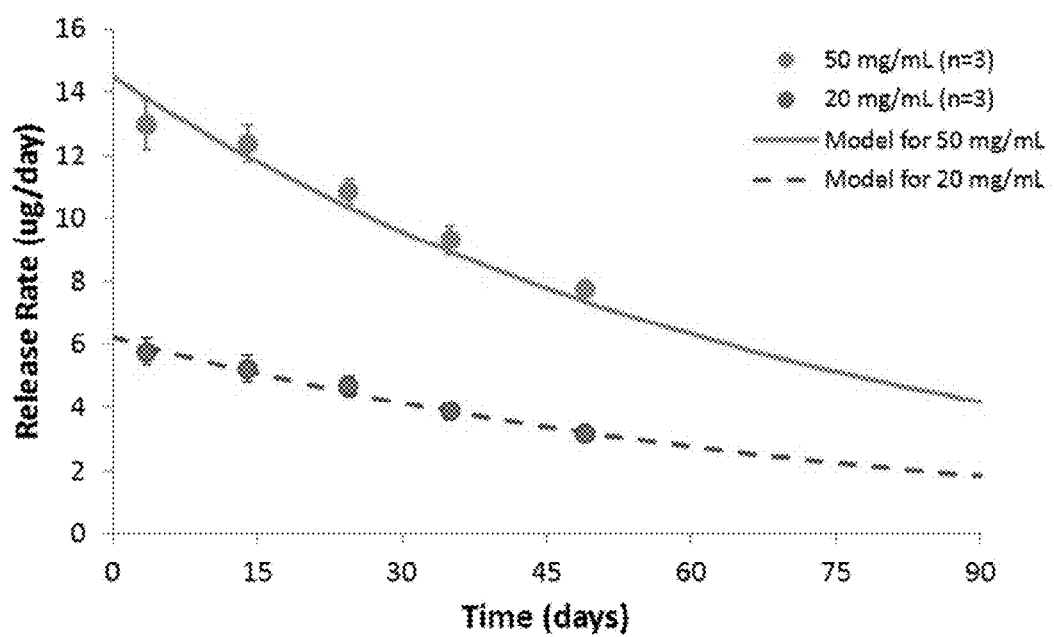
FIG. 11 shows line graphs of in vitro therapeutic agent release from therapeutic device implants filled with 20 or 50 mg/mL Pazopanib HCl formulated with CAPTISOL®. Data shows average+/−standard deviation. Lines indicate single exponential model prediction.
Figure 12:
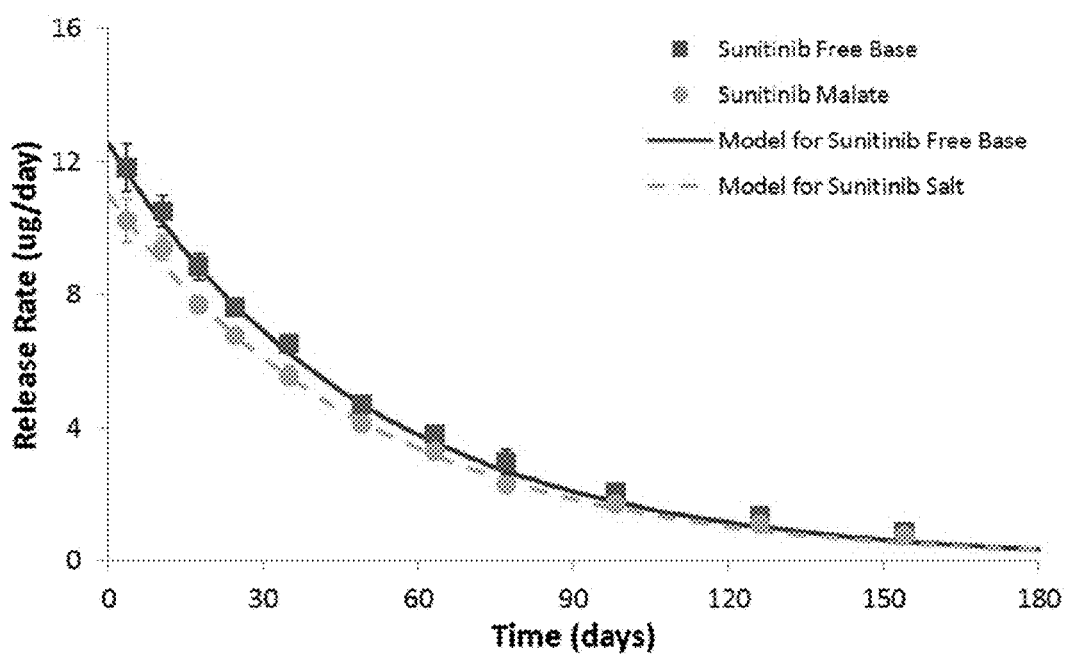
FIG. 12 shows line graphs of in vitro therapeutic agent release from therapeutic device implants filled with 25 mg/mL Sunitinib Free Base or Sunitinib Malate formulated with CAPTISOL®. Data shows average+/−standard deviation. Lines indicate single exponential model prediction.
Figure 13:
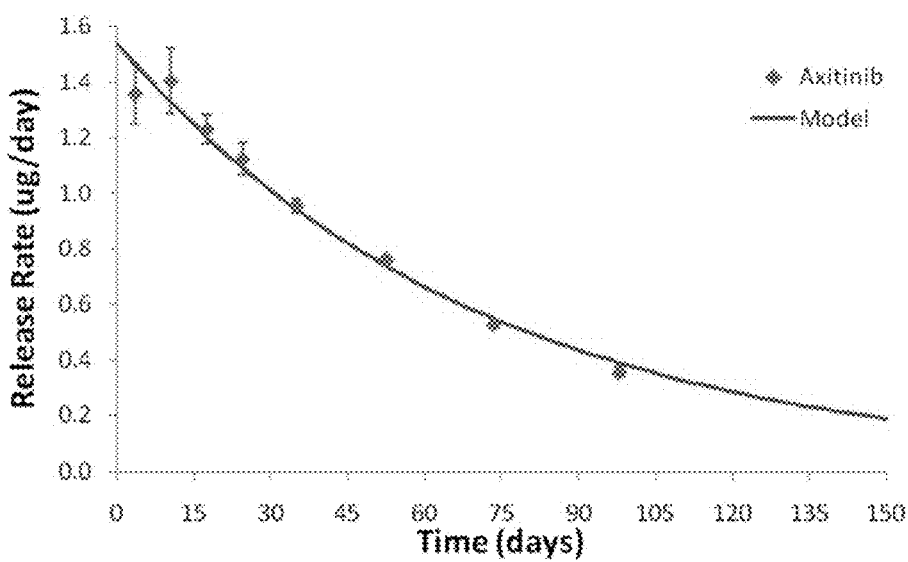
FIG. 13 shows line graphs of in vitro therapeutic agent release from therapeutic device implants filled with about 5 mg/mL Axitinib formulated with CAPTISOL®, described in Example 13. Data shows average+/−standard deviation. Line indicates single exponential model prediction.
Figure 14:
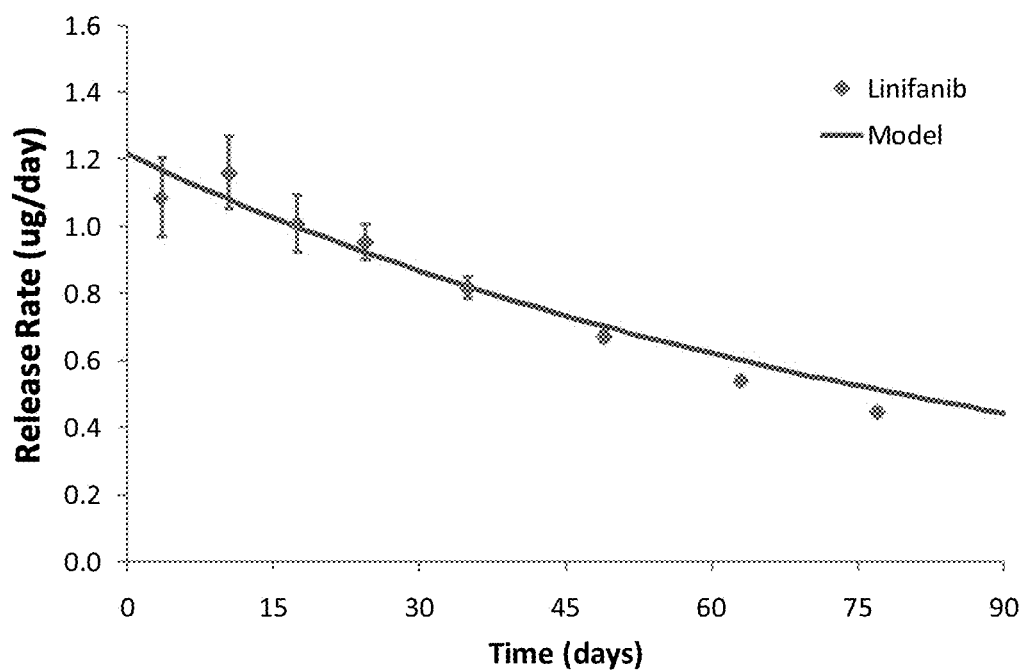
FIG. 14 shows line graphs of in vitro therapeutic agent release from therapeutic device implants filled with 5 mg/mL Linifanib formulated with CAPTISOL®, described in Example 13. Data shows average+/−standard deviation. Line indicates single exponential model prediction.
Figure 15:
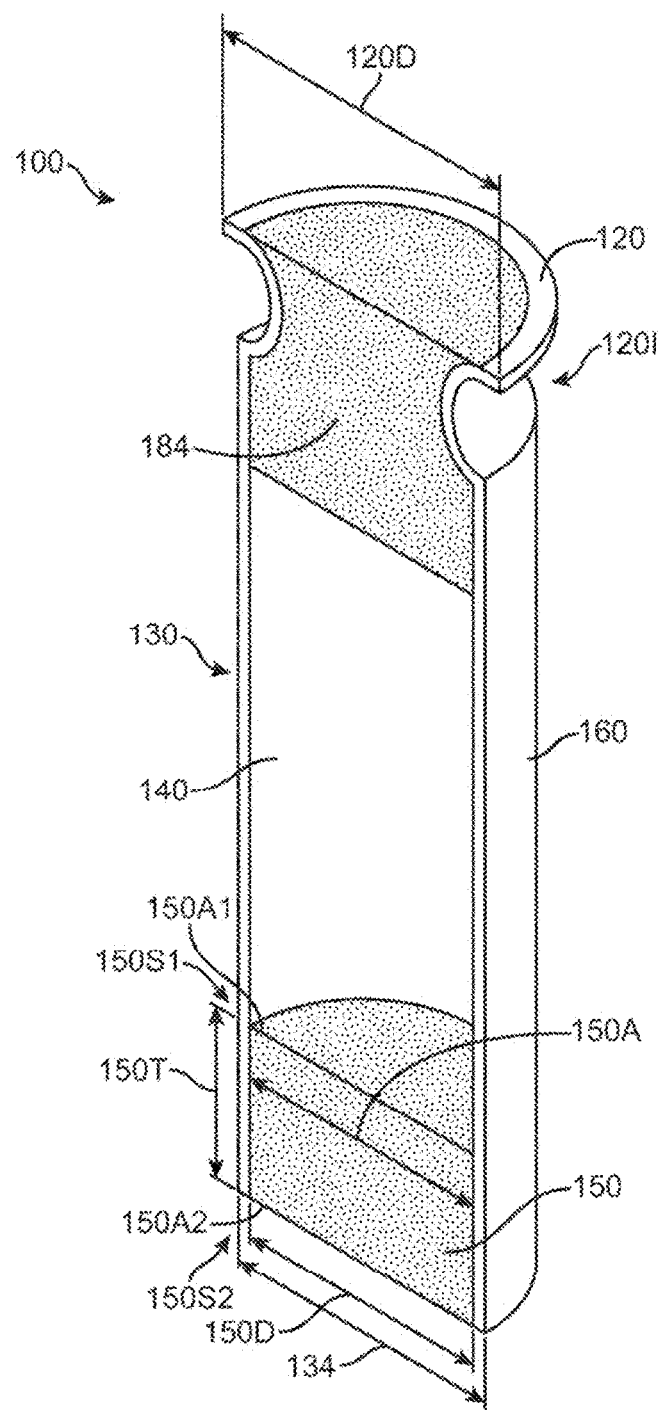
FIG. 15 shows a therapeutic device comprising a reservoir having a penetrable barrier disposed on a first end, a porous structure disposed on a second end to release therapeutic agent for an extended period, and a retention structure comprising an extension protruding outward from the container to couple to the sclera and the conjunctiva.

Embodiments of the current invention also provide that release rate of therapeutic agent in a formulation comprising CAPTISOL® is similar to the release rate of methotrexate (MTX; MTX is an antimetabolite and anti-folate therapeutic agent). Methotrexate is a weak dicarboxylic acid with pKa 4.8 and 5.5, and thus it is mostly ionized at physiologic pH. In some embodiments, the release profiles of a therapeutic agent in formulation comprising CAPTISOL® and formulation of MTX is similar. For example, methotrexate and Sunitinib malate-CAPTISOL® formulations both having approximately 25 mg/mL therapeutic agent concentration in fill solution have similar release profiles. See FIGS. 8 and 9.

In some embodiments, the release rate of the therapeutic agent of the current invention in a formulation of 1 mg/mL to about 100 mg/mL the agent is between 100 μg/mL on day 1 to 0.01 μg/mL, on around or more than 90 days. One of the embodiments of the current invention provides that the release profile of Sunitinib malate-CAPTISOL® at pH 7.0 is similar to the release profile of MTX. See FIG. 9. For example, the release profile of Sunitinib malate-CAPTISOL® formulation at pH 5.5 is from about 12 μg/day at day 1 to about 0.2 μg/day at about day 120; and the release profile of Sunitinib malate-CAPTISOL® formulation at 6.5 is from about 11 μg/day at day 1 to about 0.2 μg/day at about day 120. The release profiles of Sunitinib malate-CAPTISOL® at both pH 5.5 and 6.5 are similar to each other and similar to the release profile of MTX. In an embodiment of the current invention, the release profiles of Sunitinib malate-CAPTISOL® at pH 7.0 and MTX are both from about 7 μg/day at day 1 to about 2 μg/day at day 120.

Stability of Therapeutic Agents in Formulation

Stability of Therapeutic Agents—Half-life: The stability of the therapeutic agent is determined by methods known in the art as discussed supra. The formulations of the current invention are designed to achieve high concentration of therapeutic agents, which are of low solubility in water and/or aqueous buffers for example, PBS buffer. This "solubility" does not reflect the solubility in aqueous solvent under thermodynamic equilibrium conditions. Aqueous solubility is among the first physicochemical parameter measured during the pre-formulation stage of drug development. Solubility dictates many of the subsequent events and approaches in the formulation development, such as formulations used in early animal bioavailability and toxicity studies. Later the rate of dissolution and stability of the dosage form are determined. Poor aqueous solubility is likely to give rise to increased formulation difficulties during clinical development. Thus, it is of interest to accurately measure solubility of sparingly soluble compounds. The descriptive terms for the approximate solubility of Pharmaceutical and National Formulary substances is given by United States Pharmacopeia, USP23, and is shown below in Table 13.

In one embodiment, the therapeutic agent of the current invention is dissolved in 20-50% 2-pyrrolidone in PBS buffer. In yet another embodiment, the therapeutic agent is solubilized, in the presence of PVP and/or trehalose, in an aqueous solution comprising one or more complexing agents. The one or more complexing agents in the solution associates with the therapeutic agent. In some embodiments, association of the complexing agent with the therapeutic agent forms inclusion complexes.

In some embodiments, the complexing agent to therapeutic agent ratio is varied to enhance solubility of the therapeutic agent and also to stabilize the agent up to or at least 6 months after delivery at the target site. Formation of the inclusion complexes is enhanced by adjusting the pH of the formulation between pH ~2-8. The pH of the formulation is adjusted with agents such as citric acid, histidine, and/or phosphate to further increase solubility of the therapeutic agent. The therapeutic agent, when delivered at the vitreous of the eye from a therapeutic device of the current invention, is stable at the vitreous for up to 6 months.

In some embodiments, complexing agents, such as cyclodextrins, which do not cross biological membranes easily and do not affect the PK properties of the therapeutic agents, are used to increase the aqueous concentration of the agent in the reservoir of the therapeutic device of the current invention. For example, the complexing agents are used to increase the stability of the therapeutic agent in the therapeutic agent in the device. The embodiments of the current invention also provide increased stability of the therapeutic agent in the vitreous after delivery.

In one embodiment, the half-life ($T_{1/2}$) of Sunitinib-CAPTISOL® is about 40-90 days; the $T_{1/2}$ of Pazopanib-CAPTISOL® is about 50-55 days; the $T_{1/2}$ of Axitinib is about 45 days. Table 7 below lists non-limiting examples of half-lives of various therapeutic agents of the current embodiments.

Shelf Life Stability of Formulations

Formulations of the current embodiments are stable at the range of stability conditions, including elevated temperatures and light exposure. Shelf life of the formulations is several months at ambient conditions. The formulations of the therapeutic agents have extended shelf life at selected stability conditions.

In some embodiments the formulations have high viscosity. Viscosity measures the resistance of a solution to flow when a stress is applied. The viscosity of a solution is given in poise units. The unit centipoise (cp or the plural cps) is equal to 0.01 poise and is most often used in pharmaceutical applications. Compounds used to enhance viscosity are available in various grades such as 15 cps, 100 cps, etc. The grade number refers to the viscosity, which results when a fixed percentage aqueous solution is made. Viscosity enhancers are used in the formulations of the current invention to increase their viscosity. This enables the formulations to remain in the eye longer and allows more time for the therapeutic agent to exert its therapeutic activity. Commonly used viscosity enhancers, for example, hydroxyethylcellulose; hydroxypropylmethylcellulose; methylcellulose; polyvinyl alcohol, and/or polyvinylpyrrolidone are used in the formulations.

The formulations, including the high viscosity high concentration formulations, are designed to be compatible with the reservoir chamber of the implanted therapeutic device, materials the implanted device is made of, and the release control element.

The current embodiments also provide increasing the half-life of the therapeutic agents, in effect increasing the half-life of the agent at the vitreous, upon intravitreal delivery. The increase in half-life is ascertained by comparing with the half-life the therapeutic agent when injected directly into the vitreous or when delivered topically.

In some embodiments, the half-life of the intravitreal delivered therapeutic agent from the reservoir of the current embodiments is achieved with a porous structure coupled to the reservoir. The half-life of the therapeutic agents in various formulations is measured. Half-life during release of the therapeutic agent is performed, for example, for a formulation comprising a range of Pazopanib HCl concentration and CAPTISOL®.

TABLE 7

Summary of measured half-lives for therapeutic agents formulated with CAPTISOL®

| Therapeutic agent | Fill Conc. (mg/mL) | Therapeutic Device Vol. (mL) | Half-life (days) | Formulation Description |
|---|---|---|---|---|
| Pazopanib | 63.2 | 0.023 | 85 | 63.1 mg/mL, 2.2:1 CAPTISOL®, Histidine, pH 7 |
| Pazopanib | 73.1 | 0.023 | 63 | 73.1 mg/mL, 2.2:1 CAPTISOL®, Histidine, pH 7 |
| Pazopanib | 63.2 | 0.023 | 61 | 63.1 mg/mL, 2.2:1 CAPTISOL®, Histidine, pH 7 |
| Pazopanib | 50.2 | 0.023 | 61 | 50.2 mg/mL, 2.2:1 CAPTISOL®, Histidine, pH 7 |
| Pazopanib | 47.0 | 0.023 | 49 | 47.0 mg/mL, 3.7:1 CAPTISOL®, Histidine, pH 7 |
| Pazopanib | 82.1 | 0.023 | 65 | 82.1 mg/mL, 5:1 CAPTISOL®, Histidine, pH 7 |
| Pazopanib | 20.0 | 0.023 | 51 | 20.0 mg/mL, 5:1 CAPTISOL®, 0.2% PVP, pH 7 |
| Pazopanib | 45.7 | 0.023 | 50 | 45.7 mg/mL, 2.5:1 CAPTISOL®, pH 6 |
| Pazopanib | 73.1 | 0.023 | 42 | 73.1 mg/mL, 2.2:1 CAPTISOL®, Histidine, pH 7 |
| Pazopanib | 63.2 | 0.023 | 43 | 63.1 mg/mL, 2.2:1 CAPTISOL®, Histidine, pH 7 |
| Pazopanib | 47.0 | 0.023 | 36 | 47.0 mg/mL, 3.7:1 CAPTISOL®, Histidine, pH 7 |
| Pazopanib | 82.1 | 0.023 | 42 | 82.1 mg/mL, 5:1 CAPTISOL®, Histidine, pH 7 |
| Pazopanib | 73.1 | 0.023 | 25 | 73.1 mg/mL, 2.2:1 CAPTISOL®, Histidine, pH 7 |
| Pazopanib | 63.2 | 0.023 | 24 | 63.1 mg/mL, 2.2:1 CAPTISOL®, Histidine, pH 7 |
| Pazopanib | 82.1 | 0.023 | 24 | 82.1 mg/mL, 5:1 CAPTISOL®, Histidine, pH 7 |
| Pazopanib | 18.3 | 0.023 | 139 | 18.3 mg/mL, 5:1 HPβCD, 0.2% PVP, pH 7 |
| Pazopanib | 18.6 | 0.023 | 108 | 18.6 mg/mL, 5:1 HPβCD, 0.2% PVP, pH 6 |
| Pazopanib | 17.7 | 0.023 | 99 | 17.7 mg/mL, 5:1 HPβCD, 0.2% PVP, pH 7 |
| Pazopanib | 17.9 | 0.023 | 97 | 17.9 mg/mL, 4:1 HPβCD, 0.2% PVP, pH 6 |
| Pazopanib | 20.3 | 0.023 | 111 | 20.2 mg/mL, 4:1 HPβCD, 0.2% PVP, pH 7 |
| Sunitinib | 23.1 | 0.023 | 88 | 23.1 mg/mL, 2.5:1 CAPTISOL®, Citric Acid 1:1, pH 6.5 |
| Sunitinib | 22.7 | 0.0095 | 27 | 22.7 mg/mL, 4:1 CAPTISOL®, Histidine, Citric Acid 1:1, 3% PVP, pH 7 |

TABLE 7-continued

Summary of measured half-lives for therapeutic agents formulated with CAPTISOL ®

| Therapeutic agent | Fill Conc. (mg/mL) | Therapeutic Device Vol. (mL) | Half-life (days) | Formulation Description |
|---|---|---|---|---|
| Sunitinib | 22.7 | 0.023 | 60 | 22.7 mg/mL, 4:1 CAPTISOL ®, Histidine, Citric Acid 1:1, 3% PVP, pH 7 |
| Sunitinib | 24.9 | 0.023 | 59 | 24.9 mg/mL 4:1 CAPTISOL ®, Citric Acid 1:1, 3% PVP, pH 7 |
| Sunitinib | 20.6 | 0.023 | 52 | 20.6 mg/mL, 2.5:1 CAPTISOL ®, Citric Acid 1:1, 3% PVP, pH 6.5 |
| Sunitinib | 23.1 | 0.023 | 63 | 23.1 mg/mL, 2.5:1 CAPTISOL ®, Citric Acid 1:1, pH 6.5 |
| Sunitinib | 22.7 | 0.0095 | 15 | 22.7 mg/mL, 4:1 CAPTISOL ®, Histidine, Citric Acid 1:1, 3% PVP, pH 7 |
| Sunitinib | 28.6 | 0.023 | 25 | 28.6 mg/mL, 2.5:1 CAPTISOL ®, Citric Acid 1:1, pH 5.5 |
| Sunitinib | 27.3 | 0.023 | 35 | 27.3 mg/mL, 2.5:1 CAPTISOL ®, Citric Acid 1:1, pH 6.5 |
| Sunitinib | 24.5 | 0.023 | 33 | 24.5 mg/mL, 2.5:1 CAPTISOL ®, Citric Acid 1:1, pH 5.5 |
| Sunitinib | 24.2 | 0.023 | 35 | 24.5 mg/mL, 2.5:1 CAPTISOL ®, Citric Acid 1:1, pH 6.5 |
| Sunitinib | 21.2 | 0.023 | 753 | 21.2 mg/mL, 2.5:1 HPβCD, Citric acid 1:1, 3% PVP, pH 6.5 |
| Axitinib | 4.78 | 0.023 | 50 | 4.8 mg/mL, 9:1 CAPTISOL ®, pH 5 |
| Axitinib | 4.83 | 0.023 | 52 | 4.8 mg/mL, 9:1 CAPTISOL ®, Histidine, 1% PVP pH 4 |
| Axitinib | 4.46 | 0.023 | 48 | 4.5 mg/mL, 9:1 CAPTISOL ®, Histidine, 1% PVP pH 5 |
| Axitinib | 3.99 | 0.023 | 41 | 4.0 mg/mL, 9:1 CAPTISOL ®, Histidine, 1% PVP, pH 7 |
| Linifanib | 4.71 | 0.023 | 62 | 4.7 mg/mL, 8:1 CAPTISOL ®, Citric Acid, 1% PVP, pH 6 |
| Linifanib | 5.93 | 0.023 | 72 | 5.9 mg/mL, 8:1 CAPTISOL ®, Citric Acid, 1% PVP, pH 7 |
| Linifanib | 4.75 | 0.023 | 64 | 4.8 mg/mL, 8:1 CAPTISOL ®, Histidine, 1% PVP, pH 6 |
| Linifanib | 4.67 | 0.023 | 58 | 4.7 mg/mL, 8:1 CAPTISOL ®, Histidine, 1% PVP, pH 7 |
| Motesanib | 28.0 | 0.023 | 53 | 28.0 mg/mL, 1.7:1 CAPTISOL ®, pH 7 |

In some embodiments, the stability of the formulations is assessed with High Performance Liquid Chromatography ("HPLC") during development. The stability assessment of the sample based on HPLC analysis is assessed by determining the percent area of therapeutic agent peak to all peak area and percent area of individual degradation peaks to all peak area in order to provide the amount of therapeutic agent content in the sample formulation. Table 8 below listing non-limiting examples of therapeutic agent and control formulations of the current invention.

TABLE 8

| Compound | Complexing agent | Therapeutic agent Concentration range (mg/mL) | Half-life of therapeutic agent delivery from PDS reservoir (days) |
|---|---|---|---|
| Pazopanib | CAPTISOL ® formulation | 20-80 | 50-65 |
| Sunitinib | CAPTISOL ® formulation | 20 | 50-65 |
| Axitinib | CAPTISOL ® formulation | 5 | 40-50 |
| Linifanib | CAPTISOL ® formulation | 20-80 | 55-70 |
| Motesanib | CAPTISOL ® formulation | 20-80 | 50 |
| Methotrexate | in water, no complexing agent | 10-300 | 60 |
| Fluorescein | in water, no complexing agent | 5 | 45 |

Formulations of the current invention are designed to produce the therapeutic agent delivery performance which is tuned by the composition of the formulations in which the therapeutic agent with complexing agent diffuses as a complex entity (rather than a single molecule entity).

Table 9 shows an example of the half-life of therapeutic agent delivery from the PDS reservoir for formulations with HPβCD complexing agent.

TABLE 9

| Compound | Complexing agent | Therapeutic agent Concentration range (mg/mL) | Half-life of therapeutic agent delivery from PDS reservoir (days) |
| --- | --- | --- | --- |
| Pazopanib | HPβCD formulation | 20 | 110 |

Delivery of Therapeutic Agent from the Device

Design of the therapeutic agent delivery formulations for the sustained release from the PDS implant of the current embodiments is based on several considerations. For example, therapeutic agent elution from the PDS is based on molecular diffusion through the Release Control Element (RCE), which consists of irregular shaped channels. The irregular shaped channels were described in WO 2012/065006, contents of which are incorporated herein in their entireties.

Moreover, diffusion takes place both ways, i.e., from the therapeutic agent diffusing out from the filled PDS into the vitreous and from the vitreous into the PDS. This reversible diffusion allows formulation contents to equilibrate with the vitreous over time. Due to diffusion to and from the PDS and vitreous, the designed formulations have to be compatible with the vitreous components and vitreous pH. The formulations also have to be compatible with the high dilution into the vitreous upon release from the PDS reservoir.

The formulations of the current invention are compatible with the vitreous components and vitreous pH. The formulations described in the current embodiments are compatible with the high dilution into the vitreous upon release from the PDS reservoir.

The current embodiments provide tuning of the rate of therapeutic agent delivery from the PDS implant reservoir to achieve the desired sustained release profile and desired tissue levels. According to some embodiments, the tuning is achieved by the design of the PDS implant, which includes a porous structure for controlling therapeutic agent release. The porous structure has porosity and tortuosity, further having geometrical dimensions, and is of materials such as titanium, polymeric, and/or coated and has functionality of the surface. The tuning of the rate of delivery is also achieved by varying the reservoir volume.

In some embodiments, the tuning of the rate of therapeutic agent delivery depends on the formulation composition, formulation agents, pH, nature of the complexing agent, concentration of the complexing agent, formulation viscosity, and/or therapeutic agent concentration in the reservoir.

Formulations of the current invention are designed to produce robust and highly predictable therapeutic agent delivery characteristics and profiles. In some embodiments, the use of a selected complexing agent achieves very similar therapeutic agent delivery characteristics (such as half-life of therapeutic agent delivery from PDS reservoir) for a variety of compounds formulated in that selected complexing agent. The current invention provides that the half-lives of different therapeutic agents are similar within a range of the complexing agent concentrations in a formulation. The therapeutic agent delivery performance and diffusion through the PDS implant for such formulations are similar to that of the non-complexed single molecular entities.

The device for delivery of the current invention comprises a reservoir and a porous structure. For example, the device is the one described in WO 2012/019176, contents of which are incorporated herein in their entireties. A porous structure similar to that of the current embodiment was described in WO 2012/065006, contents of which are incorporated herein in their entireties.

In some embodiments, the porous structure comprises a first side coupled to the reservoir and a second side to couple to the vitreous. The first side comprises a first area and the second side may comprise a second area.

The volume of the reservoir comprises from about 5 μL to about 50 μL of therapeutic agent, or for example from about 10 μL to about 25 μL, for example, 23 μL of therapeutic agent.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. The reservoir comprises a buffer and a suspension of a therapeutic agent comprising solubility within a range from about 1 mg/mL to about 100 mg/mL, such as from about 1 mg/mL to about 40 mg/mL.

In some embodiments, the concentration of the therapeutic agent in the formulation depends on increasing the solubility of the agent in water or aqueous solutions by using any one or more of: complexing agents, pH adjusting agents, solubility/stabilizing agents, amphiphilic agents, buffering agents, non-aqueous solvents, or any combinations thereof. The therapeutic agents of these embodiments are inherently sparingly soluble (parts of solvent required for 1 part of solute=30 to 100), slightly soluble (parts of solvent required for 1 part of solute=100 to 1000), very slightly soluble (parts of solvent required for 1 part of solute=1000 to 10,000), or practically insoluble or insoluble (parts of solvent required for 1 part of solute ≥10,000) in water or an aqueous solution.

The release rate index comprises many values, and the release rate index with the suspension is somewhat higher than for a solution in many embodiments, for example.

The porous structure comprises a needle stop that limits penetration of the needle. The porous structure comprises a plurality of channels configured for the extended release of the therapeutic agent. The porous structure comprises a rigid sintered material having characteristics suitable for the sustained release of the material.

The reservoir and the porous structure are configured to release therapeutic amounts of the therapeutic agent in many ways. The reservoir and the porous structure is configured to release therapeutic amounts of the therapeutic agent corresponding to a concentration of at least about 0.1 μg per ml of vitreous humor or 0.1-25 μg/day for an extended period of at least about three months. The reservoir and the porous structure is configured to release therapeutic amounts of the therapeutic agent corresponding to a concentration of at least about 0.1 μg per ml of vitreous humor and no more than about 10 μg per ml of vitreous humor for an extended period of at least about three months. In some embodiments, the therapeutic agent is a small molecule therapeutic agent suitable for sustained release.

The reservoir and the porous structure are configured to release therapeutic amounts of the therapeutic agent corresponding to a concentration of at least about 0.1 μg per ml of vitreous humor and no more than about 10 μg per ml of vitreous humor for an extended period of at least about 3 months or at least about 6 months. For example, the reservoir and the porous structure are configured to release therapeutic amounts of the therapeutic agent corresponding to a concentration of at least about 0.1 μg per ml of vitreous humor and no more than about 10 μg per ml of vitreous humor for an extended period of at least about twelve months or at least about two years or at least about three years. For example, the reservoir and the porous structure is configured to release therapeutic amounts of the therapeutic agent corresponding to a concentration of at least about 0.01 μg per ml of vitreous humor and no more than about 300 μg per ml of vitreous humor for an extended period of at least about 3 months or 6 months or 12 months or 24 months.

Formulation components added to increase the solubility of the therapeutic agents bind the therapeutic agent so strongly that efficacy at the target tissue is less than ideal in at least some instances. For example, complexing agents, such as cyclodextrin, enable formulations containing high concentrations of low water solubility therapeutic agents. However, high amounts of dilution are required in order to release the therapeutic agent, as discussed, e.g., in Stella et al., *Advanced Drug Delivery Reviews*, 36: 3-16 (1999); and Brewster and Loftsson, *Advanced Drug Delivery Reviews*, 59: 645-666 (2007). Dilutions by a factor of at least 10, often factors of at least 100 or 1000 or even 10,000 are commonly needed to release large fractions of therapeutic agent from complexes with cyclodextrin. Table 10 lists examples of the various solubility parameters of the present disclosure.

about 20%. Porosity is determined from the weight and macroscopic volume or is measured via nitrogen gas adsorption.

The porous structure comprises a plurality of porous structures, and the area used in the equation for calculation comprises the combined area of the plurality of porous structures.

Tuning of Therapeutic Device for Sustained Release Based on an Injection of a Formulation Cyclodextrin formulations that increase the concentration of dissolved therapeutic agent up to 800,000 fold, as high as 1 to 100 mg/mL for therapeutic agents with aqueous solubility of 10 μg/mL or less was developed. Formulations of tyrosine kinase inhibitors (TKIs) in SBEβCD (also referred to by trademark CAPTISOL®) surprisingly diffused at high rates, close to diffusion rates predicted for individual therapeutic agent molecules. The measured diffusion coefficient was compared to the diffusion coefficient predicted (using Stokes-Einstein equation to correct for MW (via volume of diffusing species) and temperature (via temperature dependence of the viscosity of water)) for a molecule of that molecular weight. A measured diffusion coefficient similar to the predicted diffusion coefficient had a diffusion perfor-

TABLE 10

| Descriptive Term | Parts in Solvent Required for 1 part Solute | g/L in water | M = 400 mol/l in water | M = 40000 mol/L in water |
| --- | --- | --- | --- | --- |
| Very soluble | Less than or equal to 1 | More than or equal to 1000 | More than or equal to 2.5 | More than or equal to 0.025 |
| Freely Soluble | 1 to 10 | 1000 to 100 | 2.5 to 0.25 | 0.025 to 0.0025 |
| Soluble | 10 to 30 | 100 to 33 | 0.25 to 0.08 | 0.0025 to 0.0008 |
| Sparingly soluble | 30 to 100 | 33 to 10 | 0.08 to 0.025 | 0.0008 to 0.00025 |
| Slightly soluble | 100 to 1000 | 10 to 1 | 0.025 to 0.0025 | 0.00025 to 0.0000025 |
| Very slightly soluble | 1000 to 10,000 | 1 to 0.1 | 0.0025 to 0.00025 | 0.000025 to 0.0000025 |
| Practically insoluble, or insoluble | More than or equal to 10,000 | Less than or equal to 0.1 | Less than or equal to 0.00025 | Less than or equal to 0.0000025 |

The therapeutic agent delivery device (PDS) combined with a formulation containing a complexing agent such as cyclodextrin offers a unique advantage over all previous applications of cyclodextrin. The reservoir and porous structure of the PDS are configured to achieve the dilutions required to release therapeutic agent from cyclodextrin complexes for extended periods of time. For example, a PDS with 23 μL volume and RRI=0.007 mm implanted into a human eye achieves dilution factors in excess of 10,000 for prolonged periods of time, for example, several months. The sustained high dilution is very different than the minimal dilution that occurs when cyclodextrin formulations are applied as topical drops to the eye. Furthermore, sustained delivery with high dilution for periods of months from the PDS is unique from the short durations (e.g., hours) corresponding to intravenous injections of cyclodextrin formulations.

In some embodiments, the porous structure comprises porosity, a thickness, a channel parameter and a surface area configured to release therapeutic amounts for the extended period. For example, the porous material comprises a porosity corresponding to the fraction of void space of the channels extending within the material. For example, the porosity comprises a value within a range from about 3% to about 70%. In other embodiments, the porosity comprises a value with a range from about 5% to about 10% or from about 10% to about 25%, or for example from about 15% to mance of individual therapeutic agent molecules. A significantly lower measured diffusion coefficient was indicative of slower therapeutic agent release, for example, from diffusion of a multiple molecule entity or effects of increased viscosity.

More than 30 formulation-device combinations filled with Pazopanib, Sunitinib, Axitinib, Linifanib, and Motesanib formulated with CAPTISOL® have measured diffusion coefficients that are close to predicted values for single therapeutic agent molecules of this molecular weight.

Therapeutic agent release rates for certain therapeutic agents from CAPTISOL® formulation/device combinations were similar to diffusion of individual therapeutic agent molecules. This observation was unexpected and surprising because cyclodextrin formulations generally increase solubility of therapeutic agents by forming inclusion complexes of the therapeutic agent inside the toroidal cyclodextrin structure. CAPTISOL® has an average molecular weight of 2160 Dalton. For a 1:1 complex of CAPTISOL® and Pazopanib, with total molecular weight of 2600 Dalton, one would predict a diffusion coefficient of 2.8e-6 $cm^2/s$, or two times slower than the expected diffusion coefficient of Pazopanib single molecules. In addition, some of the formulations with high therapeutic agent and CAPTISOL® (for example, 80 mg/mL Pazopanib with 2.2:1 molar ratio CAPTISOL®:Therapeutic agent) had high viscosity, at least 5 centipoise, in some formulations at least 50 centipoise.

Increased viscosity was expected to slow down therapeutic agent diffusion even further. Instead of diffusing as expected for a larger complex in a viscous medium, CAPTISOL® formulations surprisingly released therapeutic agent at diffusion rates corresponding to single therapeutic agent molecule entities.

In contrast, 21 mg/mL Sunitinib formulated with 2.5:1 molar ratio HPβCD:Therapeutic agent had a different release rate from the device. The measured diffusion coefficient for this formulation/device combination was 3.3e-7 $cm^2/s$ or 20 times lower than the predicted single molecule diffusion coefficient. Furthermore, therapeutic agent release rates from this formulation slowed with time. The performance indicates this formulation did not release therapeutic agent with diffusion rates of single therapeutic agent molecule entities.

Tuning a Device Volume and Release Control Element to Achieve Therapeutic Delivery Profiles for Formulations with Diffusion of Individual Therapeutic Agent Molecule Entities:

The vitreous concentration of the therapeutic agent, and hence also the rate, change by no more than a factor of 2 to 10 from time zero to the end of delivery duration time are desired. Diffusion controlled devices have delivery rates of therapeutic agents proportional to the concentration in the device reservoir, requiring that the change in rate over the delivery duration time be determined from the change in concentration in the device reservoir. The system half-life that would yield the desired change in rate over the delivery duration time are calculated.

For a given device with a suitable reservoir volume and filled with a small molecule therapeutic agent, the systems have a half-life for the therapeutic agent in the device reservoir ranging from 20 to 90 days, or 20 to 120 days. In some embodiments, the half-life of the therapeutic agent in the vitreous is significantly longer than the half-life of the agent injected directly into the vitreous. In some embodiments, the half-life of therapeutics agent, with a half-life of 2-20 hours when injected directly into the vitreous, is extended to between 20 and 70 days upon intravitreal delivery from the PDS.

The current embodiments also provide a system including a therapeutic agent delivery device (PDS) and formulations for therapeutic agent deliver in order to achieve therapeutic delivery rates. The therapeutic delivery rates depend on diffusion rates, which correspond to diffusion of multiple molecule entities. The delivery rates are increased as a function of time by tuning the device. The diffusion rates of the therapeutic agents of the current invention are achieved by one of two means: (A) formulation with high therapeutic agent load, which contain multiple molecular entities, without any significant increase in load size with time is developed; or (B) a device with volume and Release Control Element (RCE) to achieve therapeutic delivery profile for formulations with diffusion of multiple molecule entities is designed.

A multiple molecule entity of the current embodiments is a complex between one therapeutic agent molecule and one complexing agent, for example, cyclodextrin, or is a complex/micelle/aggregate/nanoparticle containing multiple molecules of a therapeutic agent, one complexing agent, for example, cyclodextrin, or other formulation agents (e.g., one or more solubilizing agents, one or more stabilizing agents, one or more pH adjusting agents, one or more buffering agents, or a combination thereof).

Formulations containing 20-100 mg/mL Pazopanib, with 2:1, 3:1, 4:1, 5:1, 6:1, 7:1, 8:1 or 9:1 ratios of HPβCD: therapeutic agent are developed with the release rates of multiple molecular entities. The measured diffusion coefficients are about half of the diffusion coefficient for single molecule. In one embodiment, the therapeutic agent release profile through 16 weeks of cumulative release of the diffusing entities shows that the diffusing entities are not growing over time.

In one embodiment, highest possible therapeutic agent release rate for a specific fill concentration and device volume is more than 150 days. For example, in order to have a system half-life of about 2 months or a highest rate at about 3 months, the formulations of the current embodiments are filled into a device having about 23 μL volume. Alternatively, a system half-life of about 2 months and highest rate at about 3 months are achieved by filling a formulation into a device with 15 μL volume.

In some embodiments, the release rate of a therapeutic agent, for example about 20-100 mg/mL Sunitinib, Pazopanib, or Axitinib with a complexing agent in any ratio between 2:1 and 9:1 (complexing agent, for example, cyclodextrin: agent) with CAPTISOL®, from a device is higher at the time zero and monotonically decreases over time.

High osmolarity of the viscous formulations of the current embodiments influences the release rate of the therapeutic agents from the PDS. For example, 80 mg/mL Pazopanib with 5:1 CAPTISOL®: therapeutic agent has water content of only approximately 0.5 g/mL. As an PDS implant containing a high osmolarity formulation is placed into a liquid environment (e.g., receiver fluid or vitreous of the eye), there is an osmotically driven uptake of water into the formulation, resulting in formulation volume expansion and expulsion or displacement of air from diffusion pathways in the RCE. A high osmotic formulation has the benefit of enabling high and reproducible delivery from RCEs with small pores.

In an embodiment, a formulation of a therapeutic agent in a low therapeutic agent concentration and low viscosity formulation has a lower than expected measured diffusion coefficient. In contrast, the coefficient of complexing agent, for example, cyclodextrin (for example, CAPTISOL®) formulations of Pazopanib and Sunitinib, even for very high viscosity formulations, has diffusion coefficients, which are close to expected coefficients for single therapeutic agent molecules. The low measured diffusion coefficient is due to incomplete wetting of pores for this formulation. The high viscosity cyclodextrin formulations perform better in this respect.

In some embodiments, formulations of the current invention have high therapeutic agent content and low viscosity. In one embodiment the therapeutic agent concentration is further increased in the presence of cyclodextrin. The increased concentration concurrently increases viscosity of the formulations of the current embodiments. In an embodiment, agents such as urea (or other nitrogen containing organic compound, or for example, compounds containing carbonyl groups) and/or sodium chloride (or any other suitable salt) are added to the formulation in order to disrupt hydrogen bonding between solutes in the formulation. The formulation comprising urea (or other nitrogen containing organic compound, or for example, compounds containing carbonyl groups) and/or sodium chloride (or any other suitable salt) reduces viscosity of the formulation. At the same time, the osmolarity of the formulation increases, which contributes to the benefit of wetting diffusion pathways.

The embodiments of the current invention provide therapeutic agent delivery from a diffusion controlled device, which requires that the concentration of the therapeutic agent be higher at the device than the concentration in the target tissue. Delivery of some therapeutic agents is limited by the concentration achievable in the formulation in the reservoir of the device. In some embodiments, agents are added to the formulation to increase the solubility. In yet other embodiments, solubility of some therapeutic agents is increased with ionizable groups, by adjusting pH, and/or including appropriate buffers.

In one embodiment, a diffusive therapeutic agent delivery device, such as the PDS, is used, which allows diffusion in both directions, e.g., from the device reservoir to the vitreous and from the vitreous to the device reservoir. The embodiments of the current invention provide that during delivery of a therapeutic agent formulation, molecular components from the vitreous humor diffuse into the device reservoir and alter the composition of the formulation.

In an embodiment, a formulation of the current invention is in equilibrium with the vitreous at physiological pH. However, the solubility of some therapeutic agents at physiological pH is insufficient for therapeutic agent delivery (e.g., Sunitinib solubility of 10 µg/mL at pH 7.4 but increases to greater than 25 mg/mL at pH 4.1). In some embodiments, solubility of therapeutic agents is increased by altering the formulation such that the agent may not be in equilibrium with the vitreous. For example, one feature of the therapeutic agent delivery device (PDS) is that the pH equilibration across the porous structure is greatly extended over time. For example, in one embodiment, the pH equilibration in the PDS filled with pH 2 formulation takes over 2 months to equilibrate to pH 7. In yet additional embodiments, changes in the formulation solubility after implant into the eye, and consequent precipitation and reduction of delivery rates are avoided by adjusting the pH of the formulation in the device reservoir.

The current embodiments provide a design of a PDS and formulation for maintaining high solubility of therapeutic agent by delaying changes in pH of the formulation in the device reservoir. The parameters for designing the device include properties, for example, porosity, thickness, area that influence the rate of diffusion of hydrogen ions, hydroxide ions, buffer from the vitreous, and formulation components. Formulation parameters include concentrations and diffusivity of components that affect pH including the therapeutic agent itself. In addition, the formulation contains components that serve as a reservoir for pH maintenance; e.g., solid therapeutic agent, micelles, or emulsion droplets containing components with buffering capacity.

The therapeutic device of the current embodiments is tuned to deliver a target therapeutic concentration profile based on the volume of formulation injected into the device. The injected volume comprises a substantially fixed volume, for example within about +/−30% of an intended predetermined target volume. The volume of the reservoir can be sized with the release rate index so as to release the therapeutic agent for an extended time substantially greater than the treatment time of a corresponding bolus injection. The device can also be tuned to release the therapeutic agent based on the half-life of the therapeutic agent in the eye.

The half-life of the therapeutic agent in the vitreous humor of the eye is determined based on the therapeutic agent and the type of eye, for example human, rabbit or monkey, such that the half-life is determined based on the species of the eye, for example. With at least some animal models the half-life of the therapeutic agent in the vitreous humor is shorter than for human eyes, for example by a factor of about two in at least some instances. For small molecules, the half-life in the vitreous humor of the human eye is about two to three hours and is about one hour in the monkey and rabbit animal models. The therapeutic device can be tuned to receive the volume of formulation based on the half-life of the therapeutic agent in the human vitreous humor, or an animal vitreous humor, or combinations thereof. Based on the teachings described herein, a person of ordinary skill in the art can determine empirically the half-life of the therapeutic agent in the eye based on the type of eye and the therapeutic agent, such that the reservoir and porous structure can be tuned together so as to receive the volume of formulation and provide therapeutic amounts for the extended time.

Indications and Methods of Treatment

Disclosed are methods for the treatment of retinal diseases.

Disclosed are methods for the treatment of diseases or conditions of the eye, especially retinopathies and ocular neovascularization. Non-limiting examples of these diseases or conditions include diabetic macular edema, AMD, CNV, NV, DR, ocular ischemia, retinal vein occlusion (central or branch), ocular trauma, surgery induced edema, surgery induced neovascularization, cystoidmacular edema, uveitis, and the like. These diseases or conditions are characterized by changes in the ocular vasculature whether progressive or non-progressive, whether a result of an acute disease or condition, or a chronic disease or condition.

In one aspect of the current invention the formulation is used in the treatment of atrophic AMD. In further embodiment, the formulation is used in the treatment of neovascular (exudative or wet) AMD. The formulation of the current invention treats, prevents progression of, or ameliorates a symptom of vascular leakage and/or neovascularization in the retina.

The disclosed methods relate to preventing or controlling pathologic neovascularization (NV), or treating a disease or condition that is related to the onset of NV by administering to a subject one or more of the disclosed therapeutic agents, and formulations thereof. The present disclosure improves on the earlier finding that intravitreal delivery of Pazopanib inhibited BEGF-induced leakage in a rabbit model, whereas the topical delivery did not. See Iwase et al., Topical pazopanib blocks VEGF-induced vascular leakage and neovascularization in the mouse retina but is ineffective in the rabbit, *Invest. Ophthalmol. Vis. Sci.* (2013) 54(1):503-11.

One aspect of the disclosed method relates to treating or preventing NV by administering to a subject an effective amount of a therapeutic agent or pharmaceutically acceptable salts in formulations with formulation agents including: complexing agents, solubilizing/stabilizing agents, pH adjusting agents, buffering agents, amphiphilic agents, non-aqueous solvents, tonicity agents, or combinations thereof. The complexing agent for use in the formulation for treating or preventing NV is cyclodextrin, for example, CAPTISOL®.

The disclosed methods relate to preventing or controlling ocular neovascularization or treating a disease or condition that is related to the onset of ocular neovascularization by intravitreal delivery of a formulation of the current invention.

Another disclosed method relates to preventing or controlling retinal edema or retinal neovascularization or treating a disease or condition that is related to the onset of retinal edema or retinal neovascularization by intravitreal delivery of a formulation comprising a tyrosine kinase inhibitor and a complexing agent, for example, cyclodextrin.

Another embodiment of this aspect relates to a method for delaying or preventing progression of non-proliferative retinopathy to proliferative retinopathy by intravitreal delivery of a formulation comprising a tyrosine kinase inhibitor and a complexing agent, for example, cyclodextrin.

A further disclosed method relates to treating, preventing or controlling diabetic retinopathy or treating a disease or condition that is related to the onset of diabetic retinopathy by intravitreal delivery of a formulation comprising a tyrosine kinase inhibitor and a complexing agent, for example, cyclodextrin.

Diabetic proliferative retinopathy is characterized by neovascularization. The new blood vessels are fragile and are susceptible to bleeding. The result is scaring of the retina, as well as occlusion or total blockage of the light pathway through the eye due to the over formation of new blood vessels. Typically subjects having diabetic macular edema are suffering from the non-proliferative stage of diabetic retinopathy; however, it is not uncommon for subjects to only begin manifesting macular edema at the onset of the proliferative stage.

Yet a further disclosed method relates to preventing or controlling diabetic macular edema or treating a disease or condition that is related to the onset of diabetic macular edema by intravitreal delivery of a formulation comprising a tyrosine kinase inhibitor and a complexing agent, for example, cyclodextrin.

The following examples are illustrative, but not limiting, of the methods and compositions of the present invention. Other suitable modifications and adaptations of the variety of conditions and parameters normally encountered in therapy and that are obvious to those skilled in the art are within the spirit and scope of the embodiments.

EXAMPLES

The following studies were conducted to develop the formulations of the current invention and evaluating their characteristics at the vitreous upon intravitreal delivery.

Example 1

Sustained Delivery of Low Solubility Compounds
Design of Port Delivery System with Complexing Agents:
Therapeutic agent delivery device (PDS) and formulation to deliver therapeutic agent achieving therapeutic delivery rates with diffusion rates corresponding to diffusion of individual therapeutic agent molecule entities was developed. For example, two approaches were employed: (A) a formulation with high therapeutic agent loading and therapeutic agent diffusion rates of individual therapeutic agent molecule entities was developed; and (B) a device volume and Release Control Element (RCE) was tuned to achieve therapeutic delivery profiles for formulations with diffusion of individual therapeutic agent molecule entities.

Developing a Formulation with High Therapeutic Agent Loading and Therapeutic Agent Diffusion Rates of Individual Therapeutic Agent Molecule Entities:
Cyclodextrin formulations that can increase the concentration of dissolved therapeutic agent up to 800,000 fold, as high as 1 to 100 mg/mL for therapeutic agents with aqueous solubility of 10 μg/mL or less was developed. Formulations of tyrosine kinase inhibitors (TKIs) in SBEβCD (also referred to by trade name CAPTISOL®) surprisingly diffused at high rates, close to diffusion rates predicted for individual therapeutic agent molecules. The rate was assessed by using the measured Release Rate Index (RRI) and volume for a particular device and using the single exponential diffusion model to determine a measured diffusion coefficient for a particular formulation and device combination. The measured diffusion coefficient was compared to the diffusion coefficient predicted (using Stokes-Einstein equation to correct for MW (via volume of diffusing species) and temperature (via temperature dependence of the viscosity of water)) for a molecule of that molecular weight. A measured diffusion coefficient similar to the predicted diffusion coefficient had a diffusion performance of individual therapeutic agent molecules. A significantly lower measured diffusion coefficient was indicative of slower therapeutic agent release, for example, from diffusion of a multiple molecule entity or effects of increased viscosity.

More than 30 formulation-device combinations filled with Pazopanib, Sunitinib, Axitinib, Linifanib, and Motesanib formulated with CAPTISOL® had measured diffusion coefficients that were close to the predicted values for single therapeutic agent molecules of this molecular weight. The diffusion coefficients were measured following the method described in WO 2012/065006.

Therapeutic agent release rates from CAPTISOL® formulation/device combinations were similar to diffusion of individual therapeutic agent molecules. This observation was unexpected and surprising because cyclodextrin formulations generally increase solubility of therapeutic agents by forming inclusion complexes of the therapeutic agent inside the toroidal cyclodextrin structure. CAPTISOL® has an average molecular weight of 2160 Dalton. For a 1:1 complex of CAPTISOL® and Pazopanib, with total molecular-weight of 2600 Dalton, one would predict a diffusion coefficient of 2.8e-6 $cm^2/s$, or two times slower than the expected diffusion coefficient of Pazopanib single molecules. In addition, some of the formulations with high therapeutic agent and CAPTISOL® (for example, 80 mg/mL Pazopanib with 2.2:1 molar ratio CAPTISOL®: Therapeutic agent) had high viscosity, at least 5 centipoise, in some formulations at least 50 centipoise. Increased viscosity was expected to slow down therapeutic agent diffusion even further. Instead of diffusing as expected for a larger complex in a viscous medium, CAPTISOL® formulations surprisingly released therapeutic agent at diffusion rates corresponding to single therapeutic agent molecule entities.

In contrast, 21 mg/mL Sunitinib formulated with 2.5:1 molar ratio HPβCD:Therapeutic agent had a different release rate from the device. The measured diffusion coefficient for this formulation/device combination was 3.3e-7 $cm^2/s$ or 20 times lower than the predicted single molecule diffusion coefficient. Furthermore, therapeutic agent release rates from this formulation slowed with time. The performance indicates this formulation did not release therapeutic agent with diffusion rates of single therapeutic agent molecule entities.

Tuning a Device Volume and Release Control Element (RCE) to Achieve Therapeutic Delivery Profiles for Formulations with Diffusion of Individual Therapeutic Agent Molecule Entities:

The therapeutic device includes a reservoir coupled to a porous structure. FIG. 16 shows a therapeutic device 100 comprising a container 130 having a penetrable barrier 184-disposed on a first end, a porous structure 150 disposed on a second end to release therapeutic agent for an extended period, and a retention structure 120 comprising an extension protrusion of the retention structure may comprise a diameter 120D. The retention structure may comprise an indentation 1201 sized to receive the sclera. The therapeutic device was described in detail in WO 2012/019136, contents of which are incorporated herein in their entireties. The method of tuning the device volume, the RCE, and determining release rate index were described in WO 2012/065006, contents of which are incorporated herein in their entireties.

Example 2

The reservoir for the therapeutic agent and formulation to deliver therapeutic agent were established to achieve therapeutic delivery rates with diffusion rates corresponding to diffusion of multiple molecule entities. The diffusion rates did not increase in size with time with tuning the device. The diffusion rates were measured as described in WO 2012/065006.

A multiple molecule entity may be a complex between one therapeutic agent molecule and a complexing agent, for example (not being limiting), one cyclodextrin, or it may be a complex/micelle/aggregate/nanoparticle containing multiple molecules of either therapeutic agent, cyclodextrin, or other additives (e.g., solubilizing agents such as PVP or surfactant such as Tween 20).

Formulations containing 20 mg/mL Pazopanib, with 4:1 or 5:1 ratios of HPβCD:therapeutic agent, were developed with therapeutic agent release rates of multiple molecule entities. These had measured diffusion coefficients that were about half of the diffusion coefficient for single therapeutic agent molecule. The therapeutic agent release profile through 16 weeks of cumulative release showed the diffusing entities were not growing with time.

More specifically, as shown in Table 7, 18.6 mg/mL Pazopanib in 5:1 HPβCD:Pazopanib ratio combined with a device having 23 µL volume had a system half-life of 108 days. It provided the highest possible therapeutic agent release rate for this fill concentration and device volume at 156 days. Alternatively, a system half-life of about 2 months and highest rate at about 3 months was achieved by filling this formulation into a device with 15 µL volume.

Additional Surprising Benefits of Cyclodextrin Formulations of TKIs Combined in Devices:

The device in this invention may have a release control element (RCE) that is, for example, a rigid, sintered, porous element.

Some of the high therapeutic agent and cyclodextrin formulations have viscosities that are much higher than that of water, e.g., greater than 5 centipoise, in some formulations greater than 50 centipoise. When these viscous formulations of high therapeutic agent and cyclodextrin content were filled into dry devices with smaller pores, there were times when minimal or no liquid was expressed. Initially low therapeutic agent release rates were expected from these filled devices.

An unexpected good performance was observed, which may be attributed to the high osmolarity of the viscous formulations, such as for a 80 mg/mL Pazopanib with 5:1 CAPTISOL®:Therapeutic agent ratio, water content was approximately 0.5 g/mL.

Additional CD Formulation Related Information:

Typically, it is desirable to create formulations with high therapeutic agent content and low viscosity. Addition of cyclodextrin increased therapeutic agent content but generally with concurrent increase in viscosity. Organic agents, e.g., urea, and/or inorganic salts, e.g., sodium chloride may be added to the formulation to disrupt hydrogen bonding between solutes in the formulation, with the goal of reducing viscosity. At the same time, the osmolarity of the formulation may increase, which may contribute to the benefit of wetting diffusion pathways.

Design of Port Delivery System with pH Adjusted Formulation (Acidic pH Formulation Approach):

Therapeutic agent delivery from a diffusion controlled device requires a source of therapeutic agent with a concentration higher than the concentration in the target tissue. Delivery of some therapeutic agents may be limited by the therapeutic agent concentration achievable in the source formulation. Agents may be added to the formulation to increase the solubility. Furthermore, solubility of some therapeutic agents with ionizable groups may be increased by adjusting pH and including appropriate buffers.

Diffusive therapeutic agent delivery devices (as disclosed in WO 2012/065006) allow diffusion in both directions, e.g., from the device reservoir to the vitreous and from the vitreous to the device reservoir. Hence, during delivery, components from the vitreous may diffuse into the device reservoir and alter the composition of the formulation. One approach to address this issue may be to create a formulation that is in equilibrium with the vitreous; i.e., at physiological pH. However, the solubility of some therapeutic agents at physiological pH is insufficient for therapeutic agent delivery (e.g., Sunitinib solubility of 10 µg/mL at pH 7.4 but increases to greater than 25 mg/mL at pH 4.1). If the therapeutic agent solubility is increased by altering the formulation such that it is not in equilibrium with the vitreous, the formulation may change during use, altering the solubility and resulting in precipitation with reduced rates of therapeutic agent delivery.

The therapeutic agent delivery device (PDS) and formulation to delay changes in pH to maintain higher therapeutic agent solubility is designed. The device parameters for designing include, for example, porosity, thickness and area, which influence the rate of diffusion of hydrogen ions, hydroxide ions, and/or buffer from the vitreous, and formulation components. Formulation parameters may include concentrations and diffusivity of components that affect pH including the therapeutic agent itself. In addition, the formulation may contain components that serve as a reservoir for pH maintenance; e.g., solid therapeutic agent, micelles, or emulsion droplets containing components with buffering capacity.

Example 3

Formulation agents in a solution with a high concentration of dissolved therapeutic agent may serve as a buffer. A concentration of the therapeutic agent and properties of the device were selected in order to balance solubility and therapeutic agent concentration in the device reservoir. As time progressed and therapeutic agent may be delivered, the therapeutic agent concentration in the device may be reduced but the solubility may need to be high in order to avoid precipitation.

At pH 5.0, 100 mg/mL concentration of therapeutic agent may dissolve in the formulation. The therapeutic agent may have a MW of 500 Da, with one group becoming positively charged when pH is changed from 7.4 to 5. The device may have a reservoir volume of 25 pt.

Conclusions from Calculations: The therapeutic agent concentration in the device reservoir may drop exponentially from 100 mg/mL at time zero to approximately 10 mg/mL at 6 months. The buffering capacity from the dissolved therapeutic agent may be sufficient to reproducibly maintain pH and solubility sufficient to avoid precipitation for 2-3 months delivery time frame. The time frame for delivery may be up to 6 months.

Example 4

For a suspension approach, a therapeutic agent in a salt form (which provides buffering capacity as additional therapeutic agent dissolves to replace the therapeutic agent delivered) may be formulated. For example, suspension of Sunitinib malate at pH of 6 may be soluble in the 1-10 mg/mL concentration range. As time progresses, therapeutic agent being delivered to vitreous may be replenished by crystalline therapeutic agent. Because the therapeutic agent may be in salt form and may be charged, it may also replenish the buffering capacity of the formulation to maintain the pH and the dissolved therapeutic agent concentration, thereby driving the force for therapeutic agent delivery.

Example 5

Target Estimates

The estimates of the desired target (e.g., VEGFR2 (KDR)) were performed based on the biochemical kinase inhibition assays as the first approximation. To estimate the in-vivo targets, the biological barriers (protein binding, melanin binding), in-vivo efficacy, PK/PD and toxicity for the intended route of administration were considered. Ki×100 was used as a rough estimate for the vitreous levels. See Table 2.

The formulation concentration and target release rate estimates were preformed according to methods known in the art. The rate using the PDS diffusion model at one month and three month are shown in Table 3. The vitreous concentration at three month, release rate, and target formulation concentration were determined. The results are shown in Table 4.

Example 6

Formulation Screening

A solubility screening of the therapeutic agent of the invention was carried out during the pre-formulation stage. For example, the solubility of the therapeutic agents in acids, cyclodextrin (CD) (e.g., SBEβCD (CAPTISOL®), HPβCD, HPγCD), hydrophilic stabilizing agents (e.g., PVP), and buffering agents (e.g., citric acid, histidine) were explored. Systematic formulation screening may include determination of CD:therapeutic agent ratio, pH, therapeutic agent concentration, and agents.

For example, in the formulation process with complexing agents such as cyclodextrins, a vial of solid therapeutic agent was mixed with a vial containing a solution of CD, acid, and agents in water. The pH of the resulting mixture was adjusted by NaOH. The mixture was then be filtered, and the resulting filtered solution was used to fill the PDS device or used to determine its stability.

Based on the initial formulation concentration determination, Pazopanib, Sunitinib, and Axitinib met the desired concentration levels. See Table 6.

Example 7

Release Rates of Various Therapeutic Agent Formulations

The release rates for various therapeutic agent formulations were determined using methods known in the art. For example, the release rates of Pazopanib in HPβCD in a ratio of 5:1 (CD:Agent), Sunitinib in CAPTISOL® in a ratio of 2.5:1 (CD:Agent), and Axitinib in CAPTISOL® in a ratio of 8:1 (CD:Agent) are shown in FIG. 5.

Figure 6:
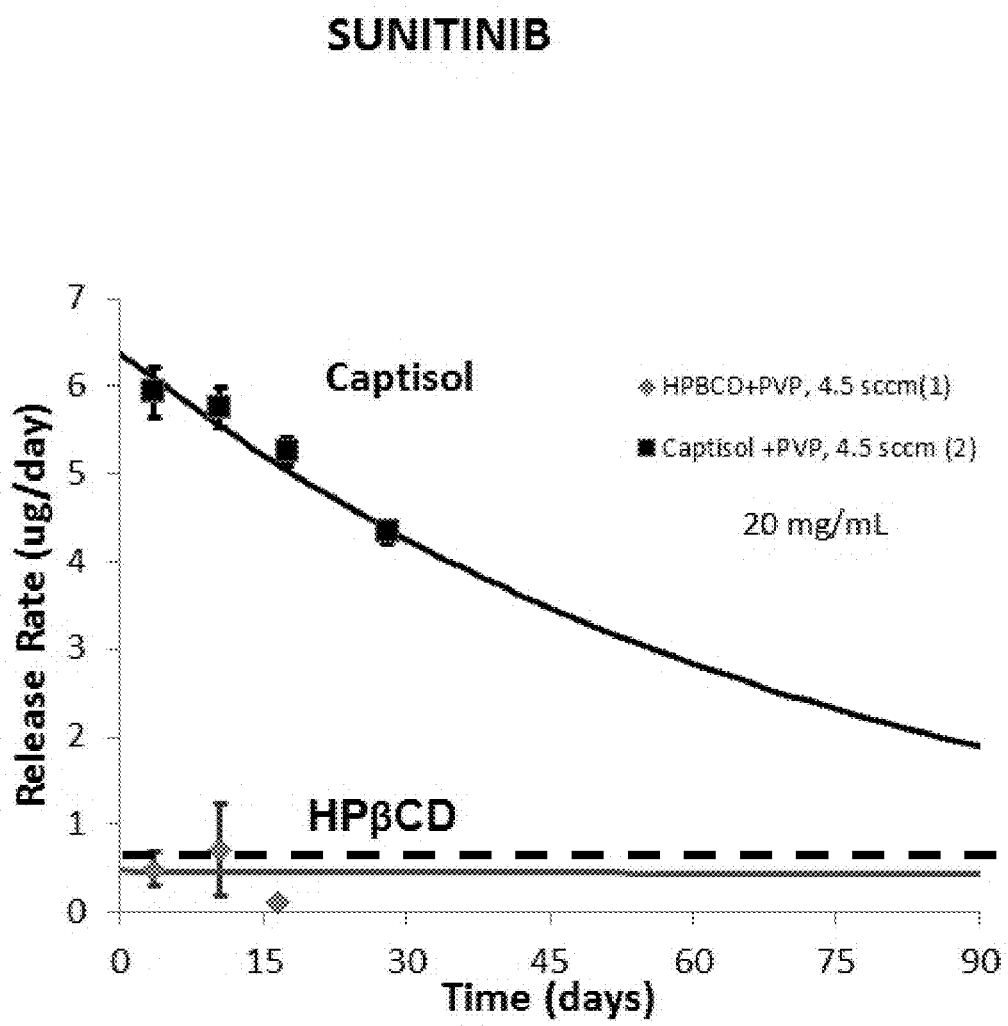
FIG. 6 shows comparative line graphs of the release rate as a function of time (days) for Sunitinib in a formulation comprising CAPTISOL® or HPβCD.
Figure 7:
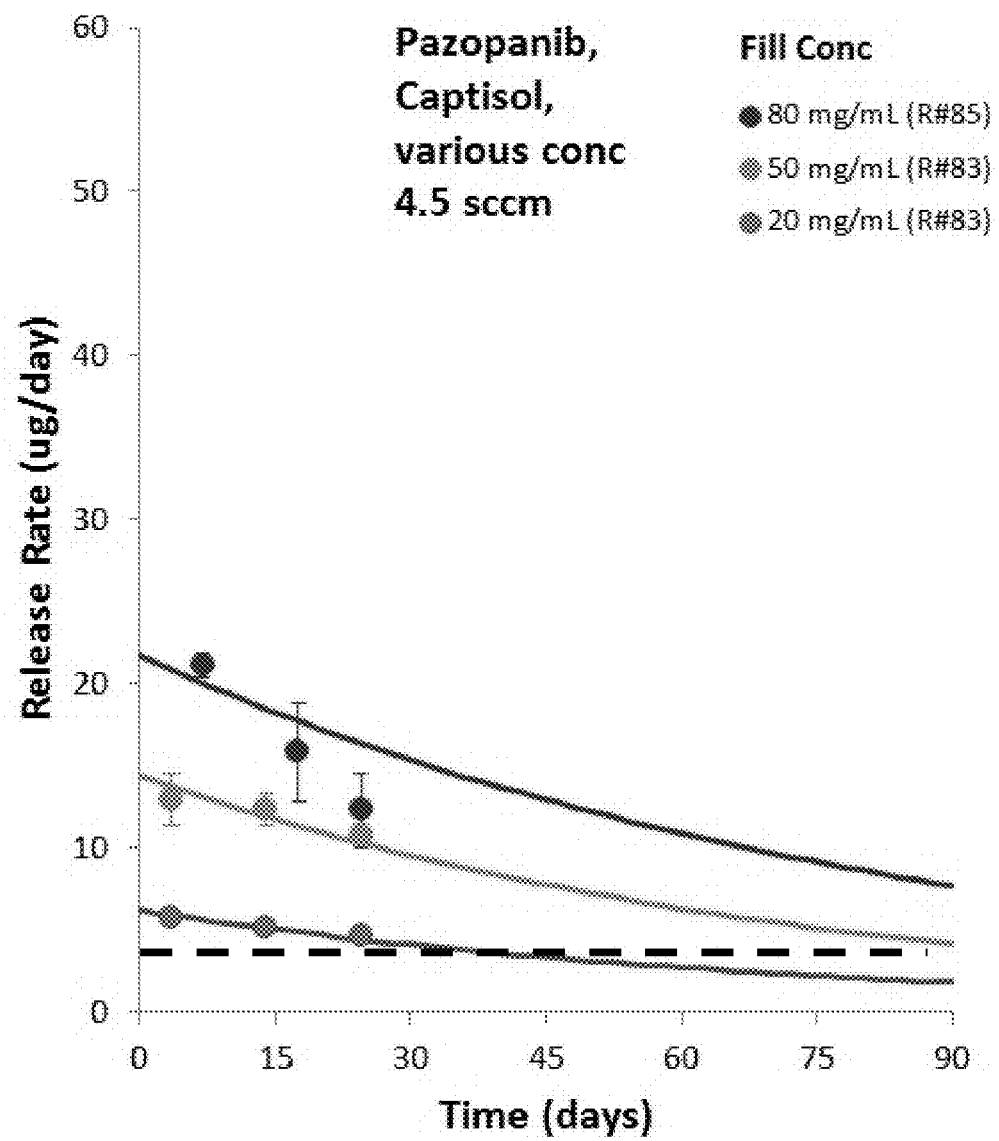
FIG. 7 shows comparative lines graphs of the release rate as a function of time (days) for Pazopanib, in the presence of CAPTISOL®, under fill concentration of 80 mg/mL, 50 mg/mL, and 20 mg/mL.

It was determined that CD affects the release rate. For example, for both Pazopanib and Sunitinib, the release rate was faster in CAPTISOL® than the release rate in HPβCD. See FIGS. 6 and 7. The ratio of Pazopanib to CAPTISOL® was 5:1 (CD:Agent); the ratio of Pazopanib to HPβCD was 5:1 (CD:Agent). The ratio of Sunitinib to CAPTISOL® was 2.5:1 (CD:Agent); the ratio of Sunitinib to HPβCD was 2.5:1 (CD:Agent).

Release rate profiles of CAPTISOL® formulations were similar to the release rate profile of methotrexate (MTX). Methotrexate and Sunitinib malate-CAPTISOL® formulation having approximately 25 mg/mL concentrations in fill solution had similar release profiles. See FIGS. 8 and 9. The release of the therapeutic agent in CAPTISOL® formulations was consistent with the release of MTX under similar conditions. See FIGS. 8 and 9.

Example 8

Stability Testing

The stability of therapeutic agent was determined by methods known in the art. The therapeutic agents were practically insoluble in water (including e.g., PBS buffer; for example the agents were of low aqueous solubility (≥10,000-≥100 parts of solvent required for 1 part of solute)). As such, stability characteristics in aqueous solutions could not be established. 20-50% 2-pyrollidone in PBS buffer was used to dissolve therapeutic agents. The presence of 2-pyrrolidone negatively affected the stability properties of the therapeutic agents (e.g., generating free radicals).

The stability of therapeutic agent formulations was determined by methods known in the art. The conditions used were ambient temperature in the dark, ambient temperature in the light (e.g., photo), at 37° C., or 57° C. The stability assessment of the sample was based on HPLC analysis by determining the percent area of therapeutic agent peak to all peak area and percent area of individual degradation peaks to all peak area to provide the amount of therapeutic agent content in the sample. The results of the stability of the therapeutic agents are summarized in Table 7.

Example 9

Formulations with Complexing Agent

Formulations were prepared by dissolving the required amount of Cyclodextrin, acid, and agents in water. Therapeutic agent (interchangeably referred to as "therapeutic agent") was added and mixed until dissolution. Then sodium hydroxide was added to reach the final pH. Formulation was filtered and then injected into PDS implants to perform therapeutic agent release testing.

Therapeutic agent release testing was performed by measuring the amount of therapeutic agent released by the PDS into a fluid representative of vitreous, maintained at 37° C. in an incubator. The PDS was suspended in a container containing phosphate buffered saline. Periodically, the PDS was transferred into a new container and the concentration of therapeutic agent was measured in the fluid of the previous container. Rates were calculated from the amount of therapeutic agent released divided by the sample collection duration. The percent cumulative release was calculated from the cumulative amount of therapeutic agent divided by the amount of therapeutic agent initially filled into the therapeutic device (PDS). The half-life was calculated from the percent cumulative release at 4 weeks.

Therapeutic agent release was performed on Pazopanib HCl formulated with two types of cyclodextrins. The formulations were filled into therapeutic devices (PDS) having reservoir volume of 23 µL. The results show therapeutic agent release consistent with a single exponential model for extended periods of time, 8 and 16 weeks for CAPTISOL® and HPβCD, respectively. The half-life of Pazopanib in CAPTISOL® is representative of expectations if Pazopanib were diffusing as a single molecule while Pazopanib in HPβCD is diffusing as expected for a therapeutic agent and cyclodextrin complex.

Pazopanib HCl in CAPTISOL®:
Formulation was 20.0 mg/mL Pazopanib HCl, 5:1 CAPTISOL®, 0.2% PVP, pH 7
Half-life=51 days.
Pazopanib HCL in HPβCD:
Data shown is an average for 4 similar formulations:
18.6 mg/mL Pazopanib HCl, 5:1 HPβCD, 0.2% PVP, pH 6
17.7 mg/mL Pazopanib HCl, 5:1 HPβCD, 0.2% PVP, pH 7
17.9 mg/mL Pazopanib HCl, 4:1 HPβCD, 0.2% PVP, pH6
20.2 mg/mL Pazopanib HCl, 4:1 HPβCD, 0.2% PVP, pH 7
Half-life=103 days.

Example 10

Therapeutic agent release was performed with a range of Pazopanib HCl concentration in a CAPTISOL® formulation. The formulations were filled into therapeutic devices (PDS) having reservoir volume of 23 µL.

Irrespective of therapeutic agent concentration, the half-life is representative of expectations if Pazopanib were diffusing as a single molecule.

50 mg/mL Pazopanib HCl in CAPTISOL®:
Formulation was 45.7 mg/mL Pazopanib HCl, 2.5:1 CAPTISOL®, pH 6
Half-life=50 days.
20 mg/mL Pazopanib HCl in CAPTISOL®:
Formulation was 20.0 mg/mL Pazopanib HCl, 5:1 CAPTISOL®, 0.2% PVP, pH 7
Half-life=51 days.

Example 11

Formulations of Sunitinib Free Base and Sunitinib Malate were prepared with CAPTISOL®. The formulations were filled into therapeutic devices (PDS) having reservoir volume of 23 µL. Therapeutic agent release was measured for six months and found to be consistent with the single exponential model. A half-life of 35 days was measured for both Sunitinib Free Base and Sunitinib Malate formulated with CAPTISOL®.

Sunitinib Free Base:
Formulation was 27.3 mg/mL Sunitinib Free Base, 2.5:1 CAPTISOL®, Citric Acid 1:1, pH 6.5
Half-life=35 days.
Sunitinib Malate:
Formulation was 24.5 mg/mL Sunitinib Malate, 2.5:1 CAPTISOL®, Citric Acid 1:1, pH 6.5
Half-life=35 days.

Example 12

A formulation with Sunitinib Malate in CAPTISOL® was filled into therapeutic devices (PDS) with varying properties: Reservoir volume of 9.5 or 23 µL.

Therapeutic agent release was measured for six months and found to be consistent with the single exponential model. A half-life of 35 days was measured for both Sunitinib Free Base and Sunitinib Malate formulated with CAPTISOL®.

For all three conditions, the formulation was 22.7 mg/mL Sunitinib Malate, 4:1 CAPTISOL®, Histidine, Citric Acid 1:1, 3% PVP, pH 7
Half-life=15 days for 9.5 µL reservoir volume
Half-life=27 days for 9.5 µL reservoir volume
Half-life=60 days for 23 µL reservoir volume.

Example 13

Formulations were prepared with Axitinib or Linifanib in CAPTISOL®. The Linifanib formulation was 4.8 mg/mL Linifanib, 9:1 CAPTISOL®, pH 5. The Axitinib formulation was 4.7 mg/mL Axitinib, 8:1 CAPTISOL®, Citric Acid, 1% PVP, pH 6. The formulations were filled into therapeutic devices (PDS) having reservoir volume of 23 µL.

Therapeutic agent release was measured and found to be consistent with the single exponential model. A half-life of 50 days was measured for Axitinib and 62 days for Linifanib formulated with CAPTISOL®.

Example 14

Half-life of formulations filled in the reservoir was measured. More than 30 formulation-device combinations filled with Pazopanib, Sunitinib, Axitinib, Linifanib, and Motesanib formulated with CAPTISOL® had half-lives as expected for therapeutic agent diffusing as a single molecule. See Table 7.

Example 15

Sunitinib Malate in pH Adjusted Formulation (No Complexing Agent)

High dissolved concentrations of Sunitinib Malate were obtained by adjusting the pH of the formulation; i.e., no other agents. The formulations in a therapeutic device (PDS) with relatively stable pH have high therapeutic agent release rates for extended periods of time. The high concentration of therapeutic agent also provided buffering capacity that delayed changes in pH. Release rate of 2-5 µg/day was achieved for 1 month for a pH 2 formulation.

A solution of Sunitinib Malate was prepared by addition of the therapeutic agent to water, followed by addition of hydrochloric acid to yield a clear solution at pH 2 with a final concentration of 41 mg/mL Sunitinib Malate. A portion was also adjusted to pH 4 by addition of sodium hydroxide, yielding a solution with final therapeutic agent concentration of 38 mg/mL Sunitinib Malate.

Example 16

Formulations with Amphiphilic Agents and Non-Aqueous Solvents (No Complexing Agent)

Formulations were created containing high concentrations of insoluble therapeutic agents using amphiphilic agents and non-aqueous solvents. These high concentration formulations may be loaded into therapeutic devices (PDS) to release therapeutic agent at high delivery rates.

5 mg/mL Pazopanib HCl was dissolvable in 20% Povidone (10K PVP) in water.

A solution of 40 mg/mL Pazopanib HCl was achieved in neat Glycerin, neat Propylene Glycol, and Neat Pyrrolidone. In addition, solutions of 5, 40, and 60 mg/mL Axitinib were prepared in neat DMSO, Pyrrolidone, and N,N-Dimethyl acetamide, respectively. Axitinib and Linifanib were formulated in neat PEG 300 at 9 and 20 mg/mL, respectively. While formulations in neat solvents are not common, they can be useful in a refillable sustained release therapeutic device (PDS) by creating high therapeutic agent concentration solutions in the therapeutic device (PDS), for slow release of both therapeutic agent and solvent to the target tissue.

Formulations with high therapeutic agent concentrations were also achieved with the Ethoxylated Emulsifier, KOLLIPHOR® HS 15, also known as SOLUTOL® HS 15. A suspension of therapeutic agent was prepared by adding to SOLUTOL® heated in a water bath at 65° C. Phosphate Buffered Saline (PBS) was added drop wise with stirring. A clear solution with as much as 5 mg/mL Sunitinib Malate, 6 mg/mL Axitinib, or 5 mg/mL Pazopanib HCl was obtained with final formulation of 30% SOLUTOL® and 70% PBS.

Solutions with as high as 20 mg/mL Axitinib were successfully prepared by dissolving 60 mg/mL in Pyrrolidone and then adding PEG 300 and Polysorbate 80. The final formulation contained 32% Pyrrolidone, 31% PEG 300, 5% Polysorbate 80, and 31% water.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A formulation for controlled release of a therapeutic agent in vitreous of an eye from a therapeutic delivery device having a reservoir chamber coupled to a porous structure, the formulation comprising a solution which comprises: (i) from about 20 mg/mL to about 100 mg/mL of a low water soluble therapeutic agent, (ii) a cyclodextrin, and (iii) a polysorbate, a block copolymer of ethylene oxide and propylene oxide, a di-block copolymer of polyethylene oxide and polypropylene oxide, a tri-block copolymer of polyethylene oxide and polypropylene oxide, an ethoxylated emulsifier, a polyethylene glycol ester, sucrose laurate, tocopherol-polyethyleneglycol-succinate, a phospholipid, or a combination of two or more thereof; wherein a ratio of the cyclodextrin to the therapeutic agent is from 1:1 to 15:1; and wherein the therapeutic agent remains in solution in the reservoir chamber upon contact with the vitreous fluid of the eye.

2. A formulation for controlled release of a therapeutic agent in vitreous of an eye from a therapeutic delivery device having a reservoir chamber coupled to a porous structure, the formulation comprising: (i) from about 20 mg/mL to about 100 mg/mL of a low water soluble therapeutic agent, (ii) and a cyclodextrin, and (iii) a polysorbate, a block copolymer of ethylene oxide and propylene oxide, a di-block copolymer of polyethylene oxide and polypropylene oxide, a tri-block copolymer of polyethylene oxide and polypropylene oxide, an ethoxylated emulsifier, a polyethylene glycol ester, sucrose laurate, tocopherol-polyethyleneglycol-succinate, a phospholipid, or a combination of two or more thereof; wherein a ratio of the cyclodextrin to the therapeutic agent is from 1:1 to 15:1.

3. The formulation of claim 2, wherein the therapeutic agent remains in solution in the reservoir chamber upon contact with the vitreous fluid of the eye.

4. The formulation of claim 2, wherein the therapeutic agent has a solubility in water of less than 1 mg/mL.

5. The formulation of claim 2, comprising from about 20 mg/mL to about 80 mg/mL of the therapeutic agent.

6. The formulation of claim 2, wherein the formulation has a pH from about 7 to about 8.

7. The formulation of claim 2, wherein the cyclodextrin is 2-hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, maltosyl-β-cyclodextrin, sulfobutyl ether-β-cyclodextrin, branched-β-cyclodextrin, hydroxypropyl-γ-cyclodextrin, randomly methylated-γ-cyclodextrin, trimethyl-γ-cyclodextrin, or a combination of two or more thereof.

8. The formulation of claim 2, wherein the cyclodextrin is a sulfobutyl ether-β-cyclodextrin.

9. The formulation of claim 8, wherein the sulfobutyl ether-β-cyclodextrin has six or seven sulfobutyl ether groups per cyclodextrin molecule.

10. The formulation of claim 2, wherein the cyclodextrin is a sodium salt of sulfobutyl ether-β-cyclodextrin.

11. The formulation of claim 2, wherein the ratio of the cyclodextrin to the therapeutic agent is in the range of 1.7:1 to 9:1.

12. The formulation of claim 2, wherein the ratio of the cyclodextrin to therapeutic agent achieves a release rate of about 0.1 µg/day to about 25 µg/day.

13. The formulation of claim 2, wherein (iii) is the polysorbate.

14. The formulation of claim 2, further comprising a solubilizing agent, a stabilizing agent, a pH adjusting agent, a buffering agent, or a combination of two or more thereof.

15. The formulation of claim 14, wherein the solubilizing agent is trehalose, methylcellulose, ethylcellulose, sodium carboxymethylcellulose, hydroxypropylmethylcellulose, sodium hyaluronate, sodium alginate, chitosan and its derivatives, polyethylene glycol, glycerin, propylene glycol, triacetin, N,N-dimethylacetamide, poly(vinyl pyrrolidone), pyrrolidone, dimethyl sulfoxide, ethanol, N-(-beta-hydroxyethyl)-lactamide, 1-methyl-2-pyrrolidinone, a triglyceride, monothioglycerol, sorbitol, lecithin, methylparaben, propylparaben, or a combination of two or more thereof.

16. The formulation of claim 14, wherein the pH adjusting agent is sodium hydroxide, hydrochloric acid, citric acid, malic acid, tartaric acid, acetic acid, phosphoric acid, maleic acid, glycine, sodium lactate, lactic acid, sodium citrate, ascorbic acid, sodium acetate, acetic acid, sodium bicarbonate, sodium carbonate, carbonic acid, sodium succinate, succinic acid, sodium benzoate, benzoic acid, sodium phosphates, tris(hydroxymethyl)aminomethane, histidine, histidine hydrochloride, or a combination of two or more thereof.

17. The formulation of claim 2, further comprising sodium chloride, sodium phosphate, or a combination thereof.

18. The formulation of claim 2, wherein the therapeutic agent is solubilized in the formulation comprising the cyclodextrin before or after placing into the reservoir.

19. The formulation of claim 2, wherein the therapeutic agent is stable from at least 30 days to 6 months when (i) in the reservoir; (ii) delivered from the therapeutic delivery device at the vitreous; or (iii) both (i) and (ii).

20. The formulation of claim 2, wherein the therapeutic agent is a tyrosine kinase inhibitor.

21. The formulation of claim 2, wherein the therapeutic agent is sunitinib, pazopanib, linifanib, motesanib, axitinib, sorafenib, or a pharmaceutically acceptable salt of any of the foregoing.

22. A formulation for controlled release of a therapeutic agent in vitreous of an eye from a therapeutic delivery device having a reservoir chamber coupled to a porous structure, the formulation comprising: (i) from about 1 mg/mL to about 100 mg/mL of a low water soluble therapeutic agent, (ii) a cyclodextrin, and (iii) a polysorbate, a block copolymer of ethylene oxide and propylene oxide, a di-block copolymer of polyethylene oxide and polypropylene oxide, a tri-block copolymer of polyethylene oxide and polypropylene oxide, an ethoxylated emulsifier, a polyethylene glycol ester, sucrose laurate, tocopherol-polyethyleneglycol-succinate, a phospholipid, or a combination of two or more thereof; wherein a ratio of the cyclodextrin to the therapeutic agent is from 1:1 to 15:1; and wherein the formulation has a pH from about 7 to about 8.

* * * * *